US008119783B2

(12) United States Patent
Bogin et al.

(10) Patent No.: US 8,119,783 B2
(45) Date of Patent: Feb. 21, 2012

(54) FGF VARIANTS AND METHODS FOR USE THEREOF

(75) Inventors: Oren Bogin, Moshav Ganei (IL); Avner Yayon, Moshav Sitria (IL)

(73) Assignee: ProChon Biotech Ltd., Ness Ziona (IL)

( * ) Notice: Subject to any disclaimer, the term of this patent is extended or adjusted under 35 U.S.C. 154(b) by 192 days.

(21) Appl. No.: 12/416,435

(22) Filed: Apr. 1, 2009

(65) Prior Publication Data

US 2009/0247462 A1     Oct. 1, 2009

Related U.S. Application Data

(63) Continuation of application No. 10/982,514, filed on Nov. 5, 2004, now Pat. No. 7,563,769, which is a continuation of application No. PCT/IL03/00379, filed on May 9, 2003.

(30) Foreign Application Priority Data

May 9, 2002   (IL) .......................................... 149562

(51) Int. Cl.
*C12N 15/11* (2006.01)
*C12N 15/12* (2006.01)
*A61K 38/18* (2006.01)
(52) U.S. Cl. ...................................... 536/23.1; 530/399
(58) Field of Classification Search .................. None
See application file for complete search history.

(56) References Cited

U.S. PATENT DOCUMENTS

| | | | | |
|---|---|---|---|---|
| 4,296,100 | A | 10/1981 | Franco | 424/108 |
| 4,378,347 | A | 3/1983 | Franco | 424/108 |
| 4,683,195 | A | 7/1987 | Mullis et al. | 435/6 |
| 4,683,202 | A | 7/1987 | Mullis et al. | 435/6 |
| 4,950,483 | A | 8/1990 | Ksander et al. | 424/422 |
| 4,965,188 | A | 10/1990 | Mullis et al. | 435/6 |
| 4,994,559 | A | 2/1991 | Moscatelli et al. | 530/399 |
| 5,155,214 | A | 10/1992 | Baird et al. | 530/399 |
| 5,191,067 | A | 3/1993 | Lappi et al. | 530/399 |
| 5,302,702 | A | 4/1994 | Seddon et al. | 530/399 |
| 5,310,883 | A | 5/1994 | Seddon et al. | 530/399 |
| 5,439,818 | A | 8/1995 | Fiddes et al. | 435/240.2 |
| 5,491,220 | A | 2/1996 | Seddon et al. | 530/399 |
| 5,512,460 | A | 4/1996 | Nauro et al. | 435/69.1 |
| 5,571,895 | A | 11/1996 | Kurokawa et al. | 530/399 |
| 5,576,288 | A | 11/1996 | Lappi et al. | 514/2 |
| 5,604,293 | A | 2/1997 | Fiddes et al. | 530/399 |
| 5,614,496 | A | 3/1997 | Dunstan et al. | 514/12 |
| 5,622,928 | A | 4/1997 | Naruo et al. | 514/2 |
| 5,656,598 | A | 8/1997 | Dunstan et al. | 514/12 |
| 5,679,637 | A | 10/1997 | Lappi et al. | 514/2 |
| 5,859,208 | A | 1/1999 | Fiddes et al. | 530/399 |
| 5,989,866 | A | 11/1999 | Deisher et al. | 435/69.4 |
| 5,998,170 | A | 12/1999 | Arakawa et al. | 435/69.4 |
| 6,110,746 | A | 8/2000 | Cohen et al. | |
| 6,221,854 | B1 | 4/2001 | Radomsky | 514/54 |
| 6,231,607 | B1 | 5/2001 | Ben-Bassat et al. | 623/16.11 |
| 6,274,712 | B1 | 8/2001 | Springer et al. | 530/399 |
| 6,281,195 | B1 | 8/2001 | Rueger et al. | 514/21 |
| 6,294,359 | B1 | 9/2001 | Fiddes et al. | 435/69.4 |
| 6,303,585 | B1 | 10/2001 | Spiro et al. | 514/54 |
| 6,352,971 | B1 | 3/2002 | Deisher et al. | 514/2 |

FOREIGN PATENT DOCUMENTS

| | | |
|---|---|---|
| WO | WO 90/01342 | 2/1990 |
| WO | WO 00/47114 | 8/2000 |
| WO | WO 01/07595 | 2/2001 |
| WO | WO 01/38357 | 5/2001 |
| WO | WO 01/39788 | 6/2001 |
| WO | WO 01 /46416 | 6/2001 |
| WO | WO 02/22779 | 3/2002 |
| WO | WO 02/36732 | 5/2002 |
| WO | WO 02/077199 | 10/2002 |
| WO | WO 2004/069298 | 8/2004 |

OTHER PUBLICATIONS

Tokuriki and Tawflik, Current Opinion in Structural Biology 2009, 19: 596-604.*
Seddon et al., Biochemistry, 1995; 34: 741-736.*
Apr. 4, 2007 Requirement for Restriction/Election U.S. Appl. No. 10/982,514 (US Patent 7,563,769).
Jul. 17, 2007 Non-Final Rejection U.S. Appl. No. 10/982,514 (US Patent 7,563,769).
Feb. 1, 2008 Final Rejection U.S. Appl. No. 10/982,514 (US Patent 7,563,769).
Jun. 26, 2008 Advisory Action U.S. Appl. No. 10/982,514 (US Patent 7,563,769).
Sep. 22, 2008 Advisory Action U.S. Appl. No. 10/982,514 (US Patent 7,563,769).
Oct. 23, 2008 Advisory Action U.S. Appl. No. 10/982,514 (US Patent 7,563,769).
Supplementary European Search Report EP 03720833.7, mailed Sep. 29, 2008.
Search Report conducted by the Danish Patent Office dated Jul. 15, 2005 regarding Singapore Patent Application No. 200406581-9.
Search Report conducted by the Australian Patent Office dated Mar. 14, 2008 regarding Singapore Patent Application No. 200607828-1.
Bork, Peer (2000) Powers and pitfalls in sequence analysis: The 70% hurdle. Genome Res. 10(4):398-400.
Bork, Peer and Bairoch, Amos (1996) Go hunting in sequence databases but watch out for the traps. Genet Work, Trends in Genetics 12(10):425-427.
Brenner, Steven E. (1999) Errors in genome annotation. Trends in Genetics 15(4):132-133.
Dell' Accio, Francesco et al., (2001) Molecular markers predictive of the capacity of expanded human articular chondrocytes to form stable cartilage in vivo. Arthritis Rheum. 44(7):1608-19.

(Continued)

*Primary Examiner* — Bridget E Bunner
*Assistant Examiner* — Christina Borgeest
(74) *Attorney, Agent, or Firm* — Winston & Strawn LLP

(57) ABSTRACT

The present invention provides fibroblast growth factor variants demonstrating enhanced receptor subtype specificity and/or affinity. Preferred embodiments include both variants having enhanced activity that act as improved agonists and variants having reduced activity that act as antagonists. Methods of utilizing preferred FGF variants in preparation of medicaments for the treatment of skeletal disorders including skeletal dysplasia, osteoporosis and enhancing bone fracture healing and cartilage healing processes are provided.

6 Claims, 14 Drawing Sheets

OTHER PUBLICATIONS

Doerks, Tobias et al., (1998) Protein annotation: detective work for function prediction. Trends Genet. 14(6):248-250.

Gargiulo, B. J. et al., (2002) Phenotypic modulation of human articular chondrocytes by bistratene A. Eur Cell Mater. 3:9-18.

Kim J. et al., (2002) Alternative type I and I' turn conformations in the β8/β9 β-hairpin of human acidic fibroblast growth factor. Protein Science 11(3):459-66.

Ngo, J. Thomas et al., (1994) Computational complexity, protein structure prediction, and the Levinthal Paradox. In: The Protein Folding Problem and Tertiary Structure Prediction. K. Merz Jr. and S. Le Grand, Editors. 433-506 see also table of contents.

Schmal, H. et al., (2007) bFGF influences human articular chondrocyte differentiation. Cytotherapy 9(2):184-93.

Sfiao, Zhan-Qiang et al., (2006) Effects of intramyocardial administration of slow-release basic fibroblast growth factor on angiogenesis and ventricular remodeling in a rat infarct model. Circ. J. 70(4):471-477.

Skolnick, Jeffrey and Fetrow, Jacquelyn S. (2000) From genes to protein structure and function: novel applications of computational approaches in the genomic era. Trends BioTechnol. 18(1):34-39.

Smith, Temple and Zhang, Xiaolin (1997) The challenges of genome sequence annotation or "The devil is in the details". Nat Biotechnol. 15(12):1222-1223.

Wells, James A. (1990) Additivity of mutational effects in proteins. Biochemistry 29(37):8509-8517.

Abraham J.A., Whang J.L., et al., "Human Basic Fibroblast Growth Factor: Nucleotide Sequence and Genomic Organization", EMBO Journal, vol. 5, pp. 2523-2528, (1986).

A. E. Eriksson et al., XP002936511 "Three-Dimensional structure of human basic fibroblast growth factor". Proceedings of the National Academy of Science of USA, National Academy of Science, Washington, DC, US, vol. 88, pp. 3441-3445, (1991).

Agrawal S, et al., "Pharmacokinetics, Biodistribution, and Stability of Oligodeoxynucleotide Phosphorothioates in Mice", Proc. Natl. Acad. Sci., vol. 88, pp. 7595-7599, (1991).

Bailly K. et al., "Uncoupling of Cell Proliferation and Differentiation Activities of Basic Fibroblast Growth Factor", FASEB Journal, vol. 14, pp. 333-343, (2000).

Bange J. et al., "Cancer Progression and Tumor Cell Motility Are Associated With the FGFR4 Arg[388] Allele", Cancer Research, vol. 62, pp. 840-846, (2002).

Barry A. Springer et al., "Identification and Concerted Function of Two Receptor.; Binding Surfaces on Basic Fibroblast Growth Factor Required for Mitogenesis" The Journal of Biological Chemistry, vol. 269, No. 43, pp. 26879-26884 (1994).

Cappellen, D. et al., "Frequent Activating Mutations of FGFR3 in Human Bladder and Cervix Carcinomas", Nature Genetics, vol. 23, pp. 18-20, (1999).

Chusho, H. et al., "Dwarfism and Early Death in Mice Lacking C-Type Natriuretic Peptide", Proc. Natl. Acad. Sci., (PNAS), vol. 98, No. 7, pp. 4016-4021, (2001).

Coughlin, S. R., et al., "Acidic and Basic Fibroblast Growth Factors Stimulate Tyrosine Kinase Activity In Vivo", Journal of Biological Chemistry, vol. 263, No. 2, pp. 988-993, (1988).

Dvorakova, D., et al., "Changes in the Expression of FGFR3 in Patients With Chronic Myeloid Leukaemia Receiving Transplants of Allogeneic Peripheral Blood Stem Cells", British Journal of Haematology, vol. 113, pp. 832-835, (2001).

Ezzat, S., et al., "Targeted Expression of a Human Pituitary Tumor-Derived Isoform of FGF Receptor-4 Recapitulates Pituitary Tumorigenesis", Journal of Clinical Investigation, vol. 109, No. 1, pp. 69-77, (2002).

Faham, S., et al., "Diversity Does Make a Difference: Fibroblast Growth Factor-Heparin Interactions", Current Opinion in Structural Biology, vol. 8, pp. 578-586, (1998).

Fingl, et al., 1975, The Pharmacological Basis of Therapeutics, Ch. 1, p. 1.

Givol and Yayon, FASEB J. 6 3369, 1992.

Johnson and Williams, Adv. Cancer Res. 60 1993.

Kirikoshi, H, "Molecular Cloning and Characterization of Human FGF-20 on Chromosome 8p21.3-p22", Biochemical and Biophysical Research Communications, vol. 274, No. 2, pp. 337-343, (2000).

Kuroda, S. et al., "Anabolic Effect of Aminoterminally Truncated Fibroblast Growth Factor 4 (FGF4) on Bone", Bone, vol. 25, No. 4, 431-437, (1999).

Nakatake, Y, et al., "Identification of a Novel Fibroblast Growth Factor, FGF-22, Preferentially Expressed in the Inner Root Sheath of the Hair Follicle", Biochimica et Biophysica Acta, vol. 1517, pp. 460-463, (2001).

Necht, et al., Acta Crystallogr. D. Biol. Crystallogr. 53 378, 2001.

Nishimura, T. et al., "Identification of a Novel FGF, FGF-21, Preferentially Expressed in the Liver'", Biochimica et Biophysica Acta, vol. 1492, pp. 203-206, (2000).

Okada-Ban M., et al., "Fibroblast Growth Factor-2", International Journal of Biochemistry & Cell Biology, vol. 32, 263-267, (2000).

Olsen, Shaun K., "Fibroblast Growth Factor (FGF) Homologous Factors Share Structural But Not Functional Homology With FGFs". J Biol Chem. 2003 vol. 278, No. 36; Sep. 5; pp. 34226-34236.

Ornitz, D.M., "FGFs, Heparan Sulfate and FGFRs: Complex Interactions Essential for Development", Bio Essays, vol. 22, 108-112, (2000).

Ornitz, D.M., et al., "Fibroblast Growth Factors", Genome Biology, No. 2, pp. 3005.1-3005.12, (2001).

Ornitz, et al., J. Biol. Chem. 2 11, 15292, 1996.

Pellegrini, L, et al., "Crystal Structure of Fibroblast Growth Factor Receptor Ectodomain Bound to Ligand and Heparin", Nature, vol. 407, pp. 1029-1034, (2000).

Pillai, O., et al., "Polymers in Drug Delivery", Current Opinion Chemical Biology, vol. 5,pp. 447-451, (2001).

Plotnikov, A.N., et al., "Structural Basis for FGF Receptor Dimerization and Activation", Cell, vol. 98, 641-650, (1999).

Plotnikov, A.N., et al., "Crystal Structures of Two FGF-FGFR Complexes Reveal the Determinants of Ligand-Receptor Specificity", Cell, vol. 101, pp. 413-424, (2000).

Sahni, M. et al., Genes Devel. 13 1361, 1999.

Schlessinger, J., et al., "Crystal Structure of a Ternary FGF-FGFR-Heparin Complex Reveals a Dual Role for Heparin in FGFR Binding and Dimerization", Molecular Cell, vol. 6, pp. 743-750, (2000).

Seno, M., et al., "Carboxyl-terminal Structure of Basic Fibroblast Growth Factor Significantly Contributes to its Affinity for Heparin", Eur. J. Biochem. vol. 188, pp. 239-245, (1990).

Sleeman, et al., Gene 271 171, 2001.

Stauber, D.J., et al., "Structural Interactions of Fibroblast Growth Factor Receptor With its Liands", Proc. Natl. Acad. Sci., PNAS, vol. 97, No. 1, 49-54, (2000).

Tsutomu, Arakawa et al., "Production and Characterization of an Analog of Acidic Fibroblast Growth Factor With Enhanced Stability and Biological Activity" Protein Engineering, vol. 6, No. 5, pp. 541-546, (1993).

Vajo et al., Endocrine Rev 23 23, 2000.

Yamashita, T., et al., "Identification of a Novel Fibroblast Growth Factor, FGF-23, Preferentially Expressed in the Ventrolateral Thalamic Nucleus of the Brain", Biochemical and Biophysical Research Communications, vol. 277, pp. 494-498, (2000).

Yayon, A., et al., "Cell Surface, Heparin-Like Molecules Are Required for Binding of Basic Fibroblast Growth Factor to its High Affinity Receptor", Cell, vol. 64, pp. 841-848, (1991).

Yee, C.J., et al., "Analysis of Fibroblast Growth Factor Receptor 3 S249C Mutation in Cervical Carcinoma", Journal of the National Cancer Institute, vol. 92, No. 22, 1848,4849 2000).

J. Zhang, et al., Three-Dimensional Structure of Human Basic Fibroblast Growth Factor, a Structural Homolog of Interleukin 1611, Proc. Nat. Acad. Sci., (PNAS), vol. 88, pp. 3446-3450, (1991).

Zhu, H., et al., "Analysis of High-Affinity Binding Determinants in the Receptor Binding Epitope of Basic Fibroblast Growth Factor", Protein Engineering, vol. 10, No. 4, pp. 417-421, (1997).

Zhu, H. et al., "GLU-96 of Basic Fibroblast Growth Factor is Essential for High Affinity Receptor Binding" Journal of Biological Chemistry, American, Society of Biolochemical Biologists, Birmingham US, vol. 270, No. 37, pp. 21869-21874, (1995).

Hecht et al., Acta Crystallogr. D. Biol. Crystallogr. 57,378, 2001.

\* cited by examiner

Figure 9B (x100) (x200)

1 week 2 weeks 6 weeks

Figure 13A W144G
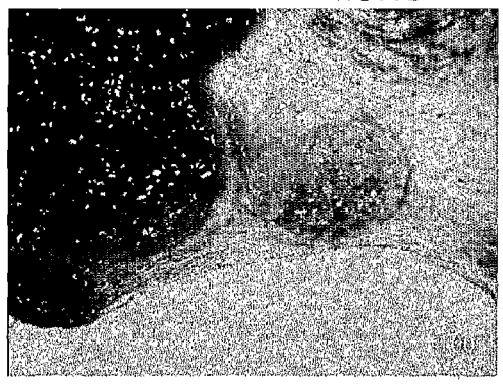
Figure 13B
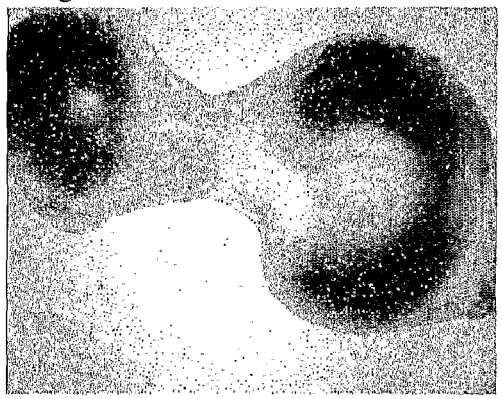
Figure 13C  N111R
Figure 13D  -ligands

SEQUENCE LISTING

<160> NUMBER OF SEQ ID NOS: 96

<210> SEQ ID NO 1
<211> LENGTH: 155
<212> TYPE: PRT
<213> ORGANISM: HOMO SAPIENS
<220> FEATURE:
<221> NAME/KEY: MISC_FEATURE
<222> LOCATION: (111)..(111)
<223> OTHER INFORMATION: X is other than N and more preferably selected from R or G.
<220> FEATURE:
<221> NAME/KEY: MISC_FEATURE
<222> LOCATION: (111)..(111)
<223> OTHER INFORMATION: X is other than N and more preferably selected from R or G.

<400> SEQUENCE: 1

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Xaa Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155

<210> SEQ ID NO 2
<211> LENGTH: 155
<212> TYPE: PRT
<213> ORGANISM: HOMO SAPIENS

<400> SEQUENCE: 2

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Gly Tyr
            100                 105                 110

```
Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155
```

<210> SEQ ID NO 3
<211> LENGTH: 155
<212> TYPE: PRT
<213> ORGANISM: HOMO SAPIENS

<400> SEQUENCE: 3

```
Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Arg Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155
```

<210> SEQ ID NO 4
<211> LENGTH: 155
<212> TYPE: PRT
<213> ORGANISM: HOMO SAPIENS
<220> FEATURE:
<221> NAME/KEY: MISC_FEATURE
<222> LOCATION: (111)..(111)
<223> OTHER INFORMATION: X is other than N and more preferably
      selected from R or G.

<400> SEQUENCE: 4

```
Met Ala Gln Gly Gln Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Xaa Tyr
```

-continued

```
                    100                 105                 110
Asn Thr Tyr Arg Ser Arg Lys Tyr Thr Ser Trp Tyr Val Ala Leu Lys
            115                 120                 125

Arg Thr Gly Gln Tyr Lys Leu Gly Ser Lys Thr Gly Pro Gly Gln Lys
            130                 135                 140

Ala Ile Leu Phe Leu Pro Met Ser Ala Lys Ser
145                 150                 155

<210> SEQ ID NO 5
<211> LENGTH: 155
<212> TYPE: PRT
<213> ORGANISM: HOMO SAPIENS

<400> SEQUENCE: 5

Met Ala Gln Gly Gln Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Gly Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155

<210> SEQ ID NO 6
<211> LENGTH: 206
<212> TYPE: PRT
<213> ORGANISM: HOMO SAPIENS
<220> FEATURE:
<221> NAME/KEY: MISC_FEATURE
<222> LOCATION: (165)..(165)
<223> OTHER INFORMATION: X is other than N and more preferably G

<400> SEQUENCE: 6

Met Ser Gly Pro Gly Thr Ala Ala Val Ala Leu Leu Pro Ala Val Leu
1               5                   10                  15

Leu Ala Leu Leu Ala Pro Trp Ala Gly Arg Gly Gly Ala Ala Ala Pro
            20                  25                  30

Thr Ala Pro Asn Gly Thr Leu Glu Ala Glu Leu Glu Arg Arg Trp Glu
        35                  40                  45

Ser Leu Val Ala Leu Ser Leu Ala Arg Leu Pro Val Ala Ala Gln Pro
    50                  55                  60

Lys Glu Ala Ala Val Gln Ser Gly Ala Gly Asp Tyr Leu Leu Gly Ile
65                  70                  75                  80

Lys Arg Leu Arg Arg Leu Tyr Cys Asn Val Gly Ile Gly Phe His Leu
                85                  90                  95

Gln Ala Leu Pro Asp Gly Arg Ile Gly Gly Ala His Ala Asp Thr Arg
```

```
                    100                 105                 110
Asp Ser Leu Leu Glu Leu Ser Pro Val Glu Arg Gly Val Ser Ile
            115                 120                 125

Phe Gly Val Ala Ser Arg Phe Phe Val Ala Met Ser Ser Lys Gly Lys
        130                 135                 140

Leu Tyr Gly Ser Pro Phe Phe Thr Asp Glu Cys Thr Phe Lys Glu Ile
145                 150                 155                 160

Leu Leu Pro Asn Xaa Tyr Asn Ala Tyr Glu Ser Tyr Lys Tyr Pro Gly
                165                 170                 175

Met Phe Ile Ala Leu Ser Lys Asn Gly Lys Thr Lys Lys Gly Asn Arg
        180                 185                 190

Val Ser Pro Thr Met Lys Val Thr His Phe Leu Pro Arg Leu
        195                 200                 205

<210> SEQ ID NO 7
<211> LENGTH: 152
<212> TYPE: PRT
<213> ORGANISM: HOMO SAPIENS
<220> FEATURE:
<221> NAME/KEY: MISC_FEATURE
<222> LOCATION: (111)..(111)
<223> OTHER INFORMATION: X is other than N and more preferably G
      (N165G)

<400> SEQUENCE: 7

Met Ala Arg Leu Pro Val Ala Ala Gln Pro Lys Glu Ala Ala Val Gln
1               5                   10                  15

Ser Gly Ala Gly Asp Tyr Leu Leu Gly Ile Lys Arg Leu Arg Arg Leu
            20                  25                  30

Tyr Cys Asn Val Gly Ile Gly Phe His Leu Gln Ala Leu Pro Asp Gly
        35                  40                  45

Arg Ile Gly Gly Ala His Ala Asp Thr Arg Asp Ser Leu Leu Glu Leu
    50                  55                  60

Ser Pro Val Glu Arg Gly Val Val Ser Ile Phe Gly Val Ala Ser Arg
65                  70                  75                  80

Phe Phe Val Ala Met Ser Ser Lys Gly Lys Leu Tyr Gly Ser Pro Phe
                85                  90                  95

Phe Thr Asp Glu Cys Thr Phe Lys Glu Ile Leu Leu Pro Asn Xaa Tyr
            100                 105                 110

Asn Ala Tyr Glu Ser Tyr Lys Tyr Pro Gly Met Phe Ile Ala Leu Ser
        115                 120                 125

Lys Asn Gly Lys Thr Lys Lys Gly Asn Arg Val Ser Pro Thr Met Lys
    130                 135                 140

Val Thr His Phe Leu Pro Arg Leu
145                 150

<210> SEQ ID NO 8
<211> LENGTH: 208
<212> TYPE: PRT
<213> ORGANISM: HOMO SAPIENS
<220> FEATURE:
<221> NAME/KEY: MISC_FEATURE
<222> LOCATION: (144)..(144)
<223> OTHER INFORMATION: X is other than W and more preferably
      selected from G, R, E or V (W144X)

<400> SEQUENCE: 8

Met Ala Pro Leu Gly Glu Val Gly Asn Tyr Phe Gly Val Gln Asp Ala
1               5                   10                  15

Val Pro Phe Gly Asn Val Pro Val Leu Pro Val Asp Ser Pro Val Leu
```

```
                    20                  25                  30
Leu Ser Asp His Leu Gly Gln Ser Glu Ala Gly Gly Leu Pro Arg Gly
            35                  40                  45
Pro Ala Val Thr Asp Leu Asp His Leu Lys Gly Ile Leu Arg Arg Arg
        50                  55                  60
Gln Leu Tyr Cys Arg Thr Gly Phe His Leu Glu Ile Phe Pro Asn Gly
65                  70                  75                  80
Thr Ile Gln Gly Thr Arg Lys Asp His Ser Arg Phe Gly Ile Leu Glu
                85                  90                  95
Phe Ile Ser Ile Ala Val Gly Leu Val Ser Ile Arg Gly Val Asp Ser
            100                 105                 110
Gly Leu Tyr Leu Gly Met Asn Glu Lys Gly Glu Leu Tyr Gly Ser Glu
        115                 120                 125
Lys Leu Thr Gln Glu Cys Val Phe Arg Glu Gln Phe Glu Glu Asn Xaa
    130                 135                 140
Tyr Asn Thr Tyr Ser Ser Asn Leu Tyr Lys His Val Asp Thr Gly Arg
145                 150                 155                 160
Arg Tyr Tyr Val Ala Leu Asn Lys Asp Gly Thr Pro Arg Glu Gly Thr
                165                 170                 175
Arg Thr Lys Arg His Gln Lys Phe Thr His Phe Leu Pro Arg Pro Val
            180                 185                 190
Asp Pro Asp Lys Val Pro Glu Leu Tyr Lys Asp Ile Leu Ser Gln Ser
        195                 200                 205

<210> SEQ ID NO 9
<211> LENGTH: 172
<212> TYPE: PRT
<213> ORGANISM: HOMO SAPIENS
<220> FEATURE:
<221> NAME/KEY: MISC_FEATURE
<222> LOCATION: (108)..(108)
<223> OTHER INFORMATION: X is other than W and more preferably
      selected from G, R, E or V (W144X)

<400> SEQUENCE: 9

Met Gly Gln Ser Glu Ala Gly Gly Leu Pro Arg Gly Pro Ala Val Thr
1               5                   10                  15
Asp Leu Asp His Leu Lys Gly Ile Leu Arg Arg Arg Gln Leu Tyr Cys
            20                  25                  30
Arg Thr Gly Phe His Leu Glu Ile Phe Pro Asn Gly Thr Ile Gln Gly
        35                  40                  45
Thr Arg Lys Asp His Ser Arg Phe Gly Ile Leu Glu Phe Ile Ser Ile
    50                  55                  60
Ala Val Gly Leu Val Ser Ile Arg Gly Val Asp Ser Gly Leu Tyr Leu
65                  70                  75                  80
Gly Met Asn Glu Lys Gly Glu Leu Tyr Gly Ser Glu Lys Leu Thr Gln
                85                  90                  95
Glu Cys Val Phe Arg Glu Gln Phe Glu Glu Asn Xaa Tyr Asn Thr Tyr
            100                 105                 110
Ser Ser Asn Leu Tyr Lys His Val Asp Thr Gly Arg Arg Tyr Tyr Val
        115                 120                 125
Ala Leu Asn Lys Asp Gly Thr Pro Arg Glu Gly Thr Arg Thr Lys Arg
    130                 135                 140
His Gln Lys Phe Thr His Phe Leu Pro Arg Pro Val Asp Pro Asp Lys
145                 150                 155                 160
Val Pro Glu Leu Tyr Lys Asp Ile Leu Ser Gln Ser
                165                 170
```

<210> SEQ ID NO 10
<211> LENGTH: 145
<212> TYPE: PRT
<213> ORGANISM: HOMO SAPIENS

<400> SEQUENCE: 10

Met Gln Leu Tyr Cys Arg Thr Gly Phe His Leu Glu Ile Phe Pro Asn
1               5                   10                  15

Gly Thr Ile Gln Gly Thr Arg Lys Asp His Ser Arg Phe Gly Ile Leu
            20                  25                  30

Glu Phe Ile Ser Ile Ala Val Gly Leu Val Ser Ile Arg Gly Val Asp
        35                  40                  45

Ser Gly Leu Tyr Leu Gly Met Asn Glu Lys Gly Glu Leu Tyr Gly Ser
    50                  55                  60

Glu Lys Leu Thr Gln Glu Cys Val Phe Arg Glu Gln Phe Glu Glu Asn
65                  70                  75                  80

Trp Tyr Asn Thr Tyr Ser Ser Asn Leu Tyr Lys His Val Asp Thr Gly
                85                  90                  95

Arg Arg Tyr Tyr Val Ala Leu Asn Lys Asp Gly Thr Pro Arg Glu Gly
            100                 105                 110

Thr Arg Thr Lys Arg His Gln Lys Phe Thr His Phe Leu Pro Arg Pro
        115                 120                 125

Val Asp Pro Asp Lys Val Pro Glu Leu Tyr Lys Asp Ile Leu Ser Gln
    130                 135                 140

Ser
145

<210> SEQ ID NO 11
<211> LENGTH: 145
<212> TYPE: PRT
<213> ORGANISM: HOMO SAPIENS
<220> FEATURE:
<221> NAME/KEY: MISC_FEATURE
<222> LOCATION: (81)..(81)
<223> OTHER INFORMATION: X is other than W and more preferably
      selected from G, R, E or V (W144X)

<400> SEQUENCE: 11

Met Gln Leu Tyr Cys Arg Thr Gly Phe His Leu Glu Ile Phe Pro Asn
1               5                   10                  15

Gly Thr Ile Gln Gly Thr Arg Lys Asp His Ser Arg Phe Gly Ile Leu
            20                  25                  30

Glu Phe Ile Ser Ile Ala Val Gly Leu Val Ser Ile Arg Gly Val Asp
        35                  40                  45

Ser Gly Leu Tyr Leu Gly Met Asn Glu Lys Gly Glu Leu Tyr Gly Ser
    50                  55                  60

Glu Lys Leu Thr Gln Glu Cys Val Phe Arg Glu Gln Phe Glu Glu Asn
65                  70                  75                  80

Xaa Tyr Asn Thr Tyr Ser Ser Asn Leu Tyr Lys His Val Asp Thr Gly
                85                  90                  95

Arg Arg Tyr Tyr Val Ala Leu Asn Lys Asp Gly Thr Pro Arg Glu Gly
            100                 105                 110

Thr Arg Thr Lys Arg His Gln Lys Phe Thr His Phe Leu Pro Arg Pro
        115                 120                 125

Val Asp Pro Asp Lys Val Pro Glu Leu Tyr Lys Asp Ile Leu Ser Gln
    130                 135                 140

Ser

<210> SEQ ID NO 12
<211> LENGTH: 127
<212> TYPE: PRT
<213> ORGANISM: HOMO SAPIENS

<400> SEQUENCE: 12

Met Gln Leu Tyr Cys Arg Thr Gly Phe His Leu Glu Ile Phe Pro Asn
1               5                   10                  15

Gly Thr Ile Gln Gly Thr Arg Lys Asp His Ser Arg Phe Gly Ile Leu
            20                  25                  30

Glu Phe Ile Ser Ile Ala Val Gly Leu Val Ser Ile Arg Gly Val Asp
        35                  40                  45

Ser Gly Leu Tyr Leu Gly Met Asn Glu Lys Gly Glu Leu Tyr Gly Ser
    50                  55                  60

Glu Lys Leu Thr Gln Glu Cys Val Phe Arg Glu Gln Phe Glu Glu Asn
65                  70                  75                  80

Trp Tyr Asn Thr Tyr Ser Ser Asn Leu Tyr Lys His Val Asp Thr Gly
                85                  90                  95

Arg Arg Tyr Tyr Val Ala Leu Asn Lys Asp Gly Thr Pro Arg Glu Gly
            100                 105                 110

Thr Arg Thr Lys Arg His Gln Lys Phe Thr His Phe Leu Pro Arg
        115                 120                 125

<210> SEQ ID NO 13
<211> LENGTH: 127
<212> TYPE: PRT
<213> ORGANISM: HOMO SAPIENS
<220> FEATURE:
<221> NAME/KEY: MISC_FEATURE
<222> LOCATION: (81)..(81)
<223> OTHER INFORMATION: X is other than W and more preferably
      selected from G, R, E or V (W144X)

<400> SEQUENCE: 13

Met Gln Leu Tyr Cys Arg Thr Gly Phe His Leu Glu Ile Phe Pro Asn
1               5                   10                  15

Gly Thr Ile Gln Gly Thr Arg Lys Asp His Ser Arg Phe Gly Ile Leu
            20                  25                  30

Glu Phe Ile Ser Ile Ala Val Gly Leu Val Ser Ile Arg Gly Val Asp
        35                  40                  45

Ser Gly Leu Tyr Leu Gly Met Asn Glu Lys Gly Glu Leu Tyr Gly Ser
    50                  55                  60

Glu Lys Leu Thr Gln Glu Cys Val Phe Arg Glu Gln Phe Glu Glu Asn
65                  70                  75                  80

Xaa Tyr Asn Thr Tyr Ser Ser Asn Leu Tyr Lys His Val Asp Thr Gly
                85                  90                  95

Arg Arg Tyr Tyr Val Ala Leu Asn Lys Asp Gly Thr Pro Arg Glu Gly
            100                 105                 110

Thr Arg Thr Lys Arg His Gln Lys Phe Thr His Phe Leu Pro Arg
        115                 120                 125

<210> SEQ ID NO 14
<211> LENGTH: 145
<212> TYPE: PRT
<213> ORGANISM: HOMO SAPIENS
<220> FEATURE:
<221> NAME/KEY: MISC_FEATURE
<222> LOCATION: (80)..(80)
<223> OTHER INFORMATION: wherein X is other than N and more preferably

S (N143X)

<400> SEQUENCE: 14

```
Met Gln Leu Tyr Cys Arg Thr Gly Phe His Leu Glu Ile Phe Pro Asn
1               5                   10                  15

Gly Thr Ile Gln Gly Thr Arg Lys Asp His Ser Arg Phe Gly Ile Leu
            20                  25                  30

Glu Phe Ile Ser Ile Ala Val Gly Leu Val Ser Ile Arg Gly Val Asp
        35                  40                  45

Ser Gly Leu Tyr Leu Gly Met Asn Glu Lys Gly Glu Leu Tyr Gly Ser
    50                  55                  60

Glu Lys Leu Thr Gln Glu Cys Val Phe Arg Glu Gln Phe Glu Glu Xaa
65                  70                  75                  80

Trp Tyr Asn Thr Tyr Ser Ser Asn Leu Tyr Lys His Val Asp Thr Gly
                85                  90                  95

Arg Arg Tyr Tyr Val Ala Leu Asn Lys Asp Gly Thr Pro Arg Glu Gly
            100                 105                 110

Thr Arg Thr Lys Arg His Gln Lys Phe Thr His Phe Leu Pro Arg Pro
        115                 120                 125

Val Asp Pro Asp Lys Val Pro Glu Leu Tyr Lys Asp Ile Leu Ser Gln
    130                 135                 140

Ser
145
```

<210> SEQ ID NO 15
<211> LENGTH: 127
<212> TYPE: PRT
<213> ORGANISM: HOMO SAPIENS
<220> FEATURE:
<221> NAME/KEY: MISC_FEATURE
<222> LOCATION: (80)..(80)
<223> OTHER INFORMATION: wherein X is other than N and more preferably
      S (N143X).

<400> SEQUENCE: 15

```
Met Gln Leu Tyr Cys Arg Thr Gly Phe His Leu Glu Ile Phe Pro Asn
1               5                   10                  15

Gly Thr Ile Gln Gly Thr Arg Lys Asp His Ser Arg Phe Gly Ile Leu
            20                  25                  30

Glu Phe Ile Ser Ile Ala Val Gly Leu Val Ser Ile Arg Gly Val Asp
        35                  40                  45

Ser Gly Leu Tyr Leu Gly Met Asn Glu Lys Gly Glu Leu Tyr Gly Ser
    50                  55                  60

Glu Lys Leu Thr Gln Glu Cys Val Phe Arg Glu Gln Phe Glu Glu Xaa
65                  70                  75                  80

Trp Tyr Asn Thr Tyr Ser Ser Asn Leu Tyr Lys His Val Asp Thr Gly
                85                  90                  95

Arg Arg Tyr Tyr Val Ala Leu Asn Lys Asp Gly Thr Pro Arg Glu Gly
            100                 105                 110

Thr Arg Thr Lys Arg His Gln Lys Phe Thr His Phe Leu Pro Arg
        115                 120                 125
```

<210> SEQ ID NO 16
<211> LENGTH: 152
<212> TYPE: PRT
<213> ORGANISM: HOMO SAPIENS
<220> FEATURE:
<221> NAME/KEY: MISC_FEATURE
<222> LOCATION: (81)..(81)
<223> OTHER INFORMATION: X is other than W and more preferably selected from G, R, E or V (W144X)

<400> SEQUENCE: 16

Met Gln Leu Tyr Cys Arg Thr Gly Phe His Leu Glu Ile Phe Pro Asn
1               5                   10                  15

Gly Thr Ile Gln Gly Thr Arg Lys Asp His Ser Arg Phe Gly Ile Leu
            20                  25                  30

Glu Phe Ile Ser Ile Ala Val Gly Leu Val Ser Ile Arg Gly Val Asp
        35                  40                  45

Ser Gly Leu Tyr Leu Gly Met Asn Glu Lys Gly Glu Leu Tyr Gly Ser
50                  55                  60

Glu Lys Leu Thr Gln Glu Cys Val Phe Arg Glu Gln Phe Glu Glu Asn
65                  70                  75                  80

Xaa Tyr Asn Thr Tyr Ser Ser Asn Leu Tyr Lys His Val Asp Thr Gly
                85                  90                  95

Arg Arg Tyr Tyr Val Ala Leu Asn Lys Asp Gly Thr Pro Arg Glu Gly
            100                 105                 110

Thr Arg Thr Lys Arg His Gln Lys Phe Thr His Phe Leu Pro Arg Gly
        115                 120                 125

Gly Gly Gly Leu Ser Lys Gly Cys Phe Gly Leu Lys Leu Asp Arg Ile
130                 135                 140

Gly Ser Met Ser Gly Leu Gly Cys
145                 150

<210> SEQ ID NO 17
<211> LENGTH: 157
<212> TYPE: PRT
<213> ORGANISM: HOMO SAPIENS
<220> FEATURE:
<221> NAME/KEY: MISC_FEATURE
<222> LOCATION: (111)..(111)
<223> OTHER INFORMATION: X is other than W and more preferably
      selected from G, R, E or V (W144X)

<400> SEQUENCE: 17

Met Gly Leu Ser Lys Gly Cys Phe Gly Leu Lys Leu Asp Arg Ile Gly
1               5                   10                  15

Ser Met Ser Gly Leu Gly Cys Gly Gly Gly Gly Gly Gly Gly Gly Gln
            20                  25                  30

Leu Tyr Cys Arg Thr Gly Phe His Leu Glu Ile Phe Pro Asn Gly Thr
        35                  40                  45

Ile Gln Gly Thr Arg Lys Asp His Ser Arg Phe Gly Ile Leu Glu Phe
50                  55                  60

Ile Ser Ile Ala Val Gly Leu Val Ser Ile Arg Gly Val Asp Ser Gly
65                  70                  75                  80

Leu Tyr Leu Gly Met Asn Glu Lys Gly Glu Leu Tyr Gly Ser Glu Lys
                85                  90                  95

Leu Thr Gln Glu Cys Val Phe Arg Glu Gln Phe Glu Glu Asn Xaa Tyr
            100                 105                 110

Asn Thr Tyr Ser Ser Asn Leu Tyr Lys His Val Asp Thr Gly Arg Arg
        115                 120                 125

Tyr Tyr Val Ala Leu Asn Lys Asp Gly Thr Pro Arg Glu Gly Thr Arg
130                 135                 140

Thr Lys Arg His Gln Lys Phe Thr His Phe Leu Pro Arg
145                 150                 155

<210> SEQ ID NO 18
<211> LENGTH: 468

-continued

```
<212> TYPE: DNA
<213> ORGANISM: HOMO SAPIENS
<220> FEATURE:
<221> NAME/KEY: misc_feature
<222> LOCATION: (331)..(333)
<223> OTHER INFORMATION: NNN is other than a codon coding for Asn
      (AAT or AAC) or a stop codon and is more preferably a codon
      coding for amino acid Gly or Arg.

<400> SEQUENCE: 18
atggctgccg ggagcatcac cacgctgccc gcccttccgg aggatggcgg cagcggcgcc      60
ttcccgcccg ggcacttcaa ggaccccaag cggctgtact gcaaaaacgg gggcttcttc     120
ctgcgcatcc accccgacgg ccgagttgac ggggtccggg agaagagcga ccctcacatc     180
aagctacaac ttcaagcaga agagagagga gttgtgtcta tcaaaggagt gtgtgctaac     240
cggtacctgg ctatgaagga agatggaaga ttactggctt ctaaatgtgt tacggatgag     300
tgtttctttt ttgaacgatt ggaatctaat nnntacaata cttaccggtc tagaaaatac     360
accagttggt atgtggcatt gaaacgaact gggcagtata aacttggttc caaaacagga     420
cctgggcaga aagctatact ttttcttcca atgtctgcta agagctga                  468

<210> SEQ ID NO 19
<211> LENGTH: 468
<212> TYPE: DNA
<213> ORGANISM: HOMO SAPIENS
<220> FEATURE:
<221> NAME/KEY: misc_feature
<222> LOCATION: (333)..(333)
<223> OTHER INFORMATION: N IS SELECTED FROM A, C, G, T.

<400> SEQUENCE: 19
atggctgccg ggagcatcac cacgctgccc gcccttccgg aggatggcgg cagcggcgcc      60
ttcccgcccg ggcacttcaa ggaccccaag cggctgtact gcaaaaacgg gggcttcttc     120
ctgcgcatcc accccgacgg ccgagttgac ggggtccggg agaagagcga ccctcacatc     180
aagctacaac ttcaagcaga agagagagga gttgtgtcta tcaaaggagt gtgtgctaac     240
cggtacctgg ctatgaagga agatggaaga ttactggctt ctaaatgtgt tacggatgag     300
tgtttctttt ttgaacgatt ggaatctaat cgntacaata cttaccggtc tagaaaatac     360
accagttggt atgtggcatt gaaacgaact gggcagtata aacttggttc caaaacagga     420
cctgggcaga aagctatact ttttcttcca atgtctgcta agagctga                  468

<210> SEQ ID NO 20
<211> LENGTH: 468
<212> TYPE: DNA
<213> ORGANISM: HOMO SAPIENS
<220> FEATURE:
<221> NAME/KEY: misc_feature
<222> LOCATION: (331)..(333)
<223> OTHER INFORMATION: NNN is a codon coding for amino acid Arg.

<400> SEQUENCE: 20
atggctgccg ggagcatcac cacgctgccc gcccttccgg aggatggcgg cagcggcgcc      60
ttcccgcccg ggcacttcaa ggaccccaag cggctgtact gcaaaaacgg gggcttcttc     120
ctgcgcatcc accccgacgg ccgagttgac ggggtccggg agaagagcga ccctcacatc     180
aagctacaac ttcaagcaga agagagagga gttgtgtcta tcaaaggagt gtgtgctaac     240
cggtacctgg ctatgaagga agatggaaga ttactggctt ctaaatgtgt tacggatgag     300
tgtttctttt ttgaacgatt ggaatctaat nnntacaata cttaccggtc tagaaaatac     360
accagttggt atgtggcatt gaaacgaact gggcagtata aacttggttc caaaacagga     420
```
cctgggcaga aagctatact ttttcttcca atgtctgcta agagctga            468

<210> SEQ ID NO 21
<211> LENGTH: 468
<212> TYPE: DNA
<213> ORGANISM: HOMO SAPIENS
<220> FEATURE:
<221> NAME/KEY: misc_feature
<222> LOCATION: (9)..(9)
<223> OTHER INFORMATION: N IS EITHER A OR G
<220> FEATURE:
<221> NAME/KEY: misc_feature
<222> LOCATION: (15)..(15)
<223> OTHER INFORMATION: N IS EITHER A OR G
<220> FEATURE:
<221> NAME/KEY: misc_feature
<222> LOCATION: (331)..(333)
<223> OTHER INFORMATION: NNN is other than a codon coding for Asn
      (AAT or AAC) or a stop c odon and is more preferably a codon
      coding for amino acid Gly or Arg.

<400> SEQUENCE: 21
atggctcang gcanatcac cacgctgccc gcccttccgg aggatggcgg cagcggcgcc    60
ttcccgcccg ggcacttcaa ggaccccaag cggctgtact gcaaaaacgg gggcttcttc   120
ctgcgcatcc accccgacgg ccgagttgac ggggtccggg agaagagcga ccctcacatc   180
aagctacaac ttcaagcaga agagagagga gttgtgtcta tcaaaggagt gtgtgctaac   240
cggtacctgg ctatgaagga agatggaaga ttactggctt ctaaatgtgt tacggatgag   300
tgtttctttt ttgaacgatt ggaatctaat nnntacaata cttaccggtc tagaaaatac   360
accagttggt atgtggcatt gaaacgaact gggcagtata aacttggttc caaaacagga   420
cctgggcaga aagctatact ttttcttcca atgtctgcta agagctga              468

<210> SEQ ID NO 22
<211> LENGTH: 468
<212> TYPE: DNA
<213> ORGANISM: HOMO SAPIENS
<220> FEATURE:
<221> NAME/KEY: misc_feature
<222> LOCATION: (9)..(9)
<223> OTHER INFORMATION: N IS EITHER A OR G
<220> FEATURE:
<221> NAME/KEY: misc_feature
<222> LOCATION: (15)..(15)
<223> OTHER INFORMATION: N IS EITHER A OR G
<220> FEATURE:
<221> NAME/KEY: misc_feature
<222> LOCATION: (333)..(333)
<223> OTHER INFORMATION: N IS EITHER A, C, G, OR T

<400> SEQUENCE: 22
atggctcang gcanatcac cacgctgccc gcccttccgg aggatggcgg cagcggcgcc    60
ttcccgcccg ggcacttcaa ggaccccaag cggctgtact gcaaaaacgg gggcttcttc   120
ctgcgcatcc accccgacgg ccgagttgac ggggtccggg agaagagcga ccctcacatc   180
aagctacaac ttcaagcaga agagagagga gttgtgtcta tcaaaggagt gtgtgctaac   240
cggtacctgg ctatgaagga agatggaaga ttactggctt ctaaatgtgt tacggatgag   300
tgtttctttt ttgaacgatt ggaatctaat ggntacaata cttaccggtc tagaaaatac   360
accagttggt atgtggcatt gaaacgaact gggcagtata aacttggttc caaaacagga   420
cctgggcaga aagctatact ttttcttcca atgtctgcta agagctga              468

<210> SEQ ID NO 23
<211> LENGTH: 618

```
<212> TYPE: DNA
<213> ORGANISM: HOMO SAPIENS
<220> FEATURE:
<221> NAME/KEY: misc_feature
<222> LOCATION: (493)..(495)
<223> OTHER INFORMATION: NNN is other than a codon coding for Asn (AAT
      or AAC) or a stop c odon and is more preferably a codon coding
      for amino acid Gly or Arg.

<400> SEQUENCE: 23
atgtcggggc cgggacggc cgcggtagcg ctgctcccgg cggtcctgct ggccttgctg      60
gcgccctggg cgggccgagg gggcgccgcc gcacccactg cacccaacgg cacgctggag    120
gccgagctgg agcgccgctg ggagagcctg gtggcgctct cgttggcgcg cctgccggtg    180
gcagcgcagc ccaaggaggc ggccgtccag agcggcgccg cgactacct gctgggcatc     240 aagcggctgc ggcggctcta ctgcaacgtg gcatcggct tccacctcca ggcgctcccc     300
gacggccgca tcggcggcgc gcacgcggac cccgcgaca gcctgctgga gctctcgccc    360
gtggagcggg gcgtggtgag catcttcggc gtggccagcc ggttcttcgt ggccatgagc   420
agcaagggca agctctatgg ctcgcccttc ttcaccgatg agtgcacgtt caaggagatt   480
ctccttccca cnnntacaa cgcctacgag tcctacaagt accccggcat gttcatcgcc    540
ctgagcaaga atgggaagac caagaagggg aaccgagtgt cgcccaccat gaaggtcacc   600
cacttcctcc ccaggctg                                                 618

<210> SEQ ID NO 24
<211> LENGTH: 456
<212> TYPE: DNA
<213> ORGANISM: HOMO SAPIENS
<220> FEATURE:
<221> NAME/KEY: misc_feature
<222> LOCATION: (331)..(333)
<223> OTHER INFORMATION: NNN is other than a codon coding for Asn (AAT
      or AAC) or a stop codon and is more preferably a codon coding
      for amino acid Gly or Arg.

<400> SEQUENCE: 24
atggcgcgcc tgccggtggc agcgcagccc aaggaggcgg ccgtccagag cggcgccggc     60
gactacctgc tgggcatcaa gcggctgcgg cggctctact gcaacgtggg catcggcttc   120
cacctccagg cgctcccga cggccgcatc ggccggcgcg acgcggacac ccgcgacagc    180
ctgctggagc tctcgcccgt ggagcgggc gtggtgagca tcttcggcgt ggccagccgg    240
ttcttcgtgg ccatgagcag caagggcaag ctctatggct cgcccttctt caccgatgag   300
tgcacgttca aggagattct ccttcccaac nnntacaacg cctacgagtc ctacaagtac   360
cccggcatgt tcatcgccct gagcaagaat gggaagacca agaaggggaa ccgagtgtcg   420
cccaccatga aggtcaccca cttcctcccc aggctg                             456

<210> SEQ ID NO 25
<211> LENGTH: 438
<212> TYPE: DNA
<213> ORGANISM: HOMO SAPIENS

<400> SEQUENCE: 25
atgcagctat actgcaggac tggatttcac ttagaaatct tccccaatgg tactatccag     60
ggaaccagga aagaccacag ccgatttggc attctggaat ttatcagtat agcagtgggc   120
ctggtcagca ttcgaggcgt ggacagtgga ctctacctcg ggatgaatga aaggggggag   180
ctgtatggat cagaaaaact aacccaagag tgtgtattca gaacagtt cgaagaaaac    240 tggtataata cgtactcgtc aaacctatat aagcacgtgg acactggaag gcgatactat   300
```

```
gttgcattaa ataaagatgg accccgaga agggacta ggactaaacg gcaccagaaa       360
ttcacacatt ttttacctag accagtggac cccgacaaag tacctgaact gtataaggat    420
attctaagcc aaagttga                                                  438
```

<210> SEQ ID NO 26
<211> LENGTH: 438
<212> TYPE: DNA
<213> ORGANISM: HOMO SAPIENS
<220> FEATURE:
<221> NAME/KEY: misc_feature
<222> LOCATION: (241)..(243)
<223> OTHER INFORMATION: NNN is other than a codon coding for Trp (TGG)
      or a stop codon (TAA, TAG or TGA) and is more preferably a
      codon coding for amino acid Gly, Arg, Val or Glu.

<400> SEQUENCE: 26

```
atgcagctat actgcaggac tggatttcac ttagaaatct tccccaatgg tactatccag    60
ggaaccagga aagaccacag ccgatttggc attctggaat ttatcagtat agcagtgggc    120
ctggtcagca ttcgaggcgt ggacagtgga ctctacctcg ggatgaatga aaggggggag    180
ctgtatggat cagaaaaact aacccaagag tgtgtattca gagaacagtt cgaagaaaac    240
nnntataata cgtactcgtc aaacctatat aagcacgtgg acactggaag gcgatactat    300
gttgcattaa ataaagatgg accccgaga agggacta ggactaaacg gcaccagaaa       360
ttcacacatt ttttacctag accagtggac cccgacaaag tacctgaact gtataaggat    420
attctaagcc aaagttga                                                  438
```

<210> SEQ ID NO 27
<211> LENGTH: 384
<212> TYPE: DNA
<213> ORGANISM: HOMO SAPIENS

<400> SEQUENCE: 27

```
atgcagctat actgcaggac tggatttcac ttagaaatct tccccaatgg tactatccag    60
ggaaccagga aagaccacag ccgatttggc attctggaat ttatcagtat agcagtgggc    120
ctggtcagca ttcgaggcgt ggacagtgga ctctacctcg ggatgaatga aaggggggag    180
ctgtatggat cagaaaaact aacccaagag tgtgtattca gagaacagtt cgaagaaaac    240
tggtataata cgtactcgtc aaacctatat aagcacgtgg acactggaag gcgatactat    300
gttgcattaa ataaagatgg accccgaga agggacta ggactaaacg gcaccagaaa       360
ttcacacatt ttttacctag atga                                           384
```

<210> SEQ ID NO 28
<211> LENGTH: 384
<212> TYPE: DNA
<213> ORGANISM: HOMO SAPIENS
<220> FEATURE:
<221> NAME/KEY: misc_feature
<222> LOCATION: (241)..(243)
<223> OTHER INFORMATION: NNN is other than a codon coding for Trp (TGG)
      or a stop codon (TAA, TAG or TGA) and is more preferably a codon
      coding for amino acid Gly, Arg, Val or Glu.

<400> SEQUENCE: 28

```
atgcagctat actgcaggac tggatttcac ttagaaatct tccccaatgg tactatccag    60
ggaaccagga aagaccacag ccgatttggc attctggaat ttatcagtat agcagtgggc    120
ctggtcagca ttcgaggcgt ggacagtgga ctctacctcg ggatgaatga aaggggggag    180
ctgtatggat cagaaaaact aacccaagag tgtgtattca gagaacagtt cgaagaaaac    240
```

```
nnntataata cgtactcgtc aaacctatat aagcacgtgg acactggaag gcgatactat    300
gttgcattaa ataaagatgg daccccgaga aagggacta ggactaaacg gcaccagaaa     360
ttcacacatt ttttacctag atga                                          384
```

```
<210> SEQ ID NO 29
<211> LENGTH: 437
<212> TYPE: DNA
<213> ORGANISM: HOMO SAPIENS
<220> FEATURE:
<221> NAME/KEY: misc_feature
<222> LOCATION: (238)..(240)
<223> OTHER INFORMATION: wherein NNN is other than a codon coding for
      Asn (AAT, AAC) or a stop codon (TAA, TAG or TGA) and is more
      preferably a codon coding for amino acid Ser.

<400> SEQUENCE: 29
```

```
atgcagctat actgcaggac tggatttcac ttagaaatct tccccaatgg tactatccag    60
ggaaccagga aagaccacag ccgatttggc attctggaat ttatcagtat agcagtgggc    120
ctggtcagca ttcgaggcgt ggacagtgga ctctacctcg ggatgaatga aaggggggag   180
ctgtatggat cagaaaaact aacccaagag tgtgtattca gagaacagtt cgaagaannn    240
tggtataata cgtactcgtc aaacctatat aagcacgtgg acactggaag gcgatactat    300
gttgcattaa ataaagatgg daccccgaga aagggacta ggactaaacg gcaccagaaa    360
ttcacacatt ttttaccaga ccagtggacc ccgacaaagt acctgaactg tataaggata    420
ttctaagcca aagttga                                                  437
```

```
<210> SEQ ID NO 30
<211> LENGTH: 384
<212> TYPE: DNA
<213> ORGANISM: HOMO SAPIENS
<220> FEATURE:
<221> NAME/KEY: misc_feature
<222> LOCATION: (238)..(240)
<223> OTHER INFORMATION: NNN is other than a codon coding for Asn (AAT,
      AAC) or a stop codon (TAA, TAG or TGA) and is more preferably a
      codon coding for amino acid Ser.
<220> FEATURE:
<221> NAME/KEY: misc_feature
<222> LOCATION: (238)..(240)
<223> OTHER INFORMATION: NNN is other than a codon coding for Asn (AAT,
      AAC) or a stop codon (TAA, TAG or TGA) and is more preferably a
      codon coding for amino acid Ser.

<400> SEQUENCE: 30
```

```
atgcagctat actgcaggac tggatttcac ttagaaatct tccccaatgg tactatccag    60
ggaaccagga aagaccacag ccgatttggc attctggaat ttatcagtat agcagtgggc    120
ctggtcagca ttcgaggcgt ggacagtgga ctctacctcg ggatgaatga aaggggggag   180
ctgtatggat cagaaaaact aacccaagag tgtgtattca gagaacagtt cgaagaannn    240
tggtataata cgtactcgtc aaacctatat aagcacgtgg acactggaag gcgatactat    300
gttgcattaa ataaagatgg daccccgaga aagggacta ggactaaacg gcaccagaaa    360
ttcacacatt ttttacctag atga                                          384
```

```
<210> SEQ ID NO 31
<211> LENGTH: 456
<212> TYPE: DNA
<213> ORGANISM: HOMO SAPIENS
<220> FEATURE:
<221> NAME/KEY: misc_feature
<222> LOCATION: (241)..(243)
<223> OTHER INFORMATION: NNN is other than a codon coding for Trp (TGG)
``` or a stop codon (TAA, TAG or TGA) and is more preferably a codon
coding for amino acid Gly, Arg, Val or Glu.

<400> SEQUENCE: 31

```
atgcagctat actgcaggac tggatttcac ttagaaatct tccccaatgg tactatccag      60
ggaaccagga aagaccacag ccgatttggc attctggaat ttatcagtat agcagtgggc     120
ctggtcagca ttcgaggcgt ggacagtgga ctctacctcg ggatgaatga aaggggggag     180
ctgtatggat cagaaaaact aacccaagag tgtgtattca gagaacagtt cgaagaaaac     240
nnntataata cgtactcgtc aaacctatat aagcacgtgg acactggaag gcgatactat     300
gttgcattaa ataaagatgg accccgaga  aagggactac ggactaaacg gcaccagaaa    360
ttcacacatt ttttacctag aggaggggga ggtctgtcca aggttgcttc ggcctcaag     420
ctggaccgaa tcggctccat gagcggcctg ggatgt                                456
```

<210> SEQ ID NO 32
<211> LENGTH: 471
<212> TYPE: DNA
<213> ORGANISM: HOMO SAPIENS
<220> FEATURE:
<221> NAME/KEY: misc_feature
<222> LOCATION: (331)..(333)
<223> OTHER INFORMATION: NNN is other than a codon coding for Trp (TGG)
or a stop codon (TAA, TAG or TGA) and is more preferably a codon
coding for amino acid Gly, Arg, Val or Glu.

<400> SEQUENCE: 32

```
atgggtctgt ccaaaggttg cttcggcctc aagctggacc gaatcggctc catgagcggc      60
ctgggatgcg aggggggagg gggaggggga gggcagctat actgcaggac tggatttcac     120
ttagaaatct tccccaatgg tactatccag ggaaccagga aagaccacag ccgatttggc     180
attctggaat ttatcagtat agcagtgggc ctggtcagca ttcgaggcgt ggacagtgga     240
ctctacctcg ggatgaatga aaggggggag ctgtatggat cagaaaaact aacccaagag     300
tgtgtattca gagaacagtt cgaagaaaac nnntataata cgtactcgtc aaacctatat     360
aagcacgtgg acactggaag gcgatactat gttgcattaa ataaagatgg accccgaga     420
aagggactac ggactaaacg gcaccagaaa ttcacacatt ttttacctag a               471
```

<210> SEQ ID NO 33
<211> LENGTH: 9
<212> TYPE: PRT
<213> ORGANISM: HOMO SAPIENS

<400> SEQUENCE: 33

Leu Glu Glu Asn His Tyr Asn Thr Tyr
1               5

<210> SEQ ID NO 34
<211> LENGTH: 9
<212> TYPE: PRT
<213> ORGANISM: HOMO SAPIENS

<400> SEQUENCE: 34

Leu Glu Ser Asn Asn Tyr Asn Thr Tyr
1               5

<210> SEQ ID NO 35
<211> LENGTH: 9
<212> TYPE: PRT
<213> ORGANISM: HOMO SAPIENS

<400> SEQUENCE: 35

```
Ile His Glu Leu Gly Tyr Asn Thr Tyr
1               5

<210> SEQ ID NO 36
<211> LENGTH: 9
<212> TYPE: PRT
<213> ORGANISM: HOMO SAPIENS

<400> SEQUENCE: 36

Leu Leu Pro Asn Asn Tyr Asn Ala Tyr
1               5

<210> SEQ ID NO 37
<211> LENGTH: 9
<212> TYPE: PRT
<213> ORGANISM: HOMO SAPIENS

<400> SEQUENCE: 37

Phe Gln Glu Asn Ser Tyr Asn Thr Tyr
1               5

<210> SEQ ID NO 38
<211> LENGTH: 9
<212> TYPE: PRT
<213> ORGANISM: HOMO SAPIENS

<400> SEQUENCE: 38

Leu Leu Pro Asn Asn Tyr Asn Thr Tyr
1               5

<210> SEQ ID NO 39
<211> LENGTH: 9
<212> TYPE: PRT
<213> ORGANISM: HOMO SAPIENS

<400> SEQUENCE: 39

Ile Leu Glu Asn His Tyr Asn Thr Tyr
1               5

<210> SEQ ID NO 40
<211> LENGTH: 9
<212> TYPE: PRT
<213> ORGANISM: HOMO SAPIENS

<400> SEQUENCE: 40

Val Leu Glu Asn Asn Tyr Thr Ala Leu
1               5

<210> SEQ ID NO 41
<211> LENGTH: 9
<212> TYPE: PRT
<213> ORGANISM: HOMO SAPIENS

<400> SEQUENCE: 41

Phe Glu Glu Asn Trp Tyr Asn Thr Tyr
1               5

<210> SEQ ID NO 42
<211> LENGTH: 9
<212> TYPE: PRT
<213> ORGANISM: HOMO SAPIENS

<400> SEQUENCE: 42

Ile Glu Glu Asn Gly Tyr Asn Thr Tyr
1               5
```

```
<210> SEQ ID NO 43
<211> LENGTH: 9
<212> TYPE: PRT
<213> ORGANISM: HOMO SAPIENS

<400> SEQUENCE: 43

Val Phe Glu Asn Tyr Tyr Val Leu Tyr
1               5

<210> SEQ ID NO 44
<211> LENGTH: 9
<212> TYPE: PRT
<213> ORGANISM: HOMO SAPIENS

<400> SEQUENCE: 44

Val Phe Glu Asn Tyr Tyr Val Ile Tyr
1               5

<210> SEQ ID NO 45
<211> LENGTH: 9
<212> TYPE: PRT
<213> ORGANISM: HOMO SAPIENS

<400> SEQUENCE: 45

Val Phe Glu Asn Tyr Tyr Val Thr Tyr
1               5

<210> SEQ ID NO 46
<211> LENGTH: 9
<212> TYPE: PRT
<213> ORGANISM: HOMO SAPIENS

<400> SEQUENCE: 46

Val Phe Glu Asn Tyr Tyr Val Ile Tyr
1               5

<210> SEQ ID NO 47
<211> LENGTH: 9
<212> TYPE: PRT
<213> ORGANISM: HOMO SAPIENS

<400> SEQUENCE: 47

Met Asp Cys Leu Gly Tyr Asn Gln Tyr
1               5

<210> SEQ ID NO 48
<211> LENGTH: 9
<212> TYPE: PRT
<213> ORGANISM: HOMO SAPIENS

<400> SEQUENCE: 48

Phe Glu Glu Asn Trp Tyr Asn Thr Tyr
1               5

<210> SEQ ID NO 49
<211> LENGTH: 9
<212> TYPE: PRT
<213> ORGANISM: HOMO SAPIENS

<400> SEQUENCE: 49

Val Leu Glu Asn Asn Tyr Thr Ala Phe
1               5

<210> SEQ ID NO 50
```

```
<211> LENGTH: 9
<212> TYPE: PRT
<213> ORGANISM: HOMO SAPIENS

<400> SEQUENCE: 50

Val Leu Glu Asn Asn Tyr Thr Ala Leu
1               5

<210> SEQ ID NO 51
<211> LENGTH: 9
<212> TYPE: PRT
<213> ORGANISM: HOMO SAPIENS

<400> SEQUENCE: 51

Ile Arg Pro Asp Gly Tyr Asn Val Tyr
1               5

<210> SEQ ID NO 52
<211> LENGTH: 9
<212> TYPE: PRT
<213> ORGANISM: HOMO SAPIENS

<400> SEQUENCE: 52

Phe Glu Glu Asn Trp Tyr Asn Thr Tyr
1               5

<210> SEQ ID NO 53
<211> LENGTH: 9
<212> TYPE: PRT
<213> ORGANISM: HOMO SAPIENS

<400> SEQUENCE: 53

Leu Leu Glu Asp Gly Tyr Asn Val Tyr
1               5

<210> SEQ ID NO 54
<211> LENGTH: 9
<212> TYPE: PRT
<213> ORGANISM: HOMO SAPIENS

<400> SEQUENCE: 54

Ile Glu Glu Asn Gly His Asn Thr Tyr
1               5

<210> SEQ ID NO 55
<211> LENGTH: 9
<212> TYPE: PRT
<213> ORGANISM: HOMO SAPIENS

<400> SEQUENCE: 55

Thr Leu Glu Asn Gly Tyr Asp Val Tyr
1               5

<210> SEQ ID NO 56
<211> LENGTH: 9
<212> TYPE: PRT
<213> ORGANISM: HOMO SAPIENS

<400> SEQUENCE: 56

Phe Glu Glu Asn Trp Tyr Asn Thr Tyr
1               5

<210> SEQ ID NO 57
<211> LENGTH: 9
<212> TYPE: PRT
<213> ORGANISM: HOMO SAPIENS
```

```
<400> SEQUENCE: 57

Leu Leu Glu Asp Gly Tyr Asn Val Tyr
1               5

<210> SEQ ID NO 58
<211> LENGTH: 28
<212> TYPE: DNA
<213> ORGANISM: Artificial Sequence
<220> FEATURE:
<223> OTHER INFORMATION: artificial primer

<400> SEQUENCE: 58
ggaattccat atggctgaag gggaaatc                                     28

<210> SEQ ID NO 59
<211> LENGTH: 22
<212> TYPE: DNA
<213> ORGANISM: Artificial Sequence
<220> FEATURE:
<223> OTHER INFORMATION: artificial primer

<400> SEQUENCE: 59
cgggatcctc agctcttagc ag                                           22

<210> SEQ ID NO 60
<211> LENGTH: 29
<212> TYPE: DNA
<213> ORGANISM: Artificial Sequence
<220> FEATURE:
<223> OTHER INFORMATION: artificial primer

<400> SEQUENCE: 60
gattggaatc taatggctac aatacttac                                    29

<210> SEQ ID NO 61
<211> LENGTH: 29
<212> TYPE: DNA
<213> ORGANISM: Artificial Sequence
<220> FEATURE:
<223> OTHER INFORMATION: artificial primer

<400> SEQUENCE: 61
gtaagtattg tagccattag attccaatc                                    29

<210> SEQ ID NO 62
<211> LENGTH: 29
<212> TYPE: DNA
<213> ORGANISM: Artificial Sequence
<220> FEATURE:
<223> OTHER INFORMATION: artificial primer

<400> SEQUENCE: 62
gattggaatc taatcgctac aatacttac                                    29

<210> SEQ ID NO 63
<211> LENGTH: 29
<212> TYPE: DNA
<213> ORGANISM: Artificial Sequence
<220> FEATURE:
<223> OTHER INFORMATION: artificial primer

<400> SEQUENCE: 63
gtaagtattg tagcgattag attccaatc                                    29

<210> SEQ ID NO 64
```

```
<211> LENGTH: 37
<212> TYPE: DNA
<213> ORGANISM: Artificial Sequence
<220> FEATURE:
<223> OTHER INFORMATION: artificial primer

<400> SEQUENCE: 64
ggaattccat atggctcaag ggcaaatcac cacgctg                              37

<210> SEQ ID NO 65
<211> LENGTH: 25
<212> TYPE: DNA
<213> ORGANISM: Artificial Sequence
<220> FEATURE:
<223> OTHER INFORMATION: artificial primer

<400> SEQUENCE: 65
cgaagaaaac gggtataata cgtac                                          25

<210> SEQ ID NO 66
<211> LENGTH: 25
<212> TYPE: DNA
<213> ORGANISM: Artificial Sequence
<220> FEATURE:
<223> OTHER INFORMATION: artificial primer

<400> SEQUENCE: 66
gtacgtatta tacccgtttt cttcg                                          25

<210> SEQ ID NO 67
<211> LENGTH: 22
<212> TYPE: DNA
<213> ORGANISM: Artificial Sequence
<220> FEATURE:
<223> OTHER INFORMATION: artificial primer

<400> SEQUENCE: 67
cgaagaaaac cggtataata cg                                             22

<210> SEQ ID NO 68
<211> LENGTH: 22
<212> TYPE: DNA
<213> ORGANISM: Artificial Sequence
<220> FEATURE:
<223> OTHER INFORMATION: artificial primer

<400> SEQUENCE: 68
cgtattatac cggttttctt cg                                             22

<210> SEQ ID NO 69
<211> LENGTH: 22
<212> TYPE: DNA
<213> ORGANISM: Artificial Sequence
<220> FEATURE:
<223> OTHER INFORMATION: artificial primer

<400> SEQUENCE: 69
cgaagaaaac gtgtataata cg                                             22

<210> SEQ ID NO 70
<211> LENGTH: 22
<212> TYPE: DNA
<213> ORGANISM: Artificial Sequence
<220> FEATURE:
<223> OTHER INFORMATION: artificial primer

<400> SEQUENCE: 70
```
cgtattatac acgttttctt cg                                         22

<210> SEQ ID NO 71
<211> LENGTH: 22
<212> TYPE: DNA
<213> ORGANISM: Artificial Sequence
<220> FEATURE:
<223> OTHER INFORMATION: artificial primer

<400> SEQUENCE: 71
cgaagaaaac gagtataata cg                                         22

<210> SEQ ID NO 72
<211> LENGTH: 22
<212> TYPE: DNA
<213> ORGANISM: Artificial Sequence
<220> FEATURE:
<223> OTHER INFORMATION: artificial primer

<400> SEQUENCE: 72
cgtattatac tcgttttctt cg                                         22

<210> SEQ ID NO 73
<211> LENGTH: 22
<212> TYPE: DNA
<213> ORGANISM: Artificial Sequence
<220> FEATURE:
<223> OTHER INFORMATION: artificial primer

<400> SEQUENCE: 73
cgaagaaaac gcgtataata cg                                         22

<210> SEQ ID NO 74
<211> LENGTH: 22
<212> TYPE: DNA
<213> ORGANISM: Artificial Sequence
<220> FEATURE:
<223> OTHER INFORMATION: artificial primer

<400> SEQUENCE: 74
cgtattatac gcgttttctt cg                                         22

<210> SEQ ID NO 75
<211> LENGTH: 22
<212> TYPE: DNA
<213> ORGANISM: Artificial Sequence
<220> FEATURE:
<223> OTHER INFORMATION: artificial primer

<400> SEQUENCE: 75
cgaagaaaac aattataata cg                                         22

<210> SEQ ID NO 76
<211> LENGTH: 22
<212> TYPE: DNA
<213> ORGANISM: Artificial Sequence
<220> FEATURE:
<223> OTHER INFORMATION: artificial primer

<400> SEQUENCE: 76
cgtattataa ttgttttctt cg                                         22

<210> SEQ ID NO 77
<211> LENGTH: 32
<212> TYPE: DNA
<213> ORGANISM: Artificial Sequence
<220> FEATURE:

```
<223> OTHER INFORMATION: artificial primer

<400> SEQUENCE: 77
agctggatcc tcaactttgg cttagaatat cc                              32

<210> SEQ ID NO 78
<211> LENGTH: 33
<212> TYPE: DNA
<213> ORGANISM: Artificial Sequence
<220> FEATURE:
<223> OTHER INFORMATION: artificial primer

<400> SEQUENCE: 78
gggaattcca tatgcagcta tactgcagga ctg                             33

<210> SEQ ID NO 79
<211> LENGTH: 27
<212> TYPE: DNA
<213> ORGANISM: Artificial Sequence
<220> FEATURE:
<223> OTHER INFORMATION: artificial primer

<400> SEQUENCE: 79
gttcgaagaa agctggtata atatacg                                    27

<210> SEQ ID NO 80
<211> LENGTH: 25
<212> TYPE: DNA
<213> ORGANISM: Artificial Sequence
<220> FEATURE:
<223> OTHER INFORMATION: artificial primer

<400> SEQUENCE: 80
cgtattatac cagctttctt cgaac                                      25

<210> SEQ ID NO 81
<211> LENGTH: 28
<212> TYPE: DNA
<213> ORGANISM: Artificial Sequence
<220> FEATURE:
<223> OTHER INFORMATION: artificial primer

<400> SEQUENCE: 81
acgtcatatg ttggcgcgcc tgccggtg                                   28

<210> SEQ ID NO 82
<211> LENGTH: 29
<212> TYPE: DNA
<213> ORGANISM: Artificial Sequence
<220> FEATURE:
<223> OTHER INFORMATION: artificial primer

<400> SEQUENCE: 82
acgtggatcc tcacagcctg gggaggaag                                  29

<210> SEQ ID NO 83
<211> LENGTH: 34
<212> TYPE: DNA
<213> ORGANISM: Artificial Sequence
<220> FEATURE:
<223> OTHER INFORMATION: artificial primer

<400> SEQUENCE: 83
gattctcctt cccaacaggt acaacgccta cgag                            34

<210> SEQ ID NO 84
```

```
<211> LENGTH: 34
<212> TYPE: DNA
<213> ORGANISM: Artificial Sequence
<220> FEATURE:
<223> OTHER INFORMATION: artificial primer

<400> SEQUENCE: 84
ctcgtaggcg ttgtacctgt tgggaaggag aatc                              34

<210> SEQ ID NO 85
<211> LENGTH: 31
<212> TYPE: DNA
<213> ORGANISM: Artificial Sequence
<220> FEATURE:
<223> OTHER INFORMATION: artificial primer

<400> SEQUENCE: 85
ggccctaggt catctaggta aaaaatgtgt g                                 31

<210> SEQ ID NO 86
<211> LENGTH: 33
<212> TYPE: DNA
<213> ORGANISM: Artificial Sequence
<220> FEATURE:
<223> OTHER INFORMATION: artificial primer

<400> SEQUENCE: 86
gggaattcca tatgcagcta tactgcagga ctg                               33

<210> SEQ ID NO 87
<211> LENGTH: 32
<212> TYPE: DNA
<213> ORGANISM: Artificial Sequence
<220> FEATURE:
<223> OTHER INFORMATION: artificial primer

<400> SEQUENCE: 87
agctggatcc tcaactttgg cttagaatat cc                                32

<210> SEQ ID NO 88
<211> LENGTH: 30
<212> TYPE: DNA
<213> ORGANISM: Artificial Sequence
<220> FEATURE:
<223> OTHER INFORMATION: artificial primer

<400> SEQUENCE: 88
cgatacgtac atatgcactt agaaatcttc                                   30

<210> SEQ ID NO 89
<211> LENGTH: 33
<212> TYPE: DNA
<213> ORGANISM: Artificial Sequence
<220> FEATURE:
<223> OTHER INFORMATION: artificial primer

<400> SEQUENCE: 89
gggaattcca tatgcagcta tactgcagga ctg                               33

<210> SEQ ID NO 90
<211> LENGTH: 32
<212> TYPE: DNA
<213> ORGANISM: Artificial Sequence
<220> FEATURE:
<223> OTHER INFORMATION: artificial primer

<400> SEQUENCE: 90
```
agctggatcc tcagcaaccc agaccggaca tg                      32

<210> SEQ ID NO 91
<211> LENGTH: 46
<212> TYPE: DNA
<213> ORGANISM: Artificial Sequence
<220> FEATURE:
<223> OTHER INFORMATION: artificial primer

<400> SEQUENCE: 91
cacacatttt ttacctagag gagggggagg tctgtccaaa ggttgc       46

<210> SEQ ID NO 92
<211> LENGTH: 46
<212> TYPE: DNA
<213> ORGANISM: Artificial Sequence
<220> FEATURE:
<223> OTHER INFORMATION: artificial primer

<400> SEQUENCE: 92
gcaacctttg gacagacctc ccctcctct aggtaaaaaa tgtgtg        46

<210> SEQ ID NO 93
<211> LENGTH: 30
<212> TYPE: DNA
<213> ORGANISM: Artificial Sequence
<220> FEATURE:
<223> OTHER INFORMATION: artificial primer

<400> SEQUENCE: 93
acgtgaccat atgggtctgt ccaaaggttg                         30

<210> SEQ ID NO 94
<211> LENGTH: 62
<212> TYPE: DNA
<213> ORGANISM: Artificial Sequence
<220> FEATURE:
<223> OTHER INFORMATION: artificial primer

<400> SEQUENCE: 94
cagtcctgca gtatagctgc cctccccctc ccctccccc tccgcaaccc agaccggaca   60
tg                                                                62

<210> SEQ ID NO 95
<211> LENGTH: 61
<212> TYPE: DNA
<213> ORGANISM: Artificial Sequence
<220> FEATURE:
<223> OTHER INFORMATION: artificial primer

<400> SEQUENCE: 95
atgtccggtc tgggttgcgg aggggggagg ggagggggag ggcagctata ctgcaggact  60
g                                                                 61

<210> SEQ ID NO 96
<211> LENGTH: 31
<212> TYPE: DNA
<213> ORGANISM: Artificial Sequence
<220> FEATURE:
<223> OTHER INFORMATION: artificial primer

<400> SEQUENCE: 96
ggccctaggt catctaggta aaaaatgtgt g                       31

FGF VARIANTS AND METHODS FOR USE THEREOF

CROSS-REFERENCE TO RELATED APPLICATIONS

This application is a continuation of U.S. application Ser. No. 10/982,514 filed Nov. 5, 2004 now U.S. Pat. No. 7,563,769, which is a continuation of International application PCT/IL03/00379 filed May 9, 2003, the entire content of each of which is expressly incorporated herein by reference.

FIELD OF THE INVENTION

The present invention concerns mutants and variants of fibroblast growth factors (FGFS) with improved properties, and provides FGF polypeptides, pharmaceutical compositions comprising these variants and methods for use thereof.

BACKGROUND OF THE INVENTION

Fibroblast Growth Factors and their Receptors Fibroblast growth factors (FGFS) comprise a large family of evolutionarily conserved polypeptides involved in a variety of biological processes including morphogenesis, angiogenesis, and tissue remodeling as well as in the pathogenesis of numerous diseases (reviewed in ORNITZ, Bioessays 22, 108, 2000). The various members of this family stimulate the proliferation of a wide spectrum of cells, ranging from mesenchymal to epithelial and neuroectodermal origin in vitro and IIZ vivo. FGFs are expressed in a strict temporal and spatial pattern during development and have important roles in patterning and limb formation (reviewed in ORNITZ, Bioessays 22, 108, 2000).

FGFs are powerful mitogens and are critical in the regulation of many biological processes including angiogenesis, vasculogenesis, wound healing, limb formation, tumorigenesis and cell survival. The biological response of cells to FGF is mediated through specific, high affinity (Kd 20-500 pM) cell surface receptors that possess intrinsic tyrosine kinase activity and are phosphorylated upon binding of FGF (Coughlin et al. J. Biol. Chem. 263, 988, 1988). Five distinct Fibroblast Growth Factor Receptors (FGFRs) have been identified, FGFR1-4 are transmembrane-protein kinases while FGFR5 appears to be a soluble receptor. The FGFR extracellular domain consists of three immunoglobulin-like (Ig-like) domains (D1, D2 and D3), a heparin binding domain and an acidic box. Alternative splicing of the FGFR mRNAs generates different receptor variants, including the FGFR3IIIB and FGFR3IIIC forms, each having unique ligand specificity.

Another critically functional component in receptor activation is the binding to proteoglycans such as heparan sulfate. FGFs fail to bind and activate FGF receptors in cells deprived of endogenous heparan sulfate. Different models have been proposed to explain the role of heparan sulfate proteoglycans (HSPG) in FGF signaling, including the formation of a functional tertiary complex between FGF, FGFR and an HSPG (Yayon et al., Cell 64, 841, 1991; Faham et al, Curr. Opin. Struct. Biol. 8: 578, 1998).

Bone Development

The process of bone formation is initiated by endochondral ossification and intramembranous ossification. Endochondral ossification is the fundamental mechanism for longitudinal bone formation whereby cartilage is replaced by bone. It requires the sequential formation and degradation of cartilaginous structures in the growth plates that serve as templates for the developing bones. During intramembranous ossification, bone is formed directly in the connective tissues. Both processes require the infiltration of osteoblasts and subsequent matrix deposition.

The signaling pathway triggered by activation of FGFRs has been shown to be involved in several stages of limb and bone development. Other major regulators of bone growth include natriuretic peptides (NP), bone morphogenetic proteins (BMP), growth hormone (GH), insulin-like growth factors (IGF), glucocorticoids (GC), thyroid hormone (TH), parathyroid hormone (PTH), PTH related peptide (PTHrP) and Vitamin D.

FGFRs and Disease

A number of birth defects affecting the skeleton are associated with mutations in the genes encoding FGF receptors, specifically Crouzon, Pfeiffer, Jackson-Weiss, Apert and Beare-Stevenson syndromes (Kan, et al., Am J Hum Genet 70, 472, 2002). Mutations in FGFR3 are responsible for achondroplasia, the most common form of human genetic dwarfism (reviewed in Vajo et al., Endocr. Rev. 21, 23, 2000). Specifically, the outcome of the achondroplasia mutation is a stabilized, constitutively activated FGFR3 leading to restricted chondrocyte maturation in the growth plate of long bones and abnormally shortened bones.

The FGFRs have been implicated in certain malignancies and proliferative diseases. FGFR3 is the most frequently mutated oncogene in transitional cell carcinoma (TCC) of the bladder where it is mutated in more than 30% of the cases (Cappellen et al., Nature Genet. 23, 18, 1999). Dvorakova et al. (Br. J. Haematol. 113, 832, 2001) have shown that the FGFR3IIIc isoform is over expressed in the white blood cells of chronic myeloid leukemia (CML) patients. Yee et al. (J. Natl. Cancer 92, 1848, 2000) identified a mutation in FGFR3 linked to cervical carcinoma. Recently, FGFR4 was shown to be associated with pituitary tumors (Ezzat, et al, J. Clin. Invest. 109, 69, 2002) and breast cancer progression (Bange, et al., Cancer Res. 62, 840, 2002).

In contrast, FGFs and their analogs have been shown to be useful for treating indications including wounds (U.S. Pat. Nos. 4,950,483, 5,859,208 and 6,294,359), myocardial infarction (U.S. Pat. Nos. 4,296,100 and 4,378,347), skeletal disorders (U.S. Pat. Nos. 5,614,496 and 5,656,598) and for remodeling cardiac tissue (U.S. Pat. No. 6,352,971).

Receptor Specificity

In light of the large number of FGFs and FGF receptor variants, a major question regarding FGF function is their receptor specificity. All FGFRs tested so far bind FGF-1 (acidic FGF, aFGF) with moderate to high affinity, demonstrating an apparent redundancy in the FGF system. In contrast to FGFR1 and FGFR2, the third receptor subtype, FGFR3 was found to bind to FGF-8, FGF-17 and FGF-18 with high affinity and to FGF-9 with improved selectivity. Specificity may also be achieved by specific proteoglycans expressed in different tissues (Ornitz, Bioessays, 22, 108, 2000). Site-directed mutagenesis and X-ray crystallography were used to study the basis of specificity of FGFs to their receptors (Plotnikov et al., Cell 98, 641, 1999; Plotnikov et al., Cell 101, 413, 2000; Stauber et al., PNAS 97, 49, 2000; Pellegrini et al., Nature, 407, 1029, 2000; Schlessinger et al., Mol Cell, 6, 43, 2000).

FGF Variants

All members of the FGF family share a homology core domain of about 120 amino acids, 28 aa residues are highly conserved and six are identical. Structural studies on several FGFs identified 12 antiparallel β strands each one adjacent to β-loops comprising the core region, conserved throughout the family. The core domain comprises the primary FGFR and heparin binding sites. Receptor binding regions are distinct from heparin binding regions (reviewed in Ornitz and Itoh, Gen. Biol. 2, 3005.1, 2001).

Attempts have been made to achieve altered FGF receptor specificity by deletions or truncations of its ligands, by means of mutations introduced at certain locations within the gene encoding for the proteins. Copending PCT application WO 02/36732 discloses FGF variants having at least one mutation in the β8-β9 loop, having increased receptor specificity to one receptor subtype compared to the corresponding wild type FGF.

Several investigators have demonstrated FGF mutants and variants affecting receptor and heparin binding. Kuroda et al., (Bone, 25, 431, 1999) demonstrated that a full-length FGF-4 polypeptide and a shortened version containing 134 amino acid residues exhibit comparable cellular proliferation and effect on increase of bone density. The shortest form of FGF-4 tested, containing only 111 amino acid residues, exhibited limited growth stimulatory activity.

U.S. Pat. No. 5,998,170 discloses a biologically active FGF-16 molecule having from one to thirty-four amino acids deleted from the N-terminus or from one to eighteen amino acids deleted from the C-terminus.

U.S. Pat. No. 5,512,460 discloses an FGF-9 (glia activating factor, GAF) molecule comprising N-terminus and C-terminus truncations of 53 aa and 13 aa, respectively. U.S. Pat. No. 5,571,895 discloses a 54 aa deletion from the N-terminus of the protein yielding a 154 aa protein retaining its biological activity.

Basic FGF, also known as FGF-2, bFGF, prostatin and heparin binding growth factor 2, is highly conserved among species and has been shown to stimulate the proliferation of a wide variety of cell types. The sequence of FGF-2 has been disclosed U.S. Pat. Nos. 4,994,559; 5,155,214; 5,439,818 and 5,604,293. Human FGF-2 is expressed in several forms, a 210 aa precursor, a 155 aa form, a 146 aa N-terminal truncated form and several others (reviewed in Okada-Ban et al., Int J Biochem Cell Biol, 32, 263, 2000).

FGF-2 has been modified to alter biological properties and binding specificity. U.S. Pat. No. 5,491,220 discloses structural analogues comprising substitution of the β9-β10 loop having altered biological properties and binding specificity. Seno et al. (Eur. J. Biochem. 188, 239, 1990) demonstrated that removal of the C-terminus, not the N-terminus, affects FGF-2 affinity to heparin.

Bailly et al. (FASEB J, 14, 333, 2000) show that FGF-2 mitogenic and differentiation activities may be dissociated by a point mutation in Ser117 (S117A).

Human FGF-2 superagonists have been designed with substitutions at either one or more of the following amino acids: glutamate 89, aspartate 101 and/or leucine 137 (U.S. Pat. No. 6,274,712; note that the aa numbering is according to the 146 aa form of FGF-2 disclosed in Zhang et al, PNAS 88: 3446, 1991). U.S. Pat. No. 6,294,359 discloses agonist and antagonist analogs of FGF-2 that comprise amino acid substitutions at certain heparin and receptor binding domains but does not teach receptor specificity changes.

U.S. Pat. Nos. 5,302,702 and 5,310,883 disclose a recombinant FGF-2 variant, having the alanine of position 3 and the serine of position 5 replaced with glutamic acid, exhibiting increased yields.

The use of FGFs and FGF fragments for targeting cytotoxic agents has been disclosed in WO 01/39788 and U.S. Pat. Nos. 5,191,067; 5,576,288; 5,679,637. A mitogenically active FGF molecule provides a route for introducing the selected agents into the cell.

The extensive efforts made to produce truncation, deletion and point mutation variants in FGF have resulted in changes in affinity to the receptors but not in significant alterations in receptor specificity. Thus, there is an unmet need for highly active and selective ligands for the various types of FGF receptors, useful in selective stimulation or inhibition of these receptors, thereby addressing the clinical manifestations associated with the above-mentioned mutations, and modulating various biological functions.

It is to be explicitly understood that known variants of FGFs are excluded from the present invention.

SUMMARY OF THE INVENTION

It is an object of the present invention to provide variants of members of the FGF family of growth factors with improved receptor specificity and/or affinity and biological activity having a mutation in a major variable protein domain.

It is another object of the present invention to provide FGF variants having improved selectivity for receptor activation.

It is a still another object of the present invention to provide variants of members of the FGF family wherein certain specific truncations of the carboxy and/or amino termini renders them advantageous in that they are more stable, with improved receptor specificity, and/or better targeting agents.

It is a further object of the present invention to provide a pharmaceutical composition comprising variants useful in effecting bone and cartilage formation and regeneration, wound healing, neovascularization and treating FGFR related skeletal and proliferative disorders.

It is yet another object to provide methods for the use of FGF variants to prepare medicaments useful in bone and cartilage formation and regeneration, wound healing, neovascularization and treating FGFR related skeletal and proliferative disorders.

It is yet a further object of the invention to provide methods for the use of FGF variants to prepare medicaments useful for targeting to a particular tissue.

The novel FGF variants provided by this invention fulfill these and other objects.

The present invention is based on the discovery that certain modifications to members of the FGF family of polypeptides render them advantageous in that they have enhanced receptor specificity and/or affinity and altered biological activity.

Unexpectedly, certain FGF variants of the present invention were found to exhibit enhanced biological activity in addition to receptor selectivity. FGF ligands having enhanced biological activity and increased receptor selectivity are desired for treatment of various pathological conditions. Generation of highly active, receptor-specific ligands would be useful for the purpose of developing medicaments for use in tissue repair and regeneration, wound and ulcer healing, bone fracture healing, osteoporosis and other skeletal disorders. In addition, the highly active receptor specific ligands are useful for the growth, selection, proliferation and differentiation of certain cell types including chondrocytes, osteoblasts, progenitor cells and stem cells, in vitro and in vivo.

As disclosed in copending international patent application WO 02/36732 certain modifications to the polypeptide sequence provide FGF variants with enhanced receptor specificity which retain biological activity. Specifically, FGF-9 variants comprising mutations in the loop between the β8 and β9 strands of the polypeptide, previously identified as a conserved receptor binding site, and analogous loops in the other members of the FGF family, unexpectedly provide enhanced receptor subtype specificity.

The present invention is related to a variant of FGF having at least one amino acid substitution in the beta 8-beta 9 loop, said FGF variant characterized in at least one of the following attributes compared to the corresponding wild type FGF: enhanced specificity for one receptor subtype; increased biological activity mediated by at least one receptor subtype with equivalent or reduced activity mediated through another receptor subtype; enhanced affinity to at least one receptor subtype; increased cell proliferation mediated through one receptor subtype.

The present invention is directed to novel variants of FGF, and in particular to variants of FGF-2, FGF-4 and FGF-9. It is now unexpectedly disclosed that FGF-2 variants comprising at least one mutation in the loop between the β8 and β9 strands, herein defined as the β8-β9 loop, provide superagonist properties in addition to enhanced receptor subtype specificity. The variants exhibit enhanced receptor subtype specificity for one receptor subtype compared to the corresponding wild type FGF, by increasing the biological activity mediated by at least one receptor subtype while retaining or reducing the activity mediated through another receptor subtype. According to one currently preferred embodiment of the present invention the FGF-2 variant comprises an amino acid (aa) substitution wherein asparagine 111 (Asn111, N111) is replaced with another amino acid residue thereby providing receptor specificity. These variants are herein denoted FGF2-N111X, having SEQ ID NO:1, wherein X is an amino acid other than asparagine. According to one currently preferred embodiment X is arginine (Arg, R) or Glycine (Gly, G).

The abbreviations used herein correspond to the one letter amino acid code followed by the number designating the amino acid position in the 155 aa form of FGF-2 and the one letter amino acid code for the substituted amino acid.

A currently preferred embodiment of the present invention provides a variant of FGF-2, denoted herein FGF2-N111R, having SEQ ID NO:2, wherein substitution of the asparagine 111 with Arginine (Arg, R) shows essentially unchanged activity towards FGFR3 and FGFR2 while increasing activity for FGFR1.

A currently more preferred embodiment of the present invention provides a variant of FGF-2, denoted herein FGF2-N111G, having SEQ ID NO:3, wherein substitution of the asparagine 111 with Glycine (Gly, G) shows essentially unchanged activity towards FGFR3 while increasing activity for FGFR1, and to a lesser extent towards FGFR2.

Another currently more preferred embodiment of the present invention provides a variant of FGF-2, denoted herein FGF2(3,5Q)-N111X, having SEQ ID NO:4, wherein alanine 3 and serine 5 are replaced by glutamine, and asparagine 111 is other asparagine. According to one currently preferred embodiment X is arginine (Arg, R) or Glycine (Gly, G). A currently most preferred embodiment of the present invention provides a variant of FGF-2, FGF2(3,5Q)-N111G, having SEQ ID NO:5, wherein alanine 3 and serine 5 are replaced by glutamine, and asparagine 111 is substituted with Glycine (Gly, G) showing essentially unchanged activity towards FGFR3IIIb and FGFR2 while increasing activity for FGFR1 and FGFR3IIIc.

The FGF-2 variants are shown to stimulate proliferation of chondrocytes and induce differentiation of neuronal cells and may be used to specifically induce proliferation or differentiation of progenitor cells and embryonic or adult stem cells.

A comparable amino acid substitution is disclosed for FGF-4. FGF-4, also known as HST and K-FGF, is expressed as a 206 aa precursor protein having a 27 aa signal sequence. An FGF-4 molecule, having 179 aa, comprising at least one mutation in the β8-β9 loop provides a variant with improved biological activities. According to one currently preferred embodiment of the present invention the FGF-4 variant comprises an amino acid substitution wherein asparagine 165 (Asn165, N165) is replaced with another amino acid residue thereby providing enhanced biological activity. These variants are herein denoted FGF4-N165X, having SEQ ID NO:6, wherein X is an amino acid other than N (asparagine), preferably R (arginine). A currently more preferred embodiment of the present invention provides a 152 aa form of the protein comprising a 54 amino acid N-terminus truncation in addition to the N165X substitution. These variants are denoted herein L55M-FGF4-N165X, having SEQ ID NO:7. Amino acid numbering of the FGF-4 variants is according to the 206 aa form.

The L55M-FGF4-N165X variant shows a substantial increase in activity toward FGFR3 with unchanged activity towards the FGFR1 and a slight reduction in activity towards the FGFR2.

Preferably the variants have at least 2-fold the activity of the native FGF-2 in terms of proliferation of FGFR bearing cells induced by the variant.

The therapeutic utility of these novel FGF-2 and FGF-4 variants is disclosed for both normal and abnormal FGF receptors, including but not limited to bone regeneration and bone fracture healing, articular chondrocyte repair, osteoporosis, wound healing, ischemic tissue repair, neural tissue survival and repair and neovascularization.

According to the principles of the present invention it is now disclosed that through introduction of a single amino acid substitution within the β8-β9 loop, an FGF polypeptide may undergo interconversion from a mitogen to a differentiation factor, or from a differentiation factor to a mitogen. This unexpected property of the novel variants warrants their advantageous use in selectively inducing proliferation and differentiation of various cell types. The variants of the present invention may be used in vitro or in vivo, alone or in combination to achieve a desired effect of proliferation and/or differentiation. Furthermore, the introduction of an amino acid substitution into the β8-β9 loop of the other members of the FGF family of polypeptides can similarly be used to achieve interconversion of a proliferation factor into a differentiation factor, and a differentiation factor into a proliferation factor.

By way of non-limiting examples, the FGF2-N111X variants, including FGF2(3,5Q)-N111X, are more potent mitogens than the native FGF2. Alternatively, certain FGF9 variants that were disclosed in PCT application WO 02/36732 have now unexpectedly been shown to induce differentiation of articular chondrocytes whereas the wild type protein FGF-9 is both a weak mitogen and a weak differentiation factor. These variants are denoted herein FGF9-W144G, having SEQ ID NO:8 and L37-FGF9-W144X having SEQ ID NO:9. In neuronal cells, the FGF-2 variant of the present invention, FGF2-N111R, is shown to be a more potent differentiation factor than FGF-2, as determined by neurite outgrowth.

Currently preferred embodiments in accordance to the invention comprising variant forms of FGF-2 and FGF-4 are denoted herein as follows:

1) FGF2-N111X (SEQ ID NO: 1) having 155 aa wherein Asn (N) at position III is replaced by X, wherein X is an amino acid other than Asn. The currently preferred amino acid substitution is selected from X=Gly (G) or Arg (R).
2) FGF2-N111G (SEQ ID NO:2) having 155 aa wherein Asn (N) at position 111 is replaced by Gly (G) or Arg (R).

3) FGF2-N111R (SEQ ID NO:3) having 155 aa wherein Asn (N) at position 111 is replaced by Arg (R).
4) FGF2(3,5Q)-N111X (SEQ ID NO:4) having 155 aa wherein Ala3 and Ser5 are replaced with Glu (Q) and Asn (N) at position 111 is replaced by X, wherein X is an amino acid other than Asn. The currently preferred amino acid substitution is selected from X=Gly (G) or Arg (R).
5) FGF2(3,5Q)-N111G (SEQ ID NO:5) having 155 aa wherein Ala3 and Ser5 are replaced with Glu (Q) and Asn (N) at position 111 is replaced by Gly (G).
6) FGF4-N111X (SEQ ID NO:11) having 179 aa and the Asn (N) at position 165 is replaced by X. The currently preferred amino acid substitution is X=Gly (G).
7) L55M-FGF4-N111X (SEQ ID NO: 12) having 152 aa wherein 54 amino acids are truncated from the N-terminus, the Leu (L) at position 55 is replaced by a Met (M) and Asn (N) at position 165 is replaced by X. The currently preferred amino acid substitution is X=Gly (G).

Additionally, certain variants disclosed in PCT application WO 02/36732 are now shown to be effective in selectively inducing proliferation and differentiation of cells.

The amino acid sequences of the variants are denoted herein as follows:
8) W144X-FGF9 (SEQ ID NO:8)
9) L37M-W144X-FGF9 (SEQ ID NO:9)

The focus of the FGF receptors as receptors involved in certain cancers has raised the unmet need for ligands specific for these receptors; preferably a ligand which binds to one FGFR with high specificity and does not substantially bind to the other FGFRs. The high-specificity ligand is able to target a receptor on the surface of a specific tissue or organ. The targeting polypeptides are fusion proteins, chimeras, hybrid proteins or conjugates.

Unexpectedly, certain FGF variants of the present invention were found to retain binding affinity to specific FGF receptors while exhibiting reduced receptor-mediated biological activity, providing variants useful for targeting bioactive agents including polypeptides, peptides and analogs and drugs to specific tissue. Effectively, the variant polypeptides are useful as carriers which can be used for site-specific delivery and concentration of bioactive agent to cells, tissues, or organs in which a therapeutic effect is desired to be effected.

Certain modifications to the FGFs generate polypeptides with improved properties including high binding affinity, modified biological activity such as reduced stimulation of proliferation and enhanced receptor specificity.

According to the principles of the present invention it is now disclosed that mutations in the loop between the β8 and β9 strands of FGFs, herein defined as β8-β9, previously determined to comprise a major conserved binding site demonstrated to interact with FGF receptors, and analogous loops in the other members of the FGF family, provide enhanced receptor subtype specificity and or affinity. According to the principles of the present invention it is now disclosed that truncated FGF variants exhibit reduced activity in promoting growth of receptor bearing cells than their corresponding full-length wild type parent growth factor and are particularly useful for targeting bioactive agents to cells, tissues and organs. Truncated variants of the invention that are most preferred may further comprise at least one mutation in at least one binding site to the receptor and are more receptor-selective than the corresponding full length wild type growth factor. In certain indications, including some skeletal and proliferative diseases, it is advantageous to use inactive ligands for targeting in order to avoid activation of receptors where activation of said receptors may advance the diseased state. According to one aspect of the present invention said FGF variants wherein the N- and/or C-termini are truncated such that the truncation extends near to or within the core domain provide molecules with reduced biological activity useful as an antagonist of FGFR or for targeting bioactive agents to specific cells or tissues or organs. An FGF-9 variant having a 63 amino acid N-terminus truncation, is denoted herein R64M-FGF9, having SEQ ID NO:10. The R64M-FGF9 variant was disclosed in copending PCT patent application WO 02/36732 as the shortest variant of FGF-9 having biological activity and improved binding specificity toward FGFR3. The present invention relates to additional beneficial properties of the R64M-FGF9 variant, specifically for use as a targeting molecule specific for FGFR3.

A currently more preferred variant of the present invention, having a 63 amino acid truncation and an 18 amino acid C-terminus truncation is denoted herein FGF9-2, having SEQ ID NO: 11. The FGF9-2 variant was disclosed in copending PCT patent application WO 02/36732 as a variant of FGF-9 having reduced biological activity. The present invention discloses unexpected additional beneficial properties of the FGF9-2 variant, specifically for use as a targeting molecule specific for FGFR3.

According to yet another currently preferred embodiment of the invention there is provided an FGF comprising a substitution of at least one residue in a major binding site of the molecule to the receptor in conjunction with a truncation of the N- and/or C-termini. An amino acid substitution according to the invention affects binding of the variant to one receptor but not to another thereby providing a basis for receptor specific mutants of FGFs.

The preferred FGF variant has enhanced specificity for one receptor subtype compared to the corresponding wild type parent FGF, by decreasing the biological activity mediated by at least one receptor subtype while retaining the activity mediated through another receptor subtype. The truncated molecule exhibits reduced biological activity while maintaining high receptor affinity.

In a non-limiting example it is possible to diminish the biological activity resulting from FGF-9 binding to FGFR1 while retaining binding to FGFR3. Preferably the binding to FGFR3 is a high affinity binding with reduced biological activity. More preferably the binding to FGFR3 is a high affinity binding with no biological activity.

Preferably the mutation results in a substitution of tryptophan 144 (W144) of the β8-β9 loop as numbered according to wild type parent FGF-9, or an amino acid in the corresponding position of the β8-β9 loop of an FGF. More preferably the mutation is in the β8-β9 loop of FGF-2, FGF-4 or FGF-9. Here we disclose increased receptor specificity by a point mutation in FGF-9 resulting in an amino acid substitution in the loop between the β8 and β9 strands. The variants are furthermore truncated at the N- or C-terminus or both termini wherein the biological activity is reduced but the affinity to the receptor is substantially unaffected.

According to one currently most preferred embodiment of the present invention FGF-9 comprises an amino acid substitution wherein Trp144 (W144) is replaced with other amino acid residues providing receptor specificity and N-terminal and/or C-terminal truncation(s) that reduce the biological activity and retain receptor affinity. Introduction of glycine at position 144 of FGF-9 abolishes its binding to FGFR1, while retaining significant affinity towards FGFR3 and to a lesser extent, FGFR2. According to an additional currently preferred embodiment the R64M-FGF9 variant further comprises a W144 substitution. This variant is denoted herein R64M-FGF9-W144X, having SEQ ID NO:10, wherein Trp144 is substituted with amino acid residues including, but not limited to glycine (G), arginine (R), valine (V) or glutamate (E) that abolish the binding to FGFR1 while retaining high affinity binding to FGFR3 and a lesser affinity to FGFR2. These variants, having reduced biological activity and high receptor affinity are denoted herein R64M-FGF9-W144G, R64M-FGF9-W144R, R64M-FGF9-W144V and R64M-FGF9-W144E.

According to an additional currently more preferred embodiment of the present invention the FGF9-2 variant further comprises a W144 substitution. This variant is denoted herein FGF9-2-W144X, having SEQ ID NO: 12. The FGF9-2 variant further comprises an amino acid substitution wherein Trp144, or the equivalent position in other FGFs, is substituted with amino acid residues including, but not limited to glycine (G), arginine (R), valine (V) or glutamate (E) that abolish the binding to FGFR1 while retaining high affinity binding to FGFR3 and a lesser affinity to FGFR2. These variants, having reduced biological activity and high receptor affinity are denoted herein FGF9-2-W144G, FGF9-2-W144R, FGF9-2-W144V and FGF9-2-W144E.

Another aspect of the invention provides a substitution of another residue in the "8-"9 loop, namely the amino acid adjacent to Trp144, asparagine 143 (Asn143 or N143) of FGF-9, or the equivalent position in other FGFs, with another amino acid residue including, but not limited to serine, to diminish binding to FGFR1 while retaining high affinity binding to FGFR3 and a lesser affinity to FGFR2. Furthermore, truncations reduce biological activity and retain binding capacity of the FGF. These variants are denoted herein R64M-FGF9-N143X, and F9-2-N143X, having SEQ ID NOS:14 and 15, respectively, wherein X is other than asparagine (N) and more preferably serine (S).

Further preferred variants comprise analogous polypeptides of FGF-2, in particular variants comprising the 120 aa core domain and truncations at both the N- and C-termini.

A currently preferred embodiment of the present invention provides a composition useful to target bioactive agents to particular cells, tissues and organs. A currently more preferred embodiment comprises a covalent conjugate or chimeric recombinant (fusion protein) comprising an FGF variant linked to a bioactive agent. This link may be via a direct bond, including a peptide bond, and the bioactive agent may be a detectable label, cytotoxic drug, a pharmaceutically active compound or diagnostic compound. These include, but are not limited to, peptides and peptide analogs, peptidomimetics, oligopeptides, proteins, apoproteins, glycoproteins, antigens and antibodies or antibody fragments, receptors and other membrane proteins, aptamers, enzymes, coenzymes, enzyme inhibitors including tyrosine kinase inhibitors, amino acids and their derivatives, hormones, lipids, phospholipids, toxins and anti-cancer drugs.

In a currently most preferred embodiment the composition comprises chimera or conjugate of R64M-FGF9-W144G or FGF9-2-W144G linked to a peptide or peptide analog.

A currently preferred embodiment of the present invention is a composition useful to increase the size of a bone growth plate in abnormal bone. A currently more preferred embodiment of the present invention is a pharmaceutical composition comprising as an active ingredient a covalent conjugate or chimeric recombinant comprising an FGF variant linked to a bioactive agent. This link may be via a direct bond, including a peptide bond, and the bioactive agent may be a detectable label, cytotoxic drug, a pharmaceutically active compound or diagnostic compound. These include, but are not limited to those bioactive agents previously listed. In one currently most preferred embodiment the abnormal bone is a dysplasic bone, the FGF variant is selected from R64M-FGF9 or FGF9-2, and the bioactive agent is a natriuretic peptide. In another currently most preferred embodiment the FGF variant is selected from R64M-FGF9-W144G or FGF9-2-W144G and the bioactive agent is selected from C-type natriuretic peptide (CNP) or an analog thereof.

The present invention further provides variants useful for regulating activity of a mutated FGF Receptor. A currently preferred embodiment of the present invention is the use of a variant of the invention that acts as an antagonist to reduce the activity of a mutated receptor in diseases and disorders related to FGFR. A currently more preferred embodiment of the present invention is the use of a variant of the invention that acts as an antagonist to reduce the activity of a mutated FGFR3 in diseases and disorders related to FGFR3, including achondroplasia, thanatophoric dysplasia and proliferative diseases including transitional cell carcinoma (TCC) of the bladder, breast cancer and multiple myeloma.

Currently most preferred embodiments in accordance to the invention comprising variant forms of FGF are denoted herein as follows:

10) R64M-FGF9 (SEQ ID NO: 10). The sequence of this variant has been disclosed in PCT application WO 02/36732.

11) R64M-FGF9-W144X (SEQ ID NO:11) having 145aa with a truncation of 63 amino acids from the N-terminus, the Arg (R) at position 64 of the wild type parent FGF-9 replaced by Met (M) and wherein X at position 144 of the wild type parent FGF-9 is other than Trp (W) and more preferably selected from Glycine (G), Arg (R), Val (V) or Glu (E).

12) FGF9-2 (SEQ ID NO: 12). The sequence of this variant has been disclosed in copending PCT application WO 02/36732.

13) FGF9-2-W144X (SEQ ID NO: 13) having 127aa with a truncation of 63 amino acids from the N-terminus, the Arg (R) at position 64 of the wild type parent FGF-9 replaced by Met (M) and a truncation of 18 amino acids from the C-terminus, the Pro (P) at position 191 of the wild type parent FGF-9 replaced with a termination signal and wherein X at position 144 of FGF-9 is other than Trp (W), wherein the currently preferred amino acid substitution is selected from Gly (G), Arg (R), Val (V) or Glu (E).

14) R64M-FGF9-N143X (SEQ ID NO:14) having 145aa with a truncation of 63 amino acids from the N-terminus, the Arg (R) at position 64 of the wild type parent FGF-9 replaced by Met (M) and wherein X at position 143 of the wild type parent FGF-9 is other than Asn (N) and more preferably Ser (S).

15) FGF9-2-N143X (SEQ ID NO:15) having 127aa with a truncation of 63 amino acids from the N-terminus, the Arg (R) at position 64 of the wild type parent FGF-9 replaced by Met (M), a truncation of 18 amino acids from the C-terminus, the Pro (P) at position 191 of the wild type parent FGF-9 replaced with a termination signal and wherein X at position 143 of FGF-9 is other than Asn (N), and more preferably Ser (S).

A currently preferred embodiment of the present invention is a method to target bioactive agents to particular cells, tissues and organs. In a currently more preferred embodiment a composition comprising an FGF complex molecule comprising a covalent conjugate or chimeric recombinant comprising an FGF variant linked to a bioactive agent is administered to a patient in need thereof. In a currently most preferred embodiment the composition comprises an R64M-FGF9-W144G or FGF9-2-W144G and peptide or peptide analog chimera or conjugate.

A currently preferred embodiment of the present invention is a method to increase the size of a bone growth plate in abnormal bone by treating the bone with a pharmaceutical composition comprising a covalent conjugate or chimeric recombinant FGF complex molecule comprising an FGF variant linked to a bioactive agent, further comprising a pharmaceutically acceptable diluent, carrier and/or stabilizer. In a currently more preferred embodiment the abnormal bone is a dysplasic bone, the FGF variant is R64M-FGF9-W144G or FGF9-2-W144G and the bioactive agent is C-type natriuretic peptide (CNP) or an analog thereof. According to one aspect of the invention, the FGF variant is 5' to the CNP, in another aspect the FGF variant is 3' to the CNP. It is to be understood that the CNP analogs include the CNP(1-22) 22 aa peptide, an active CNP(5-22) 17 aa peptide or an active variant thereof.

The amino acid sequences of currently preferred FGF complex molecules, followed by the polynucleotide sequences, are presented herein as follows:

16) FGF9-2-W144X-CNP (1-22) (SEQ ID NO:16) having 152 aa comprising SEQ ID NO:16, linked to a 22 aa CNP molecule or a stable derivative thereof via a polypeptide linker.

17) CNP (1-22)-FGF9-2-W144X (SEQ ID NO:17) having at least 157 aa comprising a CNP (1-22) molecule or a stable derivative thereof, linked to SEQ ID NO:16 via a polypeptide linker.

It is to be understood that a complex molecule comprises an FGF variant having SEQ ID NOS:12-15 linked to a bioactive agent as either the N-terminal component or the C-terminal component of the covalent conjugate or chimeric recombinant. It is further understood that a linker may be a polypeptide linker such as those known in the art. A currently preferred embodiment comprises an FGF variant having SEQ ID NOS:12-15 linked to a bioactive agent as either the N-terminal component or the C-terminal component via a polyglycine linker of 2-20 amino acids.

The polynucleotide sequences corresponding to the novel variants is disclosed herein as follows:

18) FGF2-N111X DNA (SEQ ID NO:18)
19) FGF2-N111G DNA (SEQ ID NO:19)
20) FGF2-N111R DNA (SEQ ID NO:20)
21) FGF2 (3,5Q)-N111X DNA (SEQ ID NO:21).
22) FGF2 (3,5Q)-N111G DNA (SEQ ID NO:22).
23) FGF4-N111X DNA (SEQ ID NO:23)
24) L55M-FGF4-N165X DNA (SEQ ID NO:24).
25) R64M-FGF9 DNA (SEQ ID NO:25) disclosed in PCT application WO 02/36732.
26) R64M-FGF9-W144X DNA (SEQ ID NO:26)
27) FGF9-2 DNA (SEQ ID NO:27) disclosed in PCT application WO 02/36732.
28) FGF9-2-W144X DNA (SEQ ID NO:28).
29) R64M-FGF9-N143X DNA (SEQ ID NO:29).
30) FGF9-2-N143X DNA (SEQ ID NO:30).
31) FGF9-2-W144X-CNP (1-22) DNA (SEQ ID NO:31)
32) CNP (1-22)-FGF9-2-W144X DNA (SEQ ID NO:32).

According to one currently preferred embodiment of the present invention a pharmaceutical composition comprising as an active ingredient at least one variant having SEQ ID NOS:1-17 and a pharmaceutically acceptable carrier, diluent or excipient is provided.

In a currently more preferred embodiment of the present invention the variants having SEQ ID NOS:1-7 are formulated to provide pharmaceutical compositions useful for promoting or accelerating repair or regeneration of endochondral bone, intramembranous bone, articular cartilage, spinal defects and other skeletal disorders and for promoting or accelerating neovascularization in indications including burns, cuts, lacerations, bed sores, ulcers such as those seen in diabetic patients, repair and regeneration of tissue, including skeletal, nerve and vascular tissue. According to yet a further aspect of the present invention is a method of promoting or accelerating bone growth or cartilage repair which comprises administering to a patient a therapeutically effective amount of a pharmaceutical composition in combination with a matrix device. The matrix may be synthetic or natural. In a non-limiting example the matrix is a plasma protein matrix or a calcium phosphate matrix. Thus the present method may be used to promote tissue regeneration and repair including cartilage, bone and wound healing.

According to another aspect of the present invention it is disclosed that the pharmaceutical compositions comprising at least one variant FGF of the present invention having SEQ ID NOS:10-17 have improved therapeutic utility in diseases and disorders associated with FGF receptors. The therapeutic utility of these novel variants is disclosed in diseases involving both normal and abnormal FGF receptors, including but not limited to skeletal disorders including but not limited to Achondroplasia, Hypochondroplasia, and osteoporosis and proliferative diseases and disorders.

According to yet another aspect of the present invention it is disclosed the preferred variants having SEQ ID NO:1-9 have improved utility in the selective induction of proliferation and differentiation of cells. The use of these variants is disclosed for in vitro or in vivo treatment of cells.

According to yet a further aspect of the present invention is a method of promoting or accelerating neovasculogenesis which comprises administering to a patient a therapeutically effective amount of a pharmaceutical composition comprising a variant of the present invention and optionally a matrix-free or matrix device. The matrix may be synthetic or natural. In a non-limiting example the matrix is a plasma protein matrix or a calcium phosphate matrix. Thus the present method may be used to promote tissue regeneration and repair including cartilage, bone and wound healing.

BRIEF DESCRIPTION OF THE FIGURES

FIG. 7A shows the signal distribution while FIG. 7B shows the outline of the cells.

FIGS. 9A-9E show the phenotype of human articular chondrocytes grown in the presence of variants of the present invention.

FIGS. 13A-13D show proteoglycan expression in porcine articular chondrocyte pellet culture, as determined by toluidine blue staining.

DETAILED DESCRIPTION OF THE PREFERRED EMBODIMENTS

Figure 6:
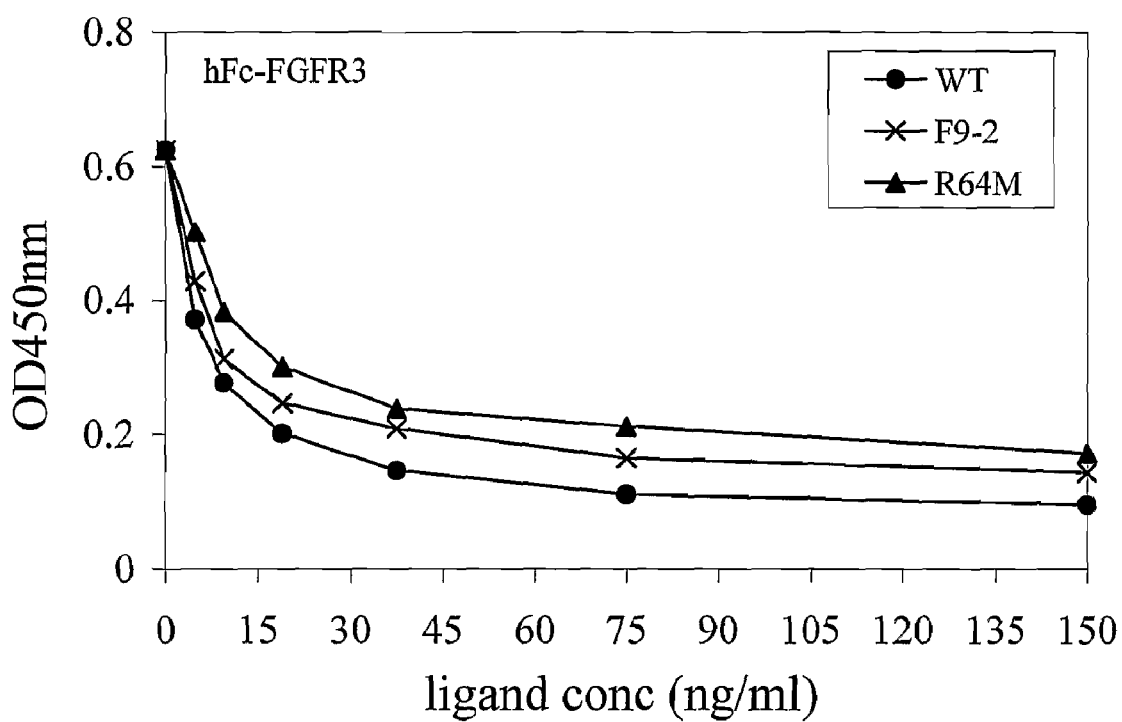
FIG. 6 shows the results of a competition binding assay of FGF-9 variants.

Fibroblast growth factors (FGFs) constitute a large family of structurally related, heparin binding polypeptides, which are expressed in a wide variety of cells and tissues. Overall, the FGFs share between 17-72% amino acid sequence homology and a high level of structural similarity. A homology core of around 120 amino acids is highly conserved and has been identified in all members of the family. The residues of the core domain interact with both the FGFR and heparin. Twelve antiparallel β strands have been identified in the core structure, labeled β through β12, linked one to another by loops of variable lengths, organized into a trefoil internal symmetry. Sequence alignment and location and length of the β strands for FGF-1 through FGF-19 is depicted in FIG. 6 of Plotnikov et al. (Cell 101, 413, 2000).

According to the principles of the present invention it is now disclosed that FGF variants of the present invention comprising amino acid substitutions in the loop between the β8 and β9 strands of the core structure yield variants with improved properties, in addition to altered specificity to FGFRs. In certain embodiments the amino acid substitution yields active variants with superagonist properties. The variants thus obtained will have improved properties in terms of receptor specificity, stability or affinity in addition to enhanced mitogenic activity or differentiation potential. Furthermore, the variants so obtained may further comprise additional modifications within or outside of the β8-β9 loop providing variants with improved stability, solubility or yield.

The FGF ligands with enhanced biological activity and increased receptor selectivity are highly necessary for treatment of various pathological conditions. The variants would be useful for the purpose of research as well as for the purpose of developing possible medicaments for use in tissue repair and regeneration, wound and ulcer healing, bone and cartilage disorders, bone fracture healing, osteoporosis and other skeletal disorders.

Further disclosed are FGF variants which retain binding affinity to specific FGF receptors without stimulating receptor-mediated biological activity, providing FGF variants useful as receptor antagonists or for targeting bioactive agents including polypeptides, peptides and analogs and drugs to specific tissue. The variants with reduced activity are useful as antagonizing a specific receptor in indications related to abnormal FGFR activation. Moreover, the variant polypeptides are useful as carriers which can be used for site-specific delivery and concentration of bioactive agent to cells, tissues, or organs in which a therapeutic effect is desired to be effected. Certain modifications yield polypeptides with improved properties including high binding affinity, reduced biological activity and enhanced receptor specificity, thus providing therapeutically beneficial molecules for treating skeletal disorders, including but not limited to achondroplasia, and proliferative diseases including but not limited to multiple myeloma, transitional cell carcinoma (TCC) of the bladder, breast cancer and cervical carcinoma. The targeting polypeptides are fusion proteins, chimeric recombinants, hybrid proteins or conjugates. For convenience certain terms employed in the specification, examples and claims are described here.

As used herein and in the claims the term "FGFR" denotes a receptor specific for FGF which is necessary for transducing the signal exerted by FGF to the cell interior, typically comprising an extracellular ligand-binding domain, a single transmembrane helix, and a cytoplasmic domain that contains a tyrosine kinase activity. The term "FGFR" includes soluble versions comprising the extracellular domain and lacking the transmembrane and kinase domains, and other variants thereof.

As used herein and in the claims the term "inactive FGF" denotes an FGF molecule or variant which after binding to an FGF receptor elicits stimulation of mitogenesis at most half that of the same cells exposed to the wild type parent FGF molecule, as measured in cell based assays known in the art. More preferably, the variant elicits stimulation of mitogenesis at most one quarter that of the same cells exposed to the wild type parent FGF molecule.

As used herein and in the claims the term "FGF receptor specificity" denotes the fact that a certain FGF molecule binds to a particular FGF receptor and elicits a receptor mediated biological response at a concentration at least twice as high as its activity upon binding to another FGFR. Biological responses are measured by methods known in the art.

The term "affinity" as used herein denotes the ability of a ligand or variant of said ligand to bind to a specific receptor. Modifications to a ligand which stabilize favorable conformation or enhance amino acid side chain interactions will result in increased receptor affinity while those which destabilize favorable conformation or decrease amino acid side chain interactions will result in decreased receptor affinity. A competitive binding assay was established to determine the relative affinity of FGF variants compared to that of wild type parent FGF towards an FGF receptor. Variants having high affinity for an FGF receptor and reduced mitogenic activity are designated potential FGF antagonists As used herein the term "differentiation factor" refers to a substance, in particular a polypeptide, which determines the fate that a cell will acquire upon exposure to that substance, alone or in combination with other substances. In a non-limiting example, differentiation is determined by morphological and phenotypic changes or by biochemical or molecular changes.

As used herein the term "mitogen" or "proliferation factor" refers to a substance that induces an increase in the number of cells.

As used herein and in the claims the term "core", "core domain" or "core structure" denotes a region of homology of around 120 amino acids that is found in all native FGFs. Twenty eight amino acid residues are highly conserved and six are identical. Twelve structurally conserved anti-parallel β strands have been identified in all the FGFs. The core domain comprises the FGFR and heparin binding sites.

As used herein and in the claims the term "beta8-beta9" or "β8-β9" or "β8-β9 loop" refers to the loop of 2 to 5 amino acid residues that lie between the eighth and ninth β-pleated strands of the core structure as disclosed herein.

As used herein and in the claims the terms "amino terminus" and "N-terminus" of a polypeptide may be used interchangeably. Similarly, the terms "carboxy terminus" and "C-terminus" may be used interchangeably.

"Nucleic acid sequence" or "polynucleotide" as used herein refers to an oligonucleotide or nucleotide and fragments or portions thereof, and to DNA or RNA of genomic or synthetic origin which may be single- or double-stranded, and represent the sense or antisense strand. Similarly, "amino acid sequence" as used herein refers to an oligopeptide, peptide, polypeptide, or protein sequence, and fragments or portions thereof, and to naturally occurring, synthetic or recombinant molecules. The terms listed herein are not meant to limit the amino acid sequence to the complete, wild type amino acid sequence associated with the recited protein molecule. The term "variant" as used herein refers to a polypeptide sequence that possesses some modified structural property of the wild type or parent protein. For example, the variant may be truncated at either the amino or carboxy terminus- or both termini or may have amino acids deleted, inserted or substituted. It may be antagonistic or agonistic with respect to normal properties of the native protein. An antagonist is defined as a substance that binds to but does not activate a receptor mediated response. An agonist is defined as a substance induces a receptor-mediated response similar to that induced by the wild type ligand. A superagonist is defined as a substance that induces a cellular or physiological response at a concentration at least half that observed with the wild type protein. More preferably, a cellular or physiological response is elicited at a concentration at least four fold less than that observed with the wild type protein. A biological response may be, for example, the stimulation of cell division, differentiation, angiogenesis or wound repair. A biological response may encompass other functional properties of the wild type parent protein and would be well known to those practicing the art.

It is contemplated in this invention that a variant may have altered binding to a receptor compared to that of the wild type parent protein. This binding may enhance or depress a biological response. Accordingly, the variant may have altered specificity for one or more receptors.

The variant may be generated through recombinant DNA technologies, well known to those skilled in the art. As used herein, the term "polymerase chain reaction" ("PCR") refers to the methods disclosed in U.S. Pat. Nos. 4,683,195; 4,683,202 and 4,965,188 hereby incorporated by reference.

The term "expression vector" and "recombinant expression vector" as used herein refers to a recombinant DNA molecule containing a desired coding sequence and appropriate nucleic acid sequences necessary for the expression of the operably linked coding sequence in a particular host organism. The expression vector may comprise sequences encoding heterologous domains including but not limited to protein detection, purification or cleavage sequences that may be fused at the N- or C-terminus to the desired coding sequence, to yield a fusion protein. It is contemplated that the present invention encompasses expression vectors that are integrated into host cell genomes, as well as vectors that remain unintegrated into the host genome.

As used herein, the "amino acids" used in the invention are those which are available commercially or are available by routine synthetic methods. Certain amino acid residues may require special methods for incorporation into the peptide, and sequential, divergent or convergent synthetic approaches to the peptide sequence are useful in this invention. Natural coded amino acids and their derivatives are represented by either the one-letter code or three-letter codes according to IUPAC conventions. When there is no indication, the L isomer was used. Other pharmaceutically active amino acids, including synthetic amino acids, are known in the art and are intended to be included in the invention.

As used herein and in the claims a "bioactive agent" is any agent which is desired to be delivered to cells, tissues or organs for modulating or modifying cell function, including for therapeutic effects. In accordance with the present invention, bioactive agents include, but are not limited to, pharmaceutically active compounds or diagnostic compounds. These include, but are not limited to, peptides and peptide analogs, peptidomimetics, oligopeptides, proteins, apoproteins, glycoproteins, antigens and antibodies or antibody fragments thereto, receptors and other membrane proteins, aptamers, enzymes, coenzymes, enzyme inhibitors, amino acids and their derivatives, hormones, lipids, phospholipids, liposomes; toxins such as ricin or ricin fragments, aflatoxin, digoxin, xanthotoxin, rubratoxin, ribosome inactivating proteins; tyrosine kinase inhibitors, photoreactive agents, antibiotics such as cephalosporins, penicillin and erythromycin; analgesics and anti-inflammatory substances; antimicrobial agents; antihypertensive agents; antiviral agents; antihistamines; anti-cancer drugs including chemotherapeutic agents, such as chlorambucil, carboplatin, derivatives of busulfan, doxorubicin, etoposide, genestein, topotecan (TPT); tranquilizers; neuroprotective agents; antispasmodics; anti-Parkinson agents; vitamins. Other bioactive agents include nucleotides; oligonucleotides; polynucleotides; and their art-recognized and biologically functional analogs and derivatives; plasmids, cosmids, artificial chromosomes, other nucleic acid vectors; antisense polynucleotides including those substantially complementary to at least one endogenous nucleic acid or those having sequences with a sense opposed to at least portions of selected viral or retroviral genomes; promoters; enhancers; inhibitors; other ligands for regulating gene transcription and translation.

As herein, the terms "bone defect" or "bone disorder" is meant an imbalance in the ratio of bone formation to bone resorption, such that, if unmodified, the subject will exhibit less bone than desirable, or the subject's bones will be less intact than desired. Bone deficit may also result from mutation, fracture, from surgical intervention or from dental or periodontal disease. By "cartilage defect" or "cartilage disorder" is meant damaged cartilage, less cartilage than desired, or cartilage that is less intact and coherent than desired. Contemplated are indications including rheumatoid arthritis, osteoarthritis and knee injuries.

Representative uses of the compounds of the present invention include: repair of bone defects and deficiencies, such as those occurring in closed, open and non-union fractures; prophylactic use in closed and open fracture reduction; promotion of bone healing in plastic surgery; stimulation of bone ingrowth into non-cemented prosthetic joints and dental implants; elevation of peak bone mass in pre-menopausal women; treatment of growth deficiencies; treatment of periodontal disease and defects, and other tooth repair processes; increase in bone formation during distraction osteogenesis; treatment of articular chondrocytes prior to heterologous or autologous transplantation and treatment of other skeletal disorders, such as age-related osteoporosis, post-menopausal osteoporosis, glucocorticoid-induced osteoporosis or disuse osteoporosis and arthritis. The compounds of the present invention are useful in repair of congenital, trauma-induced or surgical resection of bone (for instance, for cancer treatment), and in cosmetic surgery. Further, the compounds of the present invention can be used for limiting or treating cartilage defects or disorders. Treatment includes direct application of the variants to the traumatized area or systemic therapy as well as treatment of cells ex vivo and in vitro for tissue engineering and tissue regeneration.

As used herein, the terms "fusion protein" or "chimera", "chimeric recombinant" or "hybrid" refer to a single polypeptide produced using host cells expressing a single polynucleotide encoding an FGF variant of the invention and a bioactive agent including a polypeptide, peptide or peptide analog contiguous and in open reading frame. Certain peptide linkers may be incorporated to separate the FGF and the bioactive polypeptide, peptide or peptide analog. Using current methods of genetic manipulation, a variety of peptides or peptide hormones, including natriuretic peptides such as CNP or growth hormone, can be translated as fusion proteins with FGF variants which in turn can specifically target cells and facilitate internalization. The present invention provides a highly effective system for delivery of an activity-inducing moiety into a particular type or class of cells. The fusion proteins generated can be screened for the desired specificity and activity utilizing the methods set forth in the examples and by various routine procedures. The FGF variant fusion proteins encoded by the nucleic acids of the present invention must be able to specifically bind the selected target cell and internalize the FGF fusion.

As used herein, the term "conjugate" refers to a bioactive agent covalently bound to a carrier or targeting moiety. Certain variants of the invention provide carriers or targeting agents for bioactive agents.

An FGF "targeting molecule" or "complex molecule" refers to an FGF variant of the invention linked to a bioactive agent as a recombinant chimera or covalent conjugate.

Provided in the present invention are pharmaceutical compositions comprising an FGF variant and a bioactive agent as a fusion protein or alternatively an FGF variant conjugate comprising an FGF variant and a bioactive agent that are covalently bound useful for FGF targeting. The present invention further provides methods for inhibiting proliferation of cells that express FGFRs comprising administering an FGF variant targeting composition to the cells. For example the composition is administered in a therapeutically effective amount to a subject that has a tumor, wherein the tumor cells express specific FGFR.

FGF activity is conveniently determined using biological assays performed in-vitro, ex-vivo and in vivo. The assays are used to demonstrate the activity elicited upon binding of an FGF molecule to its receptors. The biological assays routinely used to test activities of variant FGFs include, but are not limited to, the following:
  i. binding of variant FGFs to cloned FGF receptors expressed on immortalized cell lines, thereby eliciting a biological response including cell proliferation or inhibition of cell proliferation;
  ii. cell culture systems;
  iii. stimulation of bone growth in animal models of bone growth and cell cultures;
  iv. enhancement of cartilage repair in animal models of cartilage disease and trauma.

Design of Variants

One currently preferred embodiment of the invention is an FGF molecule in which an amino acid substitution is incorporated into the β8-β9 loop. Structural data has recently identified that domain as a major binding site demonstrated to interact with the link connecting the Ig-like 2 (D2) and Ig-like 3 (D3) domains of the receptor (Plotnikov et al., Cell 98, 641 1999). Plotnikov et al., (Cell 101, 413, 2000) have shown that certain domains in the FGFR such as βC'-βE (D2-D3 linker) and βF-βG (D3) regulate FGF-2 binding specificity by interacting with the β4-β5 loop and the amino terminus of FGF.

Additionally, FGFR2 makes hydrophobic contacts with Asn102 of FGF-2 (numbering of aa is according to FGF-2 lacking the 9 aa signal peptide; equivalent to N111 as denoted herein) and forms hydrogen bonds with Asn104 (equivalent to N113). An Asn104 (N113) substitution led to a 400-fold reduction in binding affinity of FGF2 for FGFR1.

Surprisingly, the inventors herein disclose an increase in FGFR1 activity for a variant having a neighboring N111 substitution in FGF-2.

Table 1 depicts the amino acid alignment of the residues in the β8-β9 loop of the known FGFs and 1-3 adjacent residues from the β strand on either side. The Asn111 of FGF-2 AND FGF-4 and the Trp 144 of FGF-9 are highlighted in bold and underlined.

TABLE 1

Amino acid sequence alignment of the β8-β9 and adjacent residues

| | | |
|---|---|---|
| FGF-1 | LEENHYNTY | Residues:104-112 (SEQ ID NO:33) |
| FGF-2 | LESN**<u>N</u>**YNTY | Residues:107-115 (SEQ ID NO:34) |
| FGF-3 | IHELGYNTY | Residues:121-129 (SEQ ID NO:35) |
| FGF-4 | LLPN**<u>N</u>**YNAY | Residues:161-169 (SEQ ID NO:36) |
| FGF-5 | FQENSYNTY | Residues:166-174 (SEQ ID NO:37) |
| FGF-6 | LLPNNYNTY | Residues:163-171 (SEQ ID NO:38) |
| FGF-7 | ILENHYNTY | Residues:143-151 (SEQ ID NO:39) |
| FGF-8 | VLENNYTAL | Residues:151-159 (SEQ ID NO:40) |
| FGF-9 | FEEN**<u>W</u>**YNTY | Residues:140-148 (SEQ ID NO:41) |
| FGF-10 | IEENGYNTY | Residues:156-164 (SEQ ID NO:42) |
| FGF-11 | VFENYYVLY | Residues:149-157 (SEQ ID NO:43) |
| FGF-12 | VFENYYVIY | Residues:151-159 (SEQ ID NO:44) |
| FGF-13 | VFENYYVTY | Residues:147-155 (SEQ ID NO:45) |
| FGF-14 | VFENYYVIY | Residues:149-157 (SEQ ID NO:46) |
| FGF-15 | MDCLGYNQY | Residues:133-141 (SEQ ID NO:47) |
| FGF-16 | FEENWYNTY | Residues:139-147 (SEQ ID NO:48) |
| FGF-17 | VLENNYTAF | Residues:133-141 (SEQ ID NO:49) |
| FGF-18 | VLENNYTAL | Residues:133-141 (SEQ ID NO:50) |
| FGF-19 | IRPDGYNVY | Residues:126-134 (SEQ ID NO:51) |
| FGF-20 | FEENWYNTY | Residues:143-151 (SEQ ID NO:52) |
| FGF-21 | LLEDGYNVY | Residues:127-135 (SEQ ID NO:53) |
| FGF-22 | IEENGHNTY | Residues:119-127 (SEQ ID NO:54) |
| FGF-23 | TLENGYDVY | Residues:119-127 (SEQ ID NO:55) |
| FGF-CX | FEENWYNTY | Residues:143-151 (SEQ ID NO:56) |
| Jaffa | LLEDGYNVY | Residues:127-135 (SEQ ID NO:57) |

Note:
The aa numbering of FGF-2 is according to the 155 aa isoform; amino acid 107 would be 98 in the 146 aa isoform. Sequence alignment for FGF-1-FGF-19 is according to Plotnikov et al. (Cell 101, 413, 2000). FGF-20-23 sequences were identified in Kirikoshi et al. (BBRC 274, 337, 2000), Nishimura et al. (BBA 1492, 203, 2000), Nakatake et al. (BBA 1517, 460, 2001) and Yamashita et al.(BBRC 277, 494 2000), respectively. The FGF-CX sequence is disclosed in WO 01/07595. FGF-18 is also known as zFGF-5. The human FGF Jaffa sequence is disclosed in WO 01/38357.

Preferred Embodiments

As disclosed in copending PCT patent application WO 02/36732, certain modifications to the polypeptide sequence provide variants with enhanced receptor specificity which retain biological activity. Specifically, FGF variants comprising mutations in the loop between the β8 and β9 strands, herein defined as β8-β9, previously determined to comprise a major binding site demonstrated to interact with the receptor, and analogous loops in the other members of the FGF family, provide enhanced receptor subtype specificity. Here we disclose increased receptor specificity and/or affinity and enhanced biological activity of FGF ligands by amino acid substitutions in the β8-β9 loop, specifically at position 111 of wild type FGF-2.

Substitution of aligned residues in FGF-2, exemplified by replacing Asn 102 (N111 of the 155 aa isoform) with Ala (N102A) (Zhu et al., Protein Eng, 10, 417, 1997) was reported to exhibit no receptor specificity alterations. Disclosed herein are FGF-2 variants wherein the identical asparagine at position 111 (N111) is substituted with another residue unexpectedly exhibiting both an increase in biological activity and increased receptor specificity.

A currently preferred embodiment of the invention is denoted FGF2-N111X wherein X is other than asparagine and more preferably selected from glycine (Gly, G) or arginine (Arg, R). This sequence of this variant is denoted herein SEQ ID NO:1. A currently preferred embodiment of the present invention provides a variant of FGF-2, denoted herein FGF2-N111R having SEQ ID NO:2, wherein substitution of the asparagine 111 with arginine (Arg, R) shows essentially unchanged activity towards FGFR3 and FGFR2 while increasing activity for FGFR1.

A currently more preferred embodiment of the present invention provides a variant of FGF-2, denoted herein FGF2-N111G having SEQ ID NO:3, wherein substitution of the asparagine 111 with glycine (Gly, G) shows essentially unchanged activity towards FGFR3 while increasing activity for FGFR1, and to a lesser extent towards FGFR2.

The number designations correspond to the three letter or one-letter amino acid codes followed by the amino acid position in the 155 amino acid form of FGF-2.

The variants of the invention that are most preferred may further comprise additional modifications within, or outside of, the β8-β9 loop. Examples of modifications include truncations of the N- or C-terminus or both termini and/or amino acid substitutions, deletions or additions wherein the variants retain superior mitogenic activity mediated via FGFRs with unimpaired or improved affinities compared to the wild type parent FGF-2, from which it was derived. The additional modifications function to improve certain properties of the variants including enhanced stability, increased yield of recombinants, solubility and other properties known in the art. For example, FGF-2 may comprise amino acid substitutions at amino acid positions 3 and 5 wherein alanine (Ala, A) and serine (Ser, S) are replaced with Glutamine (Gln, Q) (A3Q and S5Q) providing variants with improved yields and stability. A currently preferred embodiment of the present invention is denoted herein FGF2(3,5Q)-N111X, SEQ ID NO:4. Table 2 presents a summary of receptor specificity of the FGF2 variants of the present invention.

TABLE 2

Specificity of FGF2(3,5Q)-N111X variants towards FGFR-expressing FDCP cells.

| Mutant | FGFR1 | FGFR2 | FGFR3IIIb | FGFR3IIIc |
|---|---|---|---|---|
| FGF-2 | + | + | − | + |
| FGF2(3,5Q)-N111G | ++ | + | − | +++ |
| FGF2-N111R | +++ | + | − | + |

The corresponding position of N111 in FGF-4 is N165 (numbering according to the 206 aa form). FGF-4 was shown to have high affinity for the HSPGs which enhances FGFR binding and activation. The wild type FGF-4 is shown to induce a high level of proliferation through FGFR1 and a lower level through FGFR2, with negligible activity through FGFR3. Activity through FGFR3, as measured in a proliferation assay, is enhanced by substitution of an amino acid at position N165 and truncation of N-terminal amino acids. A currently preferred embodiment of the present invention is an FGF4 variant denoted herein FGF4-N165X, having SEQ ID NO:6, wherein X is other than asparagine. A currently more preferred embodiment of the present invention is denoted herein L55M-FGF4-N165X, SEQ ID NO:7, wherein X is other than asparagine. This variant induces proliferation through FGFR3 while maintaining the same level of activity through FGFR1 and FGFR2.

The therapeutic utility of these novel FGF-2 and FGF-4 variants is disclosed for both normal and abnormal FGF receptors, including but not limited to cartilage and bone regeneration and bone fracture healing, articular chondrocyte proliferation, osteoporosis, wound healing, ischemic tissue repair, neural tissue survival and repair and neovascularization. Additionally, the high receptor-specificity of these novel variants warrants their use in targeting bioactive agents, in particular cytotoxic material to cells overexpressing FGFR receptors, for the treatment of proliferative diseases.

In a currently preferred embodiment of the present invention the variants having SEQ ID NOS:1-9 are formulated to provide pharmaceutical compositions useful for promoting or accelerating repair or regeneration of endochondral bone, intramembranous bone, cartilage, including articular cartilage, spinal defects and other skeletal disorders and for promoting or accelerating neovascularization in indications including burns, cuts, lacerations, bed sores, ulcers such as those seen in diabetic patients, repair and regeneration of tissue, including skeletal, skin and vascular tissue. The compositions comprise the variant and further comprise an HSPG as carrier or stabilizer and a matrix-free or matrix device.

Unexpectedly, certain FGF variants of the present invention were found to retain binding affinity to specific FGF receptors while exhibiting reduced receptor-mediated biological activity, providing variants useful for targeting bioactive agents including polypeptides, peptides and analogs and drugs to specific tissue. Effectively, the variant polypeptides are useful as carriers which can be used for site-specific delivery and concentration of bioactive agent to cells, tissues, or organs in which a therapeutic effect is desired to be effected.

The equivalent position of N111 in FGF-9 is W144 (tryptophan at position 144 of the wild type protein). We generated substitutions at the W144 site and tested them for receptor specificity. The tryptophan was replaced with either Gly (G), Ala (A), Val (V), Asn (N), Glu (E) or Arg (R). The W144Q W144V, W144E and W144R variants showed diminished specificity towards FGFR1 and retention of specificity towards the FGFR3 receptor. The W144A or W144N variants behaved as native FGF-9. In addition, a substitution of the adjacent Asn (asparagine) at position 143 to a Ser (Serine), N143S, resulted in activation of FGFR3 and not FGFR1.

Table 3 summarizes the specificity of the FGF-9 variants to FDCP cells transfected with the various FGFR as determined in a cell proliferation assay.

TABLE 3

Specificity of FGF9 variants towards FGFR-expressing FDCP cells.

| Mutant | FGFR-1 | FGFR-3 |
|---|---|---|
| WT-FGF-9 | + | + |
| FGF-9 W144G | − | + |
| FGF-9 W144A | + | + |
| FGF-9 W144V | − | + |
| FGF-9 W144N | + | + |
| FGF-9 W144E | − | + |
| FGF-9 W144R | − | + |
| FGF-9 N143S | − | + |

According to additional preferred embodiments, the FGF comprises the substitution of Trp 144 (WI44) of FGF-9 with either Gly (G), Val (V), Glu (E) or Arg (R).

In a preferred embodiment of the present invention, the variant comprises one or more amino acid substitutions in the β8-β9 loop and a truncation at either or both the N or C terminus. These variants would be advantageous in terms of their stability and/or solubility and receptor affinity and specificity, and concomitant reduced biological activity. FIG. 5B shows the reduced level of mitogenic activity of certain preferred FGF-9 variants in a proliferation assay in FGFR1 or FGFR3-transfected FDCP cells. The X axis is concentration of FGF9 variant measured in ng/ml, while the Y axis depicts absorption at 490 nm and reflects mitogenicity. An inactive variant will elicit a mitogenic response through a specific receptor at a level not to be lower than at least half two-fold of that of the corresponding native FGF at a concentration not higher than 50-fold of that of the native FGF, more preferably not higher than 20-fold and most preferably not higher than 10-fold than that of the native FGF receptor ligand.

Upon removal of amino acid residues near and into the core structure, the FGF protein loses receptor affinity. FGF9-2, a 127 aa represented as SEQ ID NO: 12 has reduced mitogenic capacity relative to wild type FGF-9. The R64M-FGF9 variant of 145 aa, represented as SEQ ID NO:10, provides the shortest FGF-9 polypeptide that retains binding specificity toward FGFR3 and has lost the binding capacity toward FGFR1, as determined in a mitogenic assay. FIG. 5B shows that although the mitogenic activity of R64M-FGF9 is reduced in comparison to that of wild type FGF-9 the variant retains high specificity towards FGFR3 yet shows reduced activity and does not elicit a response through FGFR1. A currently more preferred embodiment of the invention is an R64M-FGF9 variant further comprising an amino acid substitution in the β8-β9 loop. These variants are denoted herein R64M-FGF9-W144X and R64M-FGF9-N143X, SEQ ID NO:11 and 14, respectively. Corresponding polynucleotide sequences are represented as SEQ ID NOS:26 and 29, respectively.

Figure 7A:
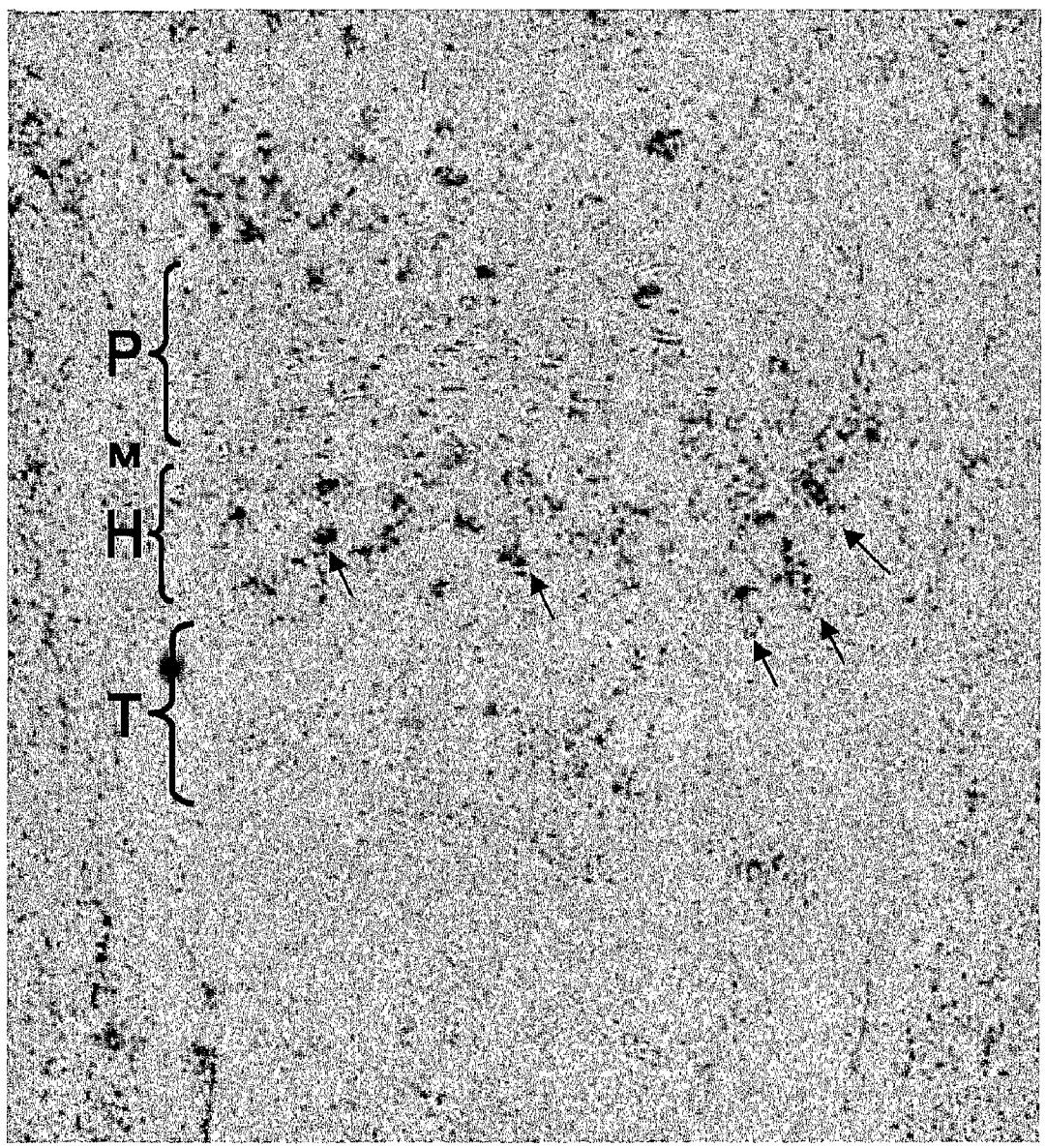
FIGS. 7A and 7B show two exposures of the distribution of $I^{125}$ FGF9-2-W144G variant in the mouse growth plate following IP delivery.
Figure 7B:
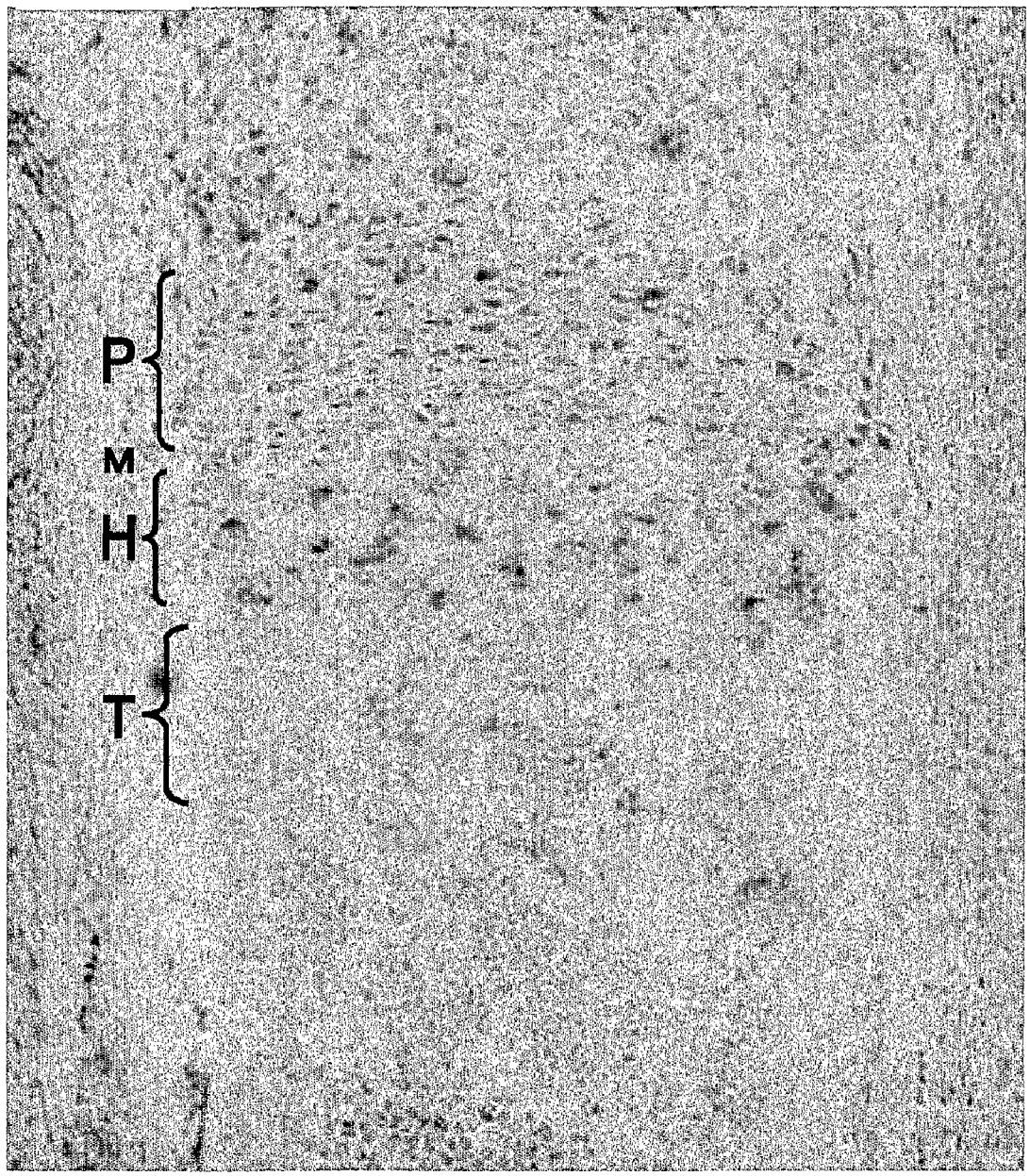

A currently most re preferred embodiment is the inactive variants of FGF-9 denoted herein as FGF9-2-W144X, the amino acid sequence of which is represented as SEQ ID NO:12 wherein X is other than tryptophan and currently most preferred amino acid substitution I selected from Glycine (G), Arg (R), Val (V) or Glu (E). The corresponding polynucleotide sequence is presented as SEQ ID NO:28. The currently more preferred embodiments of the inactive variant of FGF-9 are denoted herein as FGF9-2-W144G, FGF9-2-W144V and FGF9-2-W144E. Introduction of glycine at position 144 of FGF-9 abolished its binding towards FGFR1 while retaining significant affinity towards FGFR3 and to a lesser extent, FGFR2. Furthermore, the FGF9-2-W144G variant specifically targets the growth plate, as shown in FIGS. 7A and 7B.

Methods of Producing and Using Variants

The most preferred method for producing the variants is through recombinant DNA technologies, well known to those skilled in the art. For example, the variants may be prepared by Polymerase Chain Reaction (PCR) using specific primers for each of the truncated forms or the amino acid substitutions as disclosed herein below. The PCR fragments may be purified on an agarose gel and the purified DNA fragment may be cloned into an expression vector and transfected into host cells. The host cells may be cultured and the protein harvested according to methods known in the art. According to another aspect of the present invention it is disclosed that the preferred variant FGFs have improved therapeutic utility in diseases and disorders involving FGF receptors.

The therapeutic utility of these novel variants is disclosed for both normal and abnormal FGF receptors, including but not limited to bone regeneration and bone fracture healing, osteoporosis, wound healing, malignant cells overexpressing FGFR receptors, Achondroplasia and Hypochondroplasia (a condition associated with moderate but variable, disproportionate shortness of limbs). According to currently more preferred embodiments it is possible to target drugs and other bioactive molecules, including but not limited to cytotoxic drugs, peptides and analogs and polypeptides to cells bearing FGFR3 without appreciably affecting cells bearing FGFR1. This is accomplished by conjugating the drug of choice to a variant FGF of the invention. According to even more preferred embodiments of the present invention it is now possible to target drugs and other bioactive molecules, including but not limited to peptides and cytotoxic drugs, to one or more specific subtype of FGFR2 and/or FGFR3. Most preferred embodiments of the invention are particularly useful in conjugates with drugs for inhibiting cell proliferation and facilitating or enhancing the treatment of defects or tumors bearing a specific receptor subtype, without interfering with the growth of normal cells or tissues bearing other receptor subtypes. In a non-limiting example, FGF9-2-W144G targeting compositions can comprise a FGF9-2-W144G component and cytotoxin that are covalently bound to each other. Another example is a conjugate with a tyrosine inhibitor such as, but not limited to, genistein. Alternatively, FGF9-W144G targeting compositions can comprise an FGF9-2-W144G targeting fusion protein. In a currently most preferred embodiment a fusion protein of an inactive variant of the present invention and a peptide or peptide analog is used for targeting of said peptide or analog to a specific cell, tissue or organ.

A "targeting molecule" is defined herein as a molecule which is bound by a receptor and transported to a cell by a receptor-mediated process. Examples of suitable targeting molecules include, but are not limited to, glucose, galactose, mannose, insulin, a peptide growth factor, cobalamin, folic acid or derivatives, biotin or derivatives, albumin, texaphyrin, metallotexaphyrin, porphyrin, any vitamin, any coenzyme, an antibody, an antibody fragment (e.g., Fab) and a single chain antibody variable region (scFv). A skilled artisan will readily recognize other targeting molecules including ligands which bind to cell receptors and which are transported into a cell by a receptor-mediated process. The present invention is intended to include all such targeting molecules.

In another currently preferred embodiment bioactive agents are targeted to a desired tissue, specifically the growth plate of the bones. This may be achieved by methods known to one skilled in the art and include, in a nonlimiting manner, a chimeric protein comprising a FGF variant of the present invention as carrier fused to a bioactive agent including peptides and peptide analogs. According to a currently more preferred embodiment a natriuretic peptide or a functional derivative thereof is fused to an FGF variant of the invention, preferably FGF9-2-W144G, herein denoted FGF9-2-W144G-CNP having SEQ ID NO:16, wherein FGF9-2-W144G is fused to CNP via a Glycine linker. Alternatively, the CNP moiety is linked to an FGF variant, such that the CNP moiety lies 5' to the FGF, herein denoted CNP(1-22)-FGF9-2-W144G, having SEQ ID NO:17.

According to the principles of the present invention it is now disclosed that the through introduction of a single amino acid substitution within the β8-β9 loop, an FGF may undergo interconversion from a mitogen to a differentiation factor, or from a differentiation factor to a mitogen. This property of the novel variants warrants their use in selectively inducing proliferation and differentiation of various cell types. For are more potent inducers of proliferation than the native FGF2. Alternatively, the FGF9 variants, W144G-FGF9 and L37M-W144G-FGF9, having SEQ ID NO:8 and 9 respectively, induce differentiation of articular chondrocytes whereas the wild type protein FGF-9 is both a weak mitogen and a weak differentiation factor. The variants of the present invention may be used in vitro or in vivo, alone or in combination to achieve a desired effect of proliferation and/or differentiation. In one non-limiting example of autologous chondrocyte implantation (ACI) the FGF2-N111X variant is added to a culture of human chondrocytes prepared from a biopsy to induce rapid proliferation of the cells. This is followed by the addition of the FGF9-W144G variant to induce differentiation of the cultured cells. The differentiated cells may then be reintroduced to a subject in need of treatment for the repair of diseased or traumatized cartilage tissue. The variants may be used to culture a variety of cell types including osteoblasts, neurons, hematopoietic cells, progenitor cells and stem cells. Furthermore, the variants may be used for the induction of proliferation and/or differentiation in vivo.

Pharmacology

The present invention also contemplates pharmaceutical formulations, both for veterinary and for human medical use, which comprise as the active agent one or more polypeptide(s) of the invention, as well as the use of a polypeptide of the invention in the manufacture of a medicament for the treatment or prophylaxis of the conditions variously described herein.

In such pharmaceutical and medicament formulations, the active agent preferably is utilized together with one or more pharmaceutically acceptable carrier(s) therefore and optionally any other therapeutic ingredients. The carrier(s) must be pharmaceutically acceptable in the sense of being compatible with the other ingredients of the formulation and not unduly deleterious to the recipient thereof. The active agent is provided in an amount effective to achieve the desired pharmacological effect, as described above, and in a quantity appropriate to achieve the desired daily dose.

Another critically functional component in FGF signaling is proteoglycans such as heparan sulfate. FGFs fail to bind and activate FGF receptors in cells deprived of endogenous heparan sulfate. Proteoglycan refers to heparan sulfate proteoglycans (HSPG) or other types including chondroitin sulfate-, keratin sulfate-, and dermatan sulfate proteoglycans.

The dose of the pharmaceutical composition of the present invention may vary with the kind of disease, the age of patient, body weight, the severity of disease, the route of administration, etc.

Apart from other considerations, the fact that the novel active ingredients of the invention are polypeptides, polypeptide variants or fusion proteins dictates that the formulation be suitable for delivery of these types of compounds. Clearly, peptides are less suitable for oral administration due to susceptibility to digestion by gastric acids or intestinal enzymes. Apart from other considerations, the fact that the novel active ingredients of the invention are polypeptides dictates that the formulation be suitable for delivery of this type of compounds. Clearly, peptides are less suitable for oral administration due to susceptibility to digestion by gastric acids or intestinal enzymes. Specific formulations may be designed to circumvent these problems, including enterocoating, gelatin capsules, emulsions and the like. Nevertheless, bioavailability is impaired by poor gastrointestinal absorption and the routes of administration are preferably parenteral. The preferred routes of administration are intra-articular (IA), intravenous (IV), intramuscular (IM), subcutaneous (SC), intradermal (ID), or intrathecal (IT). A more preferred route is by direct injection at or near the site of disorder or disease.

As used herein a "pharmaceutical composition" refers to a preparation of one or more of the active variant selected from the sequences, SEQ ID NO:1-17 described herein, or physiologically acceptable salts or prodrugs thereof, with other chemical components such as physiologically suitable carriers and excipients. The purpose of a pharmaceutical composition is to facilitate administration of a compound to an organism.

The term "prodrug" refers to an agent, which is converted into an active parent drug in vivo. Prodrugs are often useful because in some instances they may be easier to administer than the parent drug. They may, for instance, be bioavailable by oral administration whereas the parent drug is not. The prodrug may also have improved solubility compared to the parent drug in pharmaceutical compositions.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols. Pharmaceutical compositions may also include one or more additional active ingredients.

Pharmaceutical compositions of the present invention may be manufactured by processes well known in the art, e.g., by means of conventional mixing, dissolving, granulating, grinding, pulverizing, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active compounds into preparations which, can be used pharmaceutically. Proper formulation is dependent upon the route of administration chosen.

For injection, the compounds of the invention may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants for example DMSO, or polyethylene glycol are known in the art.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for the chosen route of administration. For buccal administration, the compositions may take the form of tablets or lozenges formulated in conventional manner. For administration by inhalation, the variants for use according to the present invention are delivered in the form of an aerosol spray presentation from a pressurized pack or a nebulizer with the use of a suitable propellant known in the art. In the case of a pressurized aerosol, the dosage unit may be determined by providing a valve to deliver a metered amount. Capsules and cartridges of, e.g., gelatin for use in an inhaler or insufflator may be formulated containing a powder mix of the peptide and a suitable powder base.

Pharmaceutical compositions for parenteral administration include aqueous solutions of the active ingredients in water-soluble form. Additionally, suspensions of the active compounds may be prepared as appropriate oily injection suspensions. Suitable lipophilic solvents or vehicles include fatty oils such as sesame oil, or synthetic fatty acids esters such as ethyl oleate, triglycerides or liposomes. Aqueous injection suspensions may contain substances which increase the viscosity of the suspension, including but not limited to natural substances and polymers such as collagen, sorbitol, dextran or hyaluronic acid (HA) and derivatives, synthetic polymers, cellulose derivatives including sodium carboxymethyl cellulose (CMC) and derivatives of said substances or any natural or synthetic carrier known in the art (Pillai and Panchagnula, Curr. Opin. Chem. Biol. 5, 447, 2001) Optionally, the suspension may also contain suitable stabilizers or agents, which increase the solubility or stability of the compounds, to allow for the preparation of highly concentrated solutions. Alternatively, the active ingredient may be in powder form for reconstitution with a suitable vehicle, e.g., sterile, pyrogen-free water, before use.

The compounds of the present invention may also be formulated in rectal compositions such as suppositories or retention enemas, using, e.g., conventional suppository bases.

The formulations of the active variants may be administered topically as a gel, ointment, cream, emulsion or sustained release formulation including a transdermal patch. The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

For treating bone or other tissue, for example bone fractures, cartilage defects or tissue repair, administration may be preferred locally by means of a direct injection at or near the site of target or by means of a subcutaneous implant, staples or slow release formulation implanted at or near the target. Suitable devices for direct injection or implantation are biocompatible and maybe matrix-free or comprise a matrix. Matrix-free devices include, in a non-limiting manner, amorphous materials formulated as a paste, putty, viscous liquid or gel. In one embodiment of the present invention formulations of the variant comprise matrix-free devices including Pluronic poloxamers or carboxymethylcellulose (U.S. Pat. No. 6,281,195), polysaccharides or cross-linked polysaccharides (U.S. Pat. No. 6,303,585) and hyaluronic acid (U.S. Pat. No. 6,221,854).

A matrix affords a certain structural component providing a permanent or temporary scaffold for infiltrating cells. It may alternatively provide a scaffold for administration of a variant of the invention to the tissue in need thereof. Release of the variant may controlled. Matrices include, in a non-limiting manner, include collagen compositions (WO 00/47114; U.S. Pat. Nos. 4,394,370 and 5,425,769), polymeric and copolymeric compositions (U.S. Pat. No. 5,650,180), calcium phosphate particle and ceramic compositions (U.S. Pat. No. 6,231,607), including hydroxyapatite compositions (WO 90/01342 and U.S. Pat. Nos. 5,338,772 and 4,795,467), coral, gelatins and demineralized bone. Furthermore, a matrix may be in the form of an implant, a single layer or multilayered composition, sheet, or in particulate form.

A pharmaceutical composition comprising as an active ingredient a variant of the invention in a matrix or matrix-free device may further comprise stabilizers including heparin sulfate or other HSPGs or carriers as those listed above.

A currently preferred embodiment of the present invention provides a method of administering an FGF variant of the present invention, having SEQ ID Nos: 1-7, in combination with a calcium phosphate based matrix to a patient in need thereof.

Pharmaceutical compositions suitable for use in context of the present invention include compositions wherein the active ingredients are contained in an amount effective to achieve the intended purpose. More specifically, a therapeutically effective amount means an amount of a compound effective to prevent, alleviate or ameliorate symptoms of a disease of the subject being treated. Determination of a therapeutically effective amount is well within the capability of those skilled in the art, especially in light of the detailed disclosure provided herein.

Toxicity and therapeutic efficacy of the peptides described herein can be determined by standard pharmaceutical procedures in cell cultures or experimental animals, e.g., by determining the $IC_{50}$ (the concentration which provides 50% inhibition) and the $LD_{50}$ (lethal dose causing death in 50% of the tested animals) for a subject compound. The data obtained from these cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. Depending on the severity and responsiveness of the condition to be treated, dosing can also be a single administration of a slow release composition, with course of treatment lasting from several days to several weeks or until cure is effected or diminution of the disease state is achieved. The amount of a composition to be administered will be dependent on the subject being treated, the severity of the affliction, the manner of administration, the judgment of the prescribing physician, and other factors.

The following example is an illustration only of a method of treating a subject with a variant according to the invention, in order to treat a pathological condition associated with tissue trauma or a related condition, and is not intended to be limiting.

The method includes the step of administering the variant or chimera or fusion protein, in a pharmaceutically acceptable carrier as described above, to a subject to be treated. The medicament is administered according to an effective dosing methodology, preferably until a predefined endpoint is reached, such as a reduction or amelioration of the pathological condition in the subject.

The present invention also relates to methods of treatment of the various pathological conditions described above, by administering to a patient a therapeutically effective amount of the compositions of the present invention. The term administration as used herein encompasses oral, parenteral, intravenous, intramuscular, subcutaneous, transdermal, intrathecal, rectal and intranasal administration.

The present invention further relates to method for the use of the active FGF variants to prepare medicaments useful in inducing bone formation and fracture healing as well as in the detection and treatment of various FGFR-related disorders including skeletal disorders such as achondroplasia and thanatophoric dysplasia and certain types of cancer including but not limited to transitional cell carcinoma (TCC) of the bladder, multiple myeloma, chronic myeloid leukemia (CML) and cervical carcinoma.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification. In addition, citation or identification of any reference in this application shall not be construed as an admission that such reference is available as prior art to the present invention.

The subsequent sequences are preferred embodiments according to the invention. Sequences listed are according to the 155 amino acid isoform of human FGF-2. Those skilled in the art will recognize that the polynucleotide sequences disclosed in SEQ ID NOs:18-32 represent a single allele of the human FGF-2, FGF-4 and FGF-9 genes and polypeptides, and that allelic variation are expected to occur. Allelic variants can be cloned by probing cDNA or genomic libraries or be generated by PCR from total RNA, cDNA or genomic DNA from different individuals according to standard procedures. Allelic variants of the polynucleotide sequence, including those containing silent mutations and those in which mutations result in amino acid sequence changes, are within the scope of the present invention.

The 18 kDa FGF-2 molecule is 155 aa in length when translated from an AUG (methionine) start codon (Abraham et al. EMBO J. 5, 2523, 1986). In addition, there are at least four alternate start codons (CUG, Leu) that provide N-terminal extensions of 41, 46, 55, or 133 aa, resulting in proteins of 22 kDa (196 aa), 22.5 kDa (201 aa), 24 kDa (210 aa) and 34 kDa (288 aa), respectively, having the potential to perform the same function (reviewed in Okada-Ban et al., Int J Biochem Cell Biol, 32, 263, 2000).

The core of approximately 120 amino acids of FGF (amino acids 66-190 of FGF-9, amino acids 30-152 of the 155 aa isoform of FGF-2) has been shown to be crucial for FGF function. Truncations extending within a few amino acids near to or into the core result in reduced biological activity, as determined by proliferation assays. It is now disclosed that FGF variants with reduced biological activity are useful for targeting bioactive agents to specific tissues.

Sequences

The amino acid sequences of the preferred embodiments of the present invention are disclosed as follows:

Amino Acid Sequence of FGF2-N111X
(SEQ ID NO:1)
```
MAAGSITTLP ALPEDGGSGA FPPGHFKDPK RLYCKNGGFF
LRIHPDGRVD GVREKSDPHI KLQLQAEERG VVSIKGVCAN
RYLAMKEDGR LLASKCVTDE CFFFERLESN XYNTYRSRKY
TSWYVALKRT GQYKLGSKTG PGQKAILFLP MSAKS
``` wherein X is other than N and more preferably selected from R or G

Amino Acid Sequence of FGF2-N111R
(SEQ ID NO: 2)
```
MAAGSITTLP ALPEDGGSGA FPPGHFKDPK RLYCKNGGFF
LRIHPDGRVD GVREKSDPHI KLQLQAEERG VVSIKGVCAN
RYLAMKEDGR LLASKCVTDE CFFFERLESN RYNTYRSRKY
TSWYVALKRT GQYKLGSKTG PGQKAILFLP MSAKS
```

Amino Acid Sequence of FGF2-N111G
(SEQ ID NO: 3)
```
MAAGSITTLP ALPEDGGSGA FPPGHFKDPK RLYCKNGGFF
LRIHPDGRVD GVREKSDPHI KLQLQAEERG VVSIKGVCAN
RYLAMKEDGR LLASKCVTDE CFFFERLESN GYNTYRSRKY
TSWYVALKRT GQYKLGSKTG PGQKAILFLP MSAKS
```

Amino Acid Sequence of FGF2(3,5Q)-N111X
(SEQ ID NO: 4)
```
MAQGQITTLP ALPEDGGSGA FPPGHFKDPK RLYCKNGGFF
LRIHPDGRVD GVREKSDPHI KLQLQAEERG VVSIKGVCAN
RYLAMKEDGR LLASKCVTDE CFFFERLESN XYNTYRSRKY
TSWYVALKRT GQYKLGSKTG PGQKAILFLP MSAKS
``` wherein X is other than N and more preferably selected from G or R.

Amino Acid Sequence of FGF2(3,5Q)-N111G
(SEQ ID NO: 5)
```
MAQGQITTLP ALPEDGGSGA FPPGHFKDPK RLYCKNGGFF
LRIHPDGRVD GVREKSDPHI KLQLQAEERG VVSIKGVCAN
RYLAMKEDGR LLASKCVTDE CFFFERLESN GYNTYRSRKY
TSWYVALKRT GQYKLGSKTG PGQKAILFLP MSAKS
```

Amino Acid sequence of human FGF4-N165X 206 aa
(SEQ ID NO: 6)
```
MSGPGTAAVA LLPAVLLALL APWAGRGGAA APTAPNGTLE
AELERRWESL VALSLARLPV AAQPKEAAVQ SGAGDYLLGI
KRLRRLYCNV GIGFHLQALP DGRIGGAHAD TRDSLLELSP
VERGVVSIFG VASRFFVAMS SKGKLYGSPF FTDECTFKEI
LLPNXYNAYE SYKYPGMFIA LSKNGKTKKG NRVSPTMKVT
HFLPRL
``` wherein X is other than N and more preferably G.

Amino acid sequence of human L55M-FGF4-N165X 152 AA
(SEQ ID NO: 7)
```
MARLPV AAQPKEAAVQ SGAGDYLLGI KRLRRLYCNV
GIGFHLQALP DGRIGGAHAD TRDSLLELSP VERGVVSIFG
VASRFFVAMS SKGKLYGSPF FTDECTFKEI LLPNXYNAYE
SYKYPGMFIA LSKNGKTKKG NRVSPTMKVT HFLPRL
``` wherein X is other than N and more preferably G.

```
Amino acid sequence of human W144X-FGF9 208 AA
(SEQ ID NO: 8) disclosed in PCT patent application
WO 02/36732:
MAPLGEVGNY FGVQDAVPFG NVPVLPVDSP VLLSDHLGQS

EAGGLPRGPA VTDLDHLKGI LRRRQLYCRT GFHLEIFPNG

TIQGTRKDHS RFGILEFISI AVGLVSIRGV DSGLYLGMNE

KGELYGSEKL TQECVFREQF EENXYNTYSS NLYKHVDTGR

RYYVALNKDG TPREGTRTKR HQKFTHFLPR PVDPDKVPEL

YKDILSQS
``` wherein X is other than W and more preferably selected from G, R, E or V.

```
Amino Acid sequence of L37M-W144X-FGF9 172 aa
(SEQ ID NO: 9) disclosed in PCT patent application
WO 02/36732:
MGQSEAGGLP RGPAVTDLDH LKGILRRRQL YCRTGFHLEI

FPNGTIQGTR KDHSRFGILE FISIAVGLVS IRGVDSGLYL

GMNEKGELYG SEKLTQECVF REQFEENXYN TYSSNLYKHV

DTGRRYYVAL NKDGTPREGT RTKRHQKFTH FLPRPVDPDK

VPELYKDILS QS
``` wherein X is other than W and more preferably selected from G, R, E or V.

```
Amino Acid sequence of R64M-FGF9 145 aa
(SEQ ID NO: 10) disclosed in PCT patent
application WO 02/36732:
MQLYCRTGFH LEIFPNGTIQ GTRKDHSRFG ILEFISIAVG
LVSIRGVDSG LYLGMNEKGE LYGSEKLTQE CVFREQFEEN
WYNTYSSNLY KHVDTGRRYY VALNKDGTPR EGTRTKRHQK
FTHFLPRPVD PDKVPELYKD ILSQS Amino Acid sequence of R64M-FGF9-W144X 145 aa
                                    (SEQ ID NO: 11)
MQLYCRTGFH LEIFPNGTIQ GTRKDHSRFG ILEFISIAVG
LVSIRGVDSG LYLGMNEKGE LYGSEKLTQE CVFREQFEEN
XYNTYSSNLY KHVDTGRRYY VALNKDGTPR EGTRTKRHQK
FTHFLPRPVD PDKVPELYKD ILSQS
``` wherein X is other than W and more preferably selected from G, R, E or V.

```
Amino Acid sequence of FGF9-2 127 aa
(SEQ ID NO: 12) disclosed in PCT patent
application WO 02/36732:
MQLYCRTGFH LEIFPNGTIQ GTRKDHSRFG ILEFISIAVG
LVSIRGVDSG LYLGMNEKGE LYGSEKLTQE CVFREQFEEN
WYNTYSSNLY KHVDTGRRYY VALNKDGTPR EGTRTKRHQK
FTHFLPR Amino Acid sequence of FGF9-2-W144X 127 aa
                                    (SEQ ID NO: 13)
MQLYCRTGFH LEIFPNGTIQ GTRKDHSRFG ILEFISIAVG
LVSIRGVDSG LYLGMNEKGE LYGSEKLTQE CVFREQFEEN
XYNTYSSNLY KHVDTGRRYY VALNKDGTPR EGTRTKRHQK
FTHFLPR
``` wherein X is other than W and more preferably selected from G, R, E or V.

```
Amino Acid sequence of R64M-FGF9-N143X 145 aa
                                    (SEQ ID NO: 14)
MQLYCRTGFH LEIFPNGTIQ GTRKDHSRFG ILEFISIAVG
LVSIRGVDSG LYLGMNEKGE LYGSEKLTQE CVFREQFEEX

WYNTYSSNLY KHVDTGRRYY VALNKDGTPR EGTRTKRHQK

FTHFLPRPVD PDKVPELYKD ILSQS
``` wherein X is other than N and more preferably S.

```
Amino Acid sequence of FGF9-2-N143X 127 aa
                                    (SEQ ID NO: 15)
MQLYCRTGFH LEIFPNGTIQ GTRKDHSRFG ILEFISIAVG

LVSIRGVDSG LYLGMNEKGE LYGSEKLTQE CVFREQFEEX

WYNTYSSNLY KHVDTGRRYY VALNKDGTPR EGTRTKRHQK

FTHFLPR
``` wherein X is other than N and more preferably S.

```
Amino Acid sequence of FGF9-2-W144X-CNP(1-22)
                                    (SEQ ID NO: 16)
MQLYCRTGFH LEIFPNGTIQ GTRKDHSRFG ILEFISIAVG

LVSIRGVDSG LYLGMNEKGE LYGSEKLTQE CVFREQFEEN

XYNTYSSNLY KHVDTGRRYY VALNKDGTPR EGTRTKRHQK

FTHFLPRGGG GLSKGCFGLK LDRIGSMSGL GC
``` wherein X is other than W and more preferably selected from G, R, E or V.

```
Amino Acid sequence of CNP(1-22)-FGF9-2-W144X
                                    (SEQ ID NO: 17)
MGLSKGCFGL KLDRIGSMSG LGCGGGGGGG GQLYCRTGFH

LEIFPNGTIQ GTRKDHSRFG ILEFISIAVG LVSIRGVDSG

LYLGMNEKGE LYGSEKLTQE CVFREQFEEN XYNTYSSNLY

KHVDTGRRYY VALNKDGTPR EGTRTKRHQK FTHFLPR
```

The corresponding polynucleotide sequences are as follows:

```
Sequence of FGF2-N111X DNA
                                    (SEQ ID NO: 18)
ATGGCTGCCG GGAGCATCAC CACGCTGCCC GCCCTTCCGG

AGGATGGCGG CAGCGGCGCC TTCCCGCCCG GCACTTCAA

GGACCCCAAG CGGCTGTACT GCAAAAACGG GGGCTTCTTC

CTGCGCATCC ACCCCGACGG CCGAGTTGAC GGGGTCCGGG

AGAAGAGCGA CCCTCACATC AAGCTACAAC TTCAAGCAGA

AGAGAGAGGA GTTGTGTCTA TCAAAGGAGT GTGTGCTAAC

CGGTACCTGG CTATGAAGGA AGATGGAAGA TTACTGGCTT

CTAAATGTGT TACGGATGAG TGTTTCTTTT TTGAACGATT

GGAATCTAAT NNNTACAATA CTTACCGGTC TAGAAAATAC

ACCAGTTGGT ATGTGGCATT GAAACGAACT GGGCAGTATA

AACTTGGTTC CAAAACAGGA CCTGGGCAGA AAGCTATACT

TTTTCTTCCA ATGTCTGCTA AGAGCTGA
``` wherein NNN is other than a codon coding for Asn (AAT or AAC) or a stop codon and is more preferably a codon coding for amino acid Gly or Arg.

Sequence of FGF2-N111G DNA
(SEQ ID NO: 19)
ATGGCTGCCG GGAGCATCAC CACGCTGCCC GCCCTTCCGG

AGGATGGCGG CAGCGGCGCC TTCCCGCCCG GGCACTTCAA

GGACCCCAAG CGGCTGTACT GCAAAAACGG GGGCTTCTTC

CTGCGCATCC ACCCCGACGG CCGAGTTGAC GGGGTCCGGG

AGAAGAGCGA CCCTCACATC AAGCTACAAC TTCAAGCAGA

AGAGAGAGGA GTTGTGTCTA TCAAAGGAGT GTGTGCTAAC

CGGTACCTGG CTATGAAGGA AGATGGAAGA TTACTGGCTT

CTAAATGTGT TACGGATGAG TGTTTCTTTT TTGAACGATT

GGAATCTAAT NNNTACAATA CTTACCGGTC TAGAAAATAC

ACCAGTTGGT ATGTGGCATT GAAACGAACT GGGCAGTATA

AACTTGGTTC CAAAACAGGA CCTGGGCAGA AAGCTATACT

TTTTCTTCCA ATGTCTGCTA AGAGCTGA wherein NNN is a codon coding for amino acid Gly (GGT, GGC, GGA, GGG).

Sequence of FGF2-N111R DNA
(SEQ ID NO: 20)
ATGGCTGCCG GGAGCATCAC CACGCTGCCC GCCCTTCCGG

AGGATGGCGG CAGCGGCGCC TTCCCGCCCG GGCACTTCAA

GGACCCCAAG CGGCTGTACT GCAAAAACGG GGGCTTCTTC

CTGCGCATCC ACCCCGACGG CCGAGTTGAC GGGGTCCGGG

AGAAGAGCGA CCCTCACATC AAGCTACAAC TTCAAGCAGA

AGAGAGAGGA GTTGTGTCTA TCAAAGGAGT GTGTGCTAAC

CGGTACCTGG CTATGAAGGA AGATGGAAGA TTACTGGCTT

CTAAATGTGT TACGGATGAG TGTTTCTTTT TTGAACGATT

GGAATCTAAT CGNTACAATA CTTACCGGTC TAGAAAATAC

ACCAGTTGGT ATGTGGCATT GAAACGAACT GGGCAGTATA

AACTTGGTTC CAAAACAGGA CCTGGGCAGA AAGCTATACT

TTTTCTTCCA ATGTCTGCTA AGAGCTGA wherein N is selected from A, C, G or T

Sequence of FGF2(3Q5Q)-N111X DNA
(SEQ ID NO: 21)
ATGGCTCAXG GGCAXATCAC CACGCTGCCC GCCCTTCCGG

AGGATGGCGG CAGCGGCGCC TTCCCGCCCG GGCACTTCAA

GGACCCCAAG CGGCTGTACT GCAAAAACGG GGGCTTCTTC

CTGCGCATCC ACCCCGACGG CCGAGTTGAC GGGGTCCGGG

AGAAGAGCGA CCCTCACATC AAGCTACAAC TTCAAGCAGA

AGAGAGAGGA GTTGTGTCTA TCAAAGGAGT GTGTGCTAAC

CGGTACCTGG CTATGAAGGA AGATGGAAGA TTACTGGCTT

CTAAATGTGT TACGGATGAG TGTTTCTTTT TTGAACGATT

GGAATCTAAT NNNTACAATA CTTACCGGTC TAGAAAATAC

ACCAGTTGGT ATGTGGCATT GAAACGAACT GGGCAGTATA

AACTTGGTTC CAAAACAGGA CCTGGGCAGA AAGCTATACT

TTTTCTTCCA ATGTCTGCTA AGAGCTGA wherein nucleotides 9 and 15 are independently chosen from A or G and the codon encoded by NNN AT POSITION 331-333 is other than a codon coding for Asn (AAT or AAC) or a stop codon and is more preferably encodes for amino acid Gly or Arg.

Sequence of FGF2(3Q5Q)-N111G DNA
(SEQ ID NO: 22)
ATGGCTCAXG GGCAXATCAC CACGCTGCCC GCCCTTCCGG

AGGATGGCGG CAGCGGCGCC TTCCCGCCCG GGCACTTCAA

GGACCCCAAG CGGCTGTACT GCAAAAACGG GGGCTTCTTC

CTGCGCATCC ACCCCGACGG CCGAGTTGAC GGGGTCCGGG

AGAAGAGCGA CCCTCACATC AAGCTACAAC TTCAAGCAGA

AGAGAGAGGA GTTGTGTCTA TCAAAGGAGT GTGTGCTAAC

CGGTACCTGG CTATGAAGGA AGATGGAAGA TTACTGGCTT

CTAAATGTGT TACGGATGAG TGTTTCTTTT TTGAACGATT

GGAATCTAAT GGNTACAATA CTTACCGGTC TAGAAAATAC

ACCAGTTGGT ATGTGGCATT GAAACGAACT GGGCAGTATA

AACTTGGTTC CAAAACAGGA CCTGGGCAGA AAGCTATACT

TTTTCTTCCA ATGTCTGCTA AGAGCTGA wherein nucleotides 9 and 15 are independently chosen from A or G and the N at position 333 is selected from A, C, G or T.

Sequence of FGF4-N165X DNA
(SEQ ID NO: 23)
ATGTCGGGGC CCGGACGGC CGCGGTAGCG CTGCTCCCGG

CGGTCCTGCT GGCCTTGCTG GCGCCCTGGG CGGGCCGAGG

GGGCGCCGCC GCACCCACTG CACCCAACGG CACGCTGGAG

GCCGAGCTGG AGCGCCGCTG GGAGAGCCTG GTGGCGCTCT

CGTTGGCGCG CCTGCCGGTG GCAGCGCAGC CCAAGGAGGC

GGCCGTCCAG AGCGGCGCCG GCGACTACCT GCTGGGCATC

AAGCGGCTGC GGCGGCTCTA CTGCAACGTG GGCATCGGCT

TCCACCTCCA GGCGCTCCCC GACGGCCGCA TCGGCGGCGC

GCACGCGGAC ACCCGCGACA GCCTGCTGGA GCTCTCGCCC

GTGGAGCGGG GCGTGGTGAG CATCTTCGGC GTGGCCAGCC

GGTTCTTCGT GGCCATGAGC AGCAAGGGCA AGCTCTATGG

CTCGCCCTTC TTCACCGATG AGTGCACGTT CAAGGAGATT

CTCCTTCCCA ACXXXTACAA CGCCTACGAG TCCTACAAGT

ACCCCGGCAT GTTCATCGCC CTGAGCAAGA ATGGGAAGAC

CAAGAAGGGG AACCGAGTGT CGCCCACCAT GAAGGTCACC

CACTTCCTCC CCAGGCTG wherein XXX is other than a codon coding for Asn (AAT or AAC) or a stop codon and is more preferably ecodes for amino acid Gly (GGA, GGC, GGQ GGT).

Sequence of L55M-FGF4-N165X DNA
(SEQ ID NO: 24)
ATGGCGCGCC TGCCGGTGGC AGCGCAGCCC AAGGAGGCGG

CCGTCCAGAG CGGCGCCGGC GACTACCTGC TGGGCATCAA

GCGGCTGCGG CGGCTCTACT GCAACGTGGG CATCGGCTTC

CACCTCCAGG CGCTCCCCGA CGGCCGCATC GGCGGCGCGC

ACGCGGACAC CCGCGACAGC CTGCTGGAGC TCTCGCCCGT

GGAGCGGGGC GTGGTGAGCA TCTTCGGCGT GGCCAGCCGG

TTCTTCGTGG CCATGAGCAG CAAGGGCAAG CTCTATGGCT

CGCCCTTCTT CACCGATGAG TGCACGTTCA AGGAGATTCT

CCTTCCCAAC GGNTACAACG CCTACGAGTC CTACAAGTAC

CCCGGCATGT TCATCGCCCT GAGCAAGAAT GGGAAGACCA

AGAAGGGGAA CCGAGTGTCG CCCACCATGA AGGTCACCCA

CTTCCTCCCC AGGCTG wherein N is selected from A, C, G or T.

Sequence of R64M-FGF9 DNA (SEQ ID NO: 25)
disclosed in PCT application WO 02/36732
A
TGCAGCTATA CTGCAGGACT GGATTTCACT TAGAAATCTT

CCCCAATGGT ACTATCCAGG GAACCAGGAA AGACCACAGC

CGATTTGGCA TTCTGGAATT TATCAGTATA GCAGTGGGCC

TGGTCAGCAT TCGAGGCGTG GACAGTGGAC TCTACCTCGG

GATGAATGAG AAGGGGGAGC TGTATGGATC AGAAAAACTA

ACCCAAGAGT GTGTATTCAG AGAACAGTTC GAAGAAAACT

GGTATAATAC GTACTCGTCA AACCTATATA AGCACGTGGA

CACTGGAAGG CGATACTATG TTGCATTAAA TAAAGATGGG

ACCCCGAGAG AAGGGACTAG GACTAAACGG CACCAGAAAT

TCACACATTT TTTACCTAGA CCAGTGGACC CCGACAAAGT

ACCTGAACTG TATAAGGATA TTCTAAGCCA AAGTTGA

Sequence of R64M-FGF9-W144X DNA
(SEQ ID NO: 26)
A
TGCAGCTATA CTGCAGGACT GGATTTCACT TAGAAATCTT

CCCCAATGGT ACTATCCAGG GAACCAGGAA AGACCACAGC

CGATTTGGCA TTCTGGAATT TATCAGTATA GCAGTGGGCC

TGGTCAGCAT TCGAGGCGTG GACAGTGGAC TCTACCTCGG

GATGAATGAG AAGGGGGAGC TGTATGGATC AGAAAAACTA

ACCCAAGAGT GTGTATTCAG AGAACAGTTC GAAGAAAACN

NNTATAATAC GTACTCGTCA AACCTATATA AGCACGTGGA

CACTGGAAGG CGATACTATG TTGCATTAAA TAAAGATGGG

ACCCCGAGAG AAGGGACTAG GACTAAACGG CACCAGAAAT

TCACACATTT TTTACCTAGA CCAGTGGACC CCGACAAAGT

ACCTGAACTG TATAAGGATA TTCTAAGCCA AAGTTGA wherein NNN is other than a codon coding for Trp (TGG) or a stop codon (TAA, TAG or TGA) and is more preferably a codon coding for amino acid Gly, Arg, Val or Glu.

Sequence of FGF9-2 DNA (SEQ ID NO: 27)
disclosed in PCT application WO 02/36732
A
TGCAGCTATA CTGCAGGACT GGATTTCACT TAGAAATCTT

CCCCAATGGT ACTATCCAGG GAACCAGGAA AGACCACAGC

CGATTTGGCA TTCTGGAATT TATCAGTATA GCAGTGGGCC

TGGTCAGCAT TCGAGGCGTG GACAGTGGAC TCTACCTCGG

GATGAATGAG AAGGGGGAGC TGTATGGATC AGAAAAACTA

ACCCAAGAGT GTGTATTCAG AGAACAGTTC GAAGAAAACT

GGTATAATAC GTACTCGTCA AACCTATATA AGCACGTGGA

CACTGGAAGG CGATACTATG TTGCATTAAA TAAAGATGGG

ACCCCGAGAG AAGGGACTAG GACTAAACGG CACCAGAAAT

TCACACATTT TTTACCTAGA TGA

Sequence of FGF9-2-W144X DNA
(SEQ ID NO: 28)
A
TGCAGCTATA CTGCAGGACT GGATTTCACT TAGAAATCTT

CCCCAATGGT ACTATCCAGG GAACCAGGAA AGACCACAGC

CGATTTGGCA TTCTGGAATT TATCAGTATA GCAGTGGGCC

TGGTCAGCAT TCGAGGCGTG GACAGTGGAC TCTACCTCGG

GATGAATGAG AAGGGGGAGC TGTATGGATC AGAAAAACTA

ACCCAAGAGT GTGTATTCAG AGAACAGTTC GAAGAAAACN

NNTATAATAC GTACTCGTCA AACCTATATA AGCACGTGGA

CACTGGAAGG CGATACTATG TTGCATTAAA TAAAGATGGG

ACCCCGAGAG AAGGGACTAG GACTAAACGG CACCAGAAAT

TCACACATTT TTTACCTAGA TGA wherein NNN is other than a codon coding for Trp (TGG) or a stop codon (TAA, TAG or TGA) and is more preferably a codon coding for amino acid Gly, Arg, Val or Glu.

Sequence of R64M-FGF9-N143X DNA
(SEQ ID NO: 29)
A
TGCAGCTATA CTGCAGGACT GGATTTCACT TAGAAATCTT

CCCCAATGGT ACTATCCAGG GAACCAGGAA AGACCACAGC

CGATTTGGCA TTCTGGAATT TATCAGTATA GCAGTGGGCC

TGGTCAGCAT TCGAGGCGTG GACAGTGGAC TCTACCTCGG

GATGAATGAG AAGGGGGAGC TGTATGGATC AGAAAAACTA

ACCCAAGAGT GTGTATTCAG AGAACAGTTC GAAGAANNNT

GGTATAATAC GTACTCGTCA AACCTATATA AGCACGTGGA

CACTGGAAGG CGATACTATG TTGCATTAAA TAAAGATGGG

ACCCCGAGAG AAGGGACTAG GACTAAACGG CACCAGAAAT

TCACACATTT TTTACCTAGA CCAGTGGACC CCGACAAAGT

ACCTGAACTG TATAAGGATA TTCTAAGCCA AAGTTGA wherein NNN is other than a codon coding for Asn (AAT, AAC) or a stop codon (TAA, TAG or TGA) and is more preferably a codon coding for amino acid Ser.

Sequence of FGF9-2-N143X DNA
(SEQ ID NO: 30)
A

TGCAGCTATA CTGCAGGACT GGATTTCACT TAGAAATCTT

CCCCAATGGT ACTATCCAGG GAACCAGGAA AGACCACAGC

CGATTTGGCA TTCTGGAATT TATCAGTATA GCAGTGGGCC

TGGTCAGCAT TCGAGGCGTG GACAGTGGAC TCTACCTCGG

GATGAATGAG AAGGGGGAGC TGTATGGATC AGAAAAACTA

ACCCAAGAGT GTGTATTCAG AGAACAGTTC GAAGAANNNT

GGTATAATAC GTACTCGTCA AACCTATATA AGCACGTGGA

CACTGGAAGG CGATACTATG TTGCATTAAA TAAAGATGGG

ACCCCGAGAG AAGGGACTAG GACTAAACGG CACCAGAAAT

TCACACATTT TTTACCTAGA TGA wherein NNN is other than a codon coding for Asn (AAT, AAC) or a stop codon (TAA, TAG or TGA) and is more preferably a codon coding for amino acid Ser.

Sequence of FGF9-2-W144X-CNP(1-22) DNA
(SEQ ID NO: 31)
A

TGCAGCTATA CTGCAGGACT GGATTTCACT TAGAAATCTT

CCCCAATGGT ACTATCCAGG GAACCAGGAA AGACCACAGC

CGATTTGGCA TTCTGGAATT TATCAGTATA GCAGTGGGCC

TGGTCAGCAT TCGAGGCGTG GACAGTGGAC TCTACCTCGG

GATGAATGAG AAGGGGGAGC TGTATGGATC AGAAAAACTA

ACCCAAGAGT GTGTATTCAG AGAACAGTTC GAAGAAACN

NNTATAATAC GTACTCGTCA AACCTATATA AGCACGTGGA

CACTGGAAGG CGATACTATG TTGCATTAAA TAAAGATGGG

ACCCCGAGAG AAGGGACTAG GACTAAACGG CACCAGAAAT

TCACACATTT TTTACCTAGA GGAGGGGGAG GTCTGTCCAA

AGGTTGCTTC GGCCTCAAGC TGGACCGAAT CGGCTCCATG

AGCGGCCTGG GATGT wherein NNN is other than a codon coding for Trp (TGG) or a stop codon (TAA, TAG or TGA) and is more preferably a codon coding for amino acid Gly, Arg, Val or Glu.

Sequence of CNP(1-22-FGF9-2-W144X DNA
(SEQ ID NO: 32)
ATGGGTCTGT CCAAAGGTTG CTTCGGCCTC AAGCTGGACC

GAATCGGCTC CATGAGCGGC CTGGGATGCG GAGGGGGAGG

GGGAGGGGGA GGGCAGCTAT ACTGCAGGAC TGGATTTCAC

TTAGAAATCT TCCCCAATGG TACTATCCAG GAACCAGGA

AAGACCACAG CCGATTTGGC ATTCTGGAAT TTATCAGTAT

AGCAGTGGGC CTGGTCAGCA TTCGAGGCGT GGACAGTGGA

CTCTACCTCG GGATGAATGA GAAGGGGGAG CTGTATGGAT

CAGAAAAACT AACCCAAGAG TGTGTATTCA GAGAACAGTT

CGAAGAAAAC NNNTATAATA CGTACTCGTC AAACCTATAT

AAGCACGTGG ACACTGGAAG GCGATACTAT GTTGCATTAA

ATAAAGATGG GACCCCGAGA GAAGGGACTA GGACTAAACG

GCACCAGAAA TTCACACATT TTTTACCTAG A wherein NNN is other than a codon coding for Trp (TGG) or a stop codon (TAA, TAG or TGA) and is more preferably a codon coding for amino acid Gly, Arg, Val or Glu.

The principles of the invention are demonstrated by means of the following non-limitative examples.

Example 1

Expression of FGF Variants Using High Expression System

Construction of the p89Bluescript (p89BS) Construct

Construction of p89BS was performed as described in copending WO 02/022779. The genes encoding the proteins of the present invention were ligated into the NdeI-BamHI digest of the p89BS construct and transformed into E. coli cells, such as JM109, TG1, TG2, DHα, and XL1blue.

Construction of FGF Variants

Construction of the FGF-2, FGF-4 and FGF-9 variants was performed using the polymerase chain reaction (PCR) technique. Three constitutive PCR reactions were performed, where the variation or variations were introduced into the gene by amplifying DNA fragments from both ends of the mutation site(s).

The primers and protocol used for the human FGF-2 variants were as follows:

(SEQ ID NO: 58)
HF2-for      5'GGAATTCCATATGGCTGAAGGGGAAATC (SEQ ID NO: 59)
HF2-rev      5'CGGGATCCTCAGCTCTTAGCAG (SEQ ID NO: 60)
N111G-for    5'GATTGGAATCTAATGGCTACAATACTTAC (SEQ ID NO: 61)
N111G-rev    5'GTAAGTATTGTAGCCATTAGATTCCAATC (SEQ ID NO: 62)
N111R-for    5'GATTGGAATCTAATCGCTACAATACTTAC -continued

```
                                             (SEQ ID NO: 63)
N111R-rev   5'GTAAGTATTGTAGCGATTAGATTCCAATC (SEQ ID NO: 64)
3,5Q-for    5'GGAATTCCATATGGCTCAAGGGCAAATCACCACGCTG
```

(CATATG—NdeI, GGATCC—BamHI, GAATTC—EcoRI Restriction Sites for Cloning)

1. PCR for 5' domain: The following primers were used: HF2-for or 3Q5Q-for and N111G/R-rev
   PCR for 3' domain: The following primers were used: N111G/R-for and HF2-rev on the template of human FGF-2 (hFGF2) cloned into the p80Bs vector.
2. For the entire gene the following primers were used: HF2-for or 3,5Q-for and HF2-rev on the DNA from the 5' and 3' domains, above.

The primers and protocol, as disclosed in PCT patent application WO 02/36732, used to prepare the human FGF-9 variants were as follows:

```
                                             (SEQ ID NO: 65)
W144G-for   5'- CGAAGAAAACGGGTATAATACGTAC (SEQ ID NO: 66)
W144G-back  5'- GTACGTATTATACCCGTTTTCTTCG (SEQ ID NO: 67)
W144R-for   5'- CGAAGAAAACCGGTATAATACG (SEQ ID NO: 68)
W144R-back  5'- CGTATTATACCGGTTTTCTTCG (SEQ ID NO: 69)
W144V-for   5'- CGAAGAAAACGTGTATAATACG (SEQ ID NO: 70)
W144V-back  5'- CGTATTATACACGTTTTCTTCG (SEQ ID NO: 71)
W144E-for   5'- CGAAGAAAACGAGTATAATACG (SEQ ID NO: 72)
W144E-back  5'- CGTATTATACTCGTTTTCTTCG (SEQ ID NO: 73)
W144A-for   5'- CGAAGAAAACGCGTATAATACG (SEQ ID NO: 74)
W144A-back  5'- CGTATTATACGCGTTTTCTTCG (SEQ ID NO: 75)
W144N-for   5'- CGAAGAAAACAATTATAATACG (SEQ ID NO: 76)
W144N-back  5'- CGTATTATAATTGTTTTCTTCG (SEQ ID NO: 77)
FGF9-Stopback  5'AGCTGGATCCTCAACTTTGGCTTAGAATATCC (SEQ ID NO: 78)
R64M-FGF9-for  5'GGGAATTCCATATGCAGCTATACTGCAGGACTG (SEQ ID NO: 79)
N143S-for   5'-GTTCGAAGAAAGCTGGTATAATATACG (SEQ ID NO: 80)
N143S-back  5'-CGTATTATACCAGCTTTCTTCGAAC
```

For example:
W144G-for codes for the 5' to 3' sequence of the mutation Trp 144 into Gly in FGF-9.
W144G-back codes for the 3' to 5' sequence of the mutation Trp 144 into Gly in FGF-9.
W144R-for codes for the 5' to 3' sequence of the mutation Trp 144 into Arg in FGF-9.
W144R-back codes for the 3' to 5' sequence of the mutation Trp144 into Arg in FGF-9.
N143S-for codes for the 5' to 3' sequence of the mutation Asn143 into Ser in FGF-9.
N143 S-for codes for the 3' to 5' sequence of the mutation Asn143 into Ser in FGF-9.

The PCR conditions were as follows: annealing temperature was 54° C. followed by elongation at 72° C. for 30 cycles. The purified PCR fragment was digested with NdeI and BamHI, and ligated into the p89BS vector.

FGF-4 Variant

To synthesize the human FGF-4 variants, FGF4-N165G and L55M-FGF4-N165G combinations of the following PCR primers were used:

```
                                             (SEQ ID NO: 81)
L55M-hF4-for  5'ACGTCATATGTTGGCGCGCCTGCCGGTG (SEQ ID NO: 82)
hF4-rev       5'ACGTGGATCCTCACAGCCTGGGGAGGAAG (SEQ ID NO: 83)
N165R-for     5'GATTCTCCTTCCCAACAGGTACAACGCCTACGAG (SEQ ID NO: 84)
N165R-rev     5'CTCGTAGGCGTTGTACCTGTTGGGAAGGAGAATC
```

L55M-hF4-for and N165G-rev were used to amplify the 5' domain of human FGF-4 and incorporate an Met at position 55 and a Gly at position 165. The hF4-rev and N165G-for primers were used to amplify the 3' domain of FGF-4 and incorporate the Gly at position 165. The amplified fragments were combined and serve as a template for an additional PCR reaction using L55M-F4-for and hF4-rev. The PCR conditions were as follows: 8 cycles with annealing at 50° C., elongation at 72° C. followed by 17 cycles with annealing at 60° C., elongation at 72° C. The PCR fragment was digested with NdeI and BamHI, gel purified and ligated into the p80BS vector. The bold, underlined bases in SEQ ID NO: 81 encode the substituted amino acid.

Protein Purification

The newly constructed expression plasmids were transfected into competent JM109 bacteria, plated on 2YT-agar plates supplemented with 200 ug/ml ampicillin and left to grow ON (overnight) at 37° C. A single colony was grown ON at 37° C. in a two-liter flask containing 330 ml of TB125 medium (Tryptone 15 gr/L, Yeast extract 30 gr/L, $KH_2PO_4$ 2.31 gr/L, $K_2HPO_4$ 12.5 gr/L, Glycerol 5 gr/L) supplemented with 200 ug/ml ampicillin. The bacterial suspension was centrifuged at 4000 rpm (4° C.) for 15 minutes, and the medium was discarded. The bacterial pellet was then suspended in 25 ml of 1×PBS buffer containing protease inhibitors, sonicated on ice, and centrifuged at 10,000 rpm (4° C.) for 15 minutes. The protein supernatant was collected, and 3 ml of Heparin-Sepharose® beads slurry was added and shaken gently for 6 hours at 4° C. The beads were loaded onto a column, washed extensively with PBS buffer containing 0.3M NaCl, and eluted in 7 ml PBS containing 2-2.5M NaCl. The FGF variant proteins were then dialyzed against 1×PBS and repurified on FPLC using a heparin Sepharose® column (HiTrap® Heparin, Amersham Pharmacia biotech) with a 0-2.5M NaCl (in PBS-0.05% CHAPS) linear gradient in the same dialysis buffer. The purified proteins were later stored at −70° C. Note that the FGF-9 variants were eluted with 2.5 M NaCl, while the FGF-2 variants were eluted with 2 M NaCl.

Example 2

Preparation of Truncated FGF Variants

The truncated mutants were prepared by PCR, where exemplary primers used are listed herein below:

```
35421    5'-GGCCCTAGGTCATCTAGGTAAAAAATGTGTG                    (SEQ ID NO: 85)

35422    5'-GGGAATTCCATATGCAGCTATACTGCAGGACTG                  (SEQ ID NO: 86)

29522    5'-AGCTGGATCCTCAACTTTGGCTTAGAATATCC                   (SEQ ID NO: 87)

40869    5'-CGATACGTACATATGCACTTAGAAATCTTC                    (SEQ ID NO: 88)
```

Where:

35421 was used to introduce stop codon (Pro191Stop) and a BamHI restriction enzyme site for the construction of the FGF9-2 and FGF9-L72M variants;

35422 was used to introduce the start codon and an NdeI restriction enzyme site for the construction of the R64M-FGF9 and FGF9-2 variants;

29522 was used to introduce the start codon (R64M) and a Bam HI restriction site for the construction of the R64M-FGF9 variant;

40869 was used to introduce a start codon (L72M) and a BamHI restriction enzyme site for the construction of the FGF9-L72M variant.

The new mutant PCR fragments synthesized in methods known in the art, were digested with restriction enzymes Nde I and BamHI and cloned in p89BS, forming DNA constructs which were introduced into electrocompetent E. coli TG-1 cells.

Figure 5A:
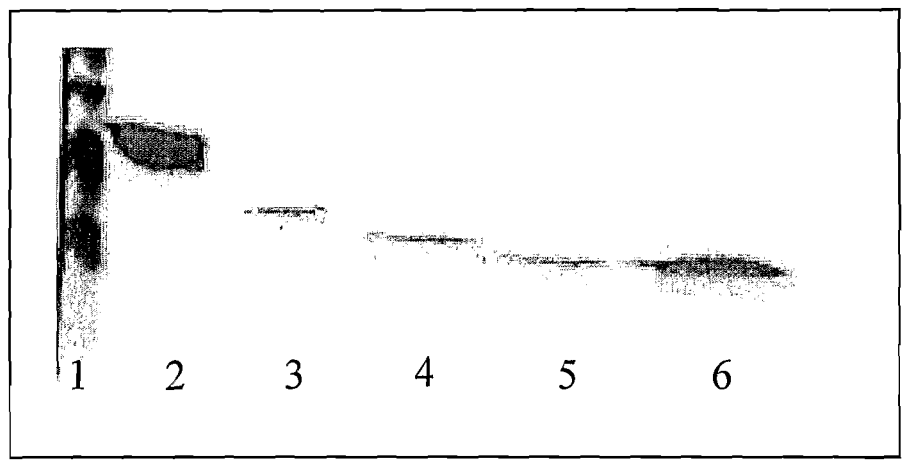
FIG. 5A displays the electrophoresis pattern of FGF-9 variants on SDS-PAGE.
Figure 5B:
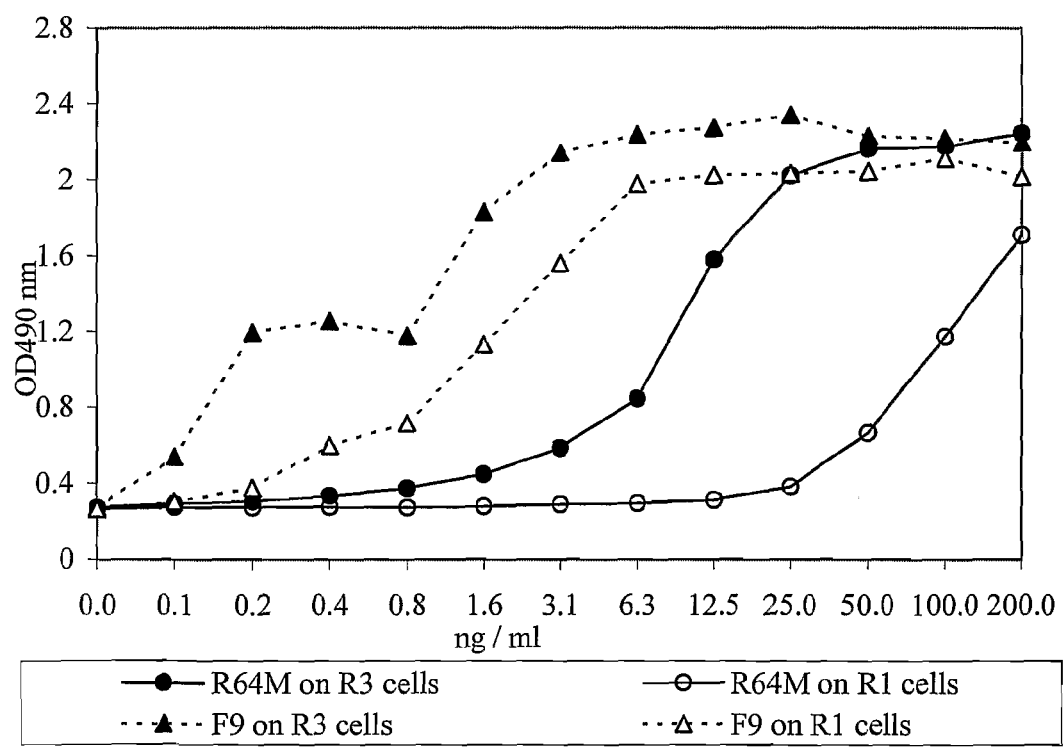
FIG. 5B shows the reduced mitogen activity of the truncated FGF-9 variants.

FIG. 5A depicts the electrophoretic pattern of several of the preferred variants on SDS-PAGE. Lane 1 contains molecular weight markers [Lysozyme (20.7 kDa), Soybean trypsin inhibitor (28.8 kDa), Carbonic anhydrase (34.3 kDa), Ovalbumin (50 kDa)]; Lane 2 contains native FGF-9; Lane 3 contains a 172 aa variant; Lane 4 contains a 164 aa variant; Lane 5 contains the R64M-FGF9 (145 aa) variant; Lane 6 contains the FGF9-2 variant.

Example 3

FGF Variant Binding to FGFR-Transfected FDCP Cell Lines

The FDCP cell line is a murine immortalized, interleukin 3 (IL-3)-dependent cell line of myelocytic bone marrow origin that does not express endogenous FGF Receptors (FGFR). Upon transfection with FGFR cDNA, the FDCP cell line exhibits a dose-dependent proliferative response to FGF that can replace the dependence on IL-3. FGFR transfected FDCP cells can therefore be used to screen variant FGFs for specific inhibitors, activators or for FGFR signaling. FDCP cells response to various ligands is quantitated by a cell proliferation assay with XTT reagent (Cell Proliferation Kit, Biological Industries Co.). The method is based on the capability of mitochondrial enzymes to reduce tetrazolium salts into a colorogenic compound, which can be quantitated and is indicative of cell viability.

Specifically, FDCP cells stably expressing FGFR3-IIIc, FGFR3-IIIb isoforms, FGFR2IIIc or FGFR1 were grown in "full medium" (Iscove's Medium containing 2 ml glutamine, 10% FCS, 100 ug/ml penicillin, 100 ug/ml streptomycin) supplemented with 5 ug/ml heparin and 10 ng/ml FGF. Cells were split every 3 days and kept in culture for up to one month. One day prior to the experiment the cells were split. Before the experiment the cells were washed 3 times (1000 rpm, 6 min) with full medium. The cells were resuspended and counted with Trypan Blue. Twenty thousand ($2\times10^4$) cells were added to each well of 96-well plate in 50 ul full medium containing heparin. Conditioned medium containing FGF wild type parent or variants at varying concentrations with heparin was added in an additional volume of 50 ul full medium to bring the final volume to 100 ul. The plate was incubated for 48 hours at 37° C. To assay cell proliferation, 100 ul of PMS reagent was added to 5 ml of XTT reagent and mixed well (according to manufacturer's protocol). 50 ul of the latter solution were aliquoted into each well, and the plates incubated at 37° C. for 4 hours and the color developed was read by a spectro-ELISA reader at $A_{490nm}$.

In these experiments FDCP cells expressing the FGFR3 isoforms FGFR#IIIb and FGFR3IIIc, FGFR2 or FGFR1 were grown in the presence of varying concentrations of the FGF-2 and FGF-4 variants.

Results

FIGS. 1A, 1B, 2A and 3 depict the mitogenicity level and receptor specificity of a sample of the variants of the invention. Wild type (native, parent) FGF-2 or FGF-4 are present as control in the assays.

Figure 1A:
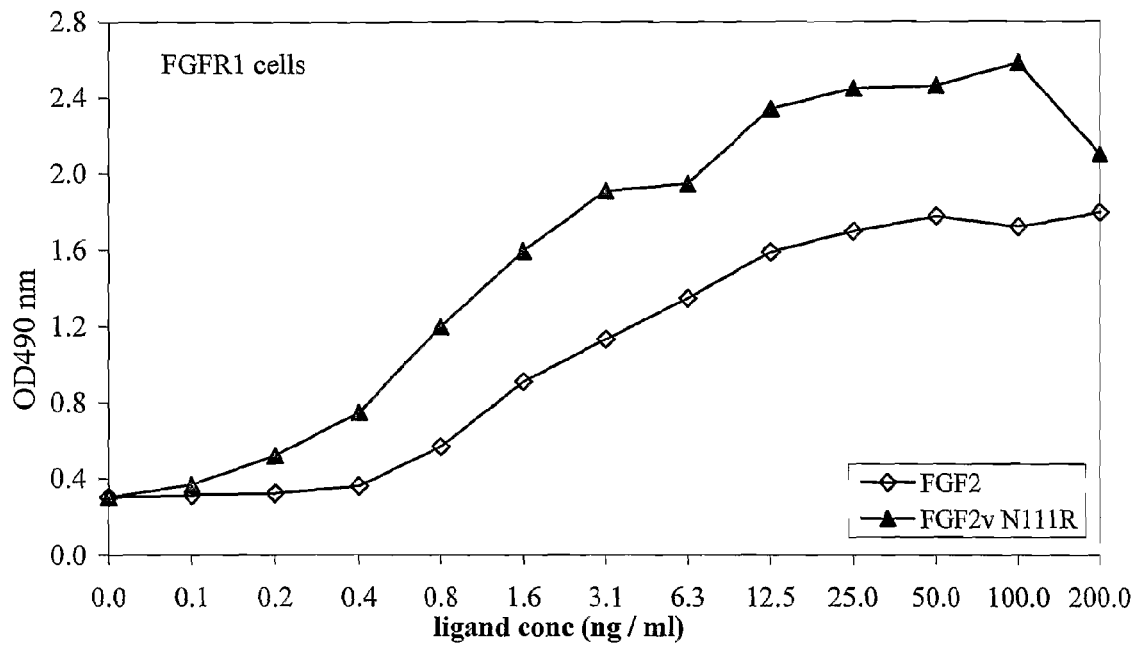
FIGS. 1A and 1B show the proliferative activity of FGF2-N111R.
Figure 1B:
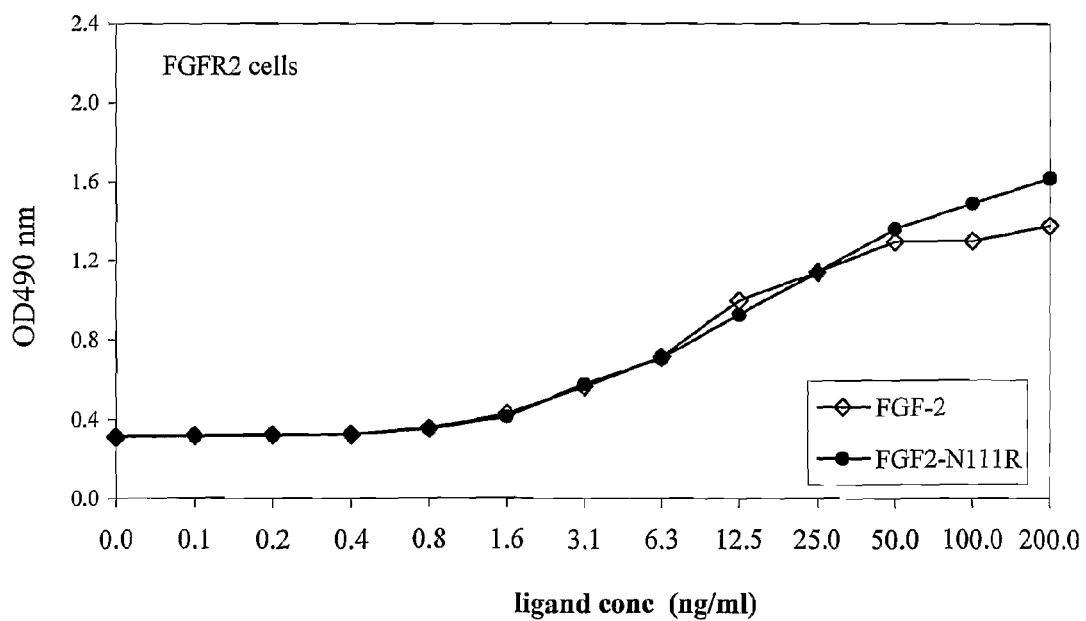

FIGS. 1A and 1B show the increase in mitogenicity afforded by the FGF2-N111R variant on FGFR1 and FGFR2 expressing cells.

Figure 2A:
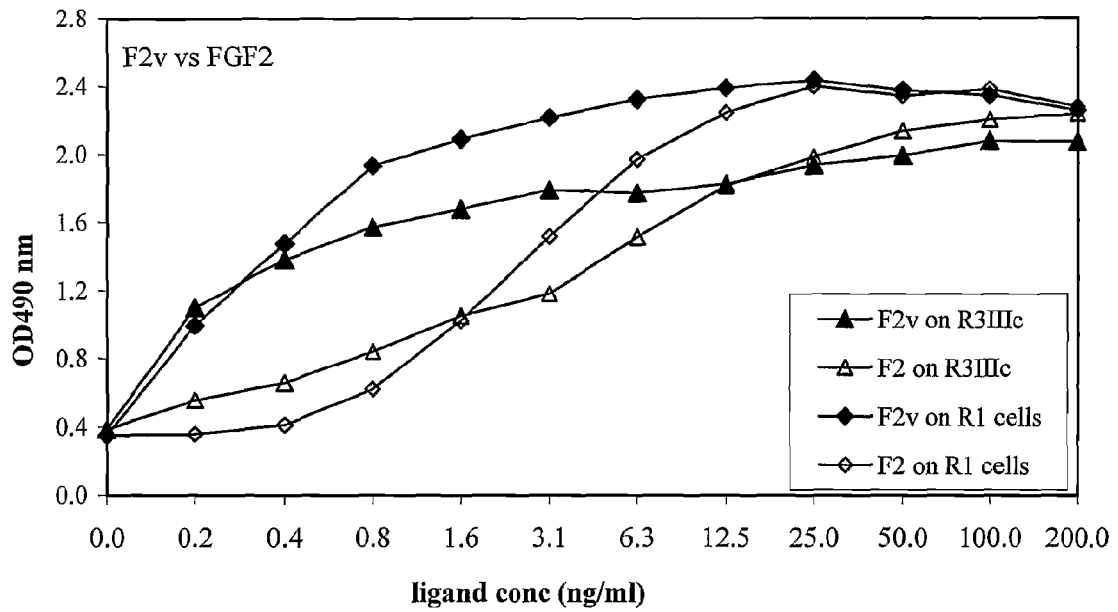
FIGS. 2A and 2B show the mitogenic activity induced by the FGF-2 variant, FGF2(3,5Q)-N111G on FGFR-transfected FDCP cells.
Figure 2B:
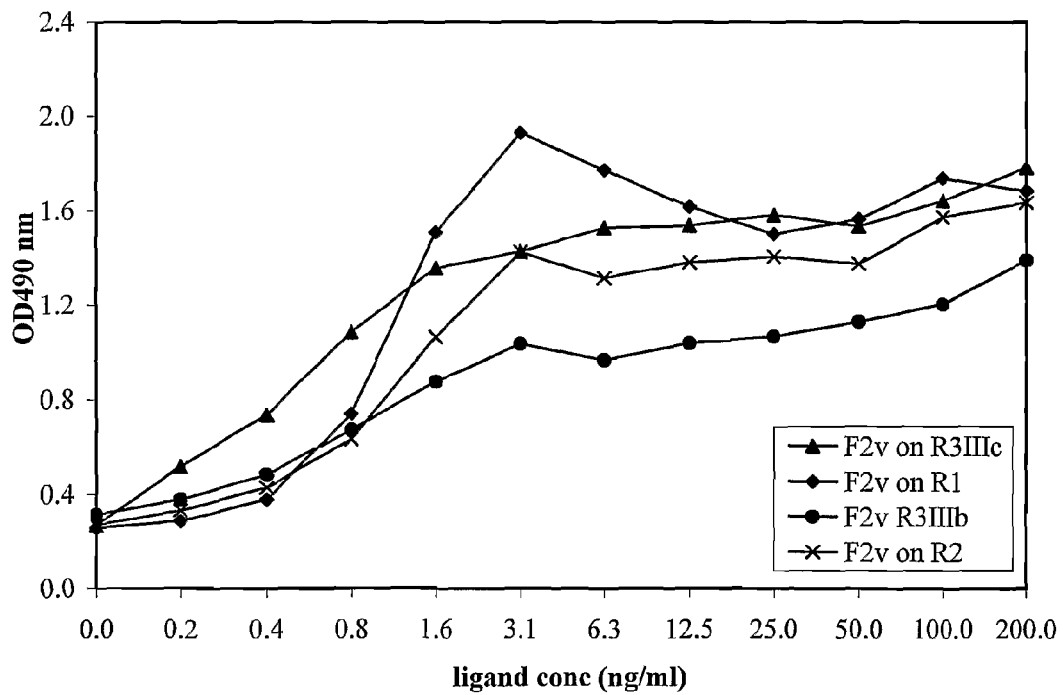

FIG. 2A shows the increase in mitogenicity afforded by the FGF2(3,5Q)-N111G (closed shapes) variant on FGFR1 and FGFR3IIIc (expressing) cells. The wild type FGF-2 is represented by open shapes. FIG. 2B shows the activity of the same variant in a different experiment on cells expressing either FGFR1, FGFR2, FGFR3IIIb or FGFR3IIIc. From these assays the EC50 (effective concentration) of the FGF2(3, 5Q)-N111G variant was calculated. On FGFR1 expressing cells the EC50 ranges from about 0.35 ng/ml to 1.0 ng/ml, and on FGFR3IIIc expressing cells the EC50 ranges from about 0.3 ng/ml to 0.65 ng/ml. The EC50 of FGF-2 wildtype protein is approximately 2.65 ng/ml on FGFR1 cells and 4.2 ng/ml on FGFR3IIIc cells.

Figure 3:
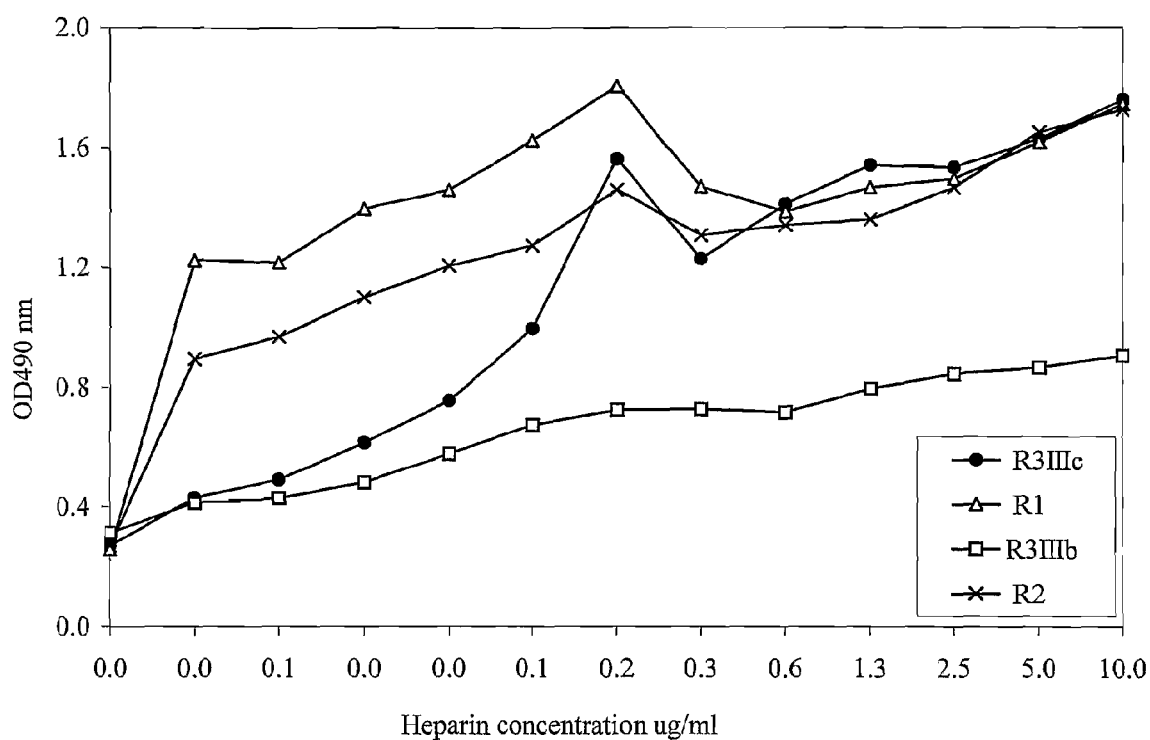
FIG. 3 depicts the mitogenic activity of the FGF-2 variant FGF2(3,5Q)-N111G on FGFR-transfected FDCP cells as a function of heparin concentration.

FIG. 3 shows the dependency of the FGF2(3,5Q)-N111G variant on heparin for the different receptor types. The x-axis represents an increasing concentration of heparin, the concentration of the FGF2v was constant at 10 ng/ml.

Figure 4:
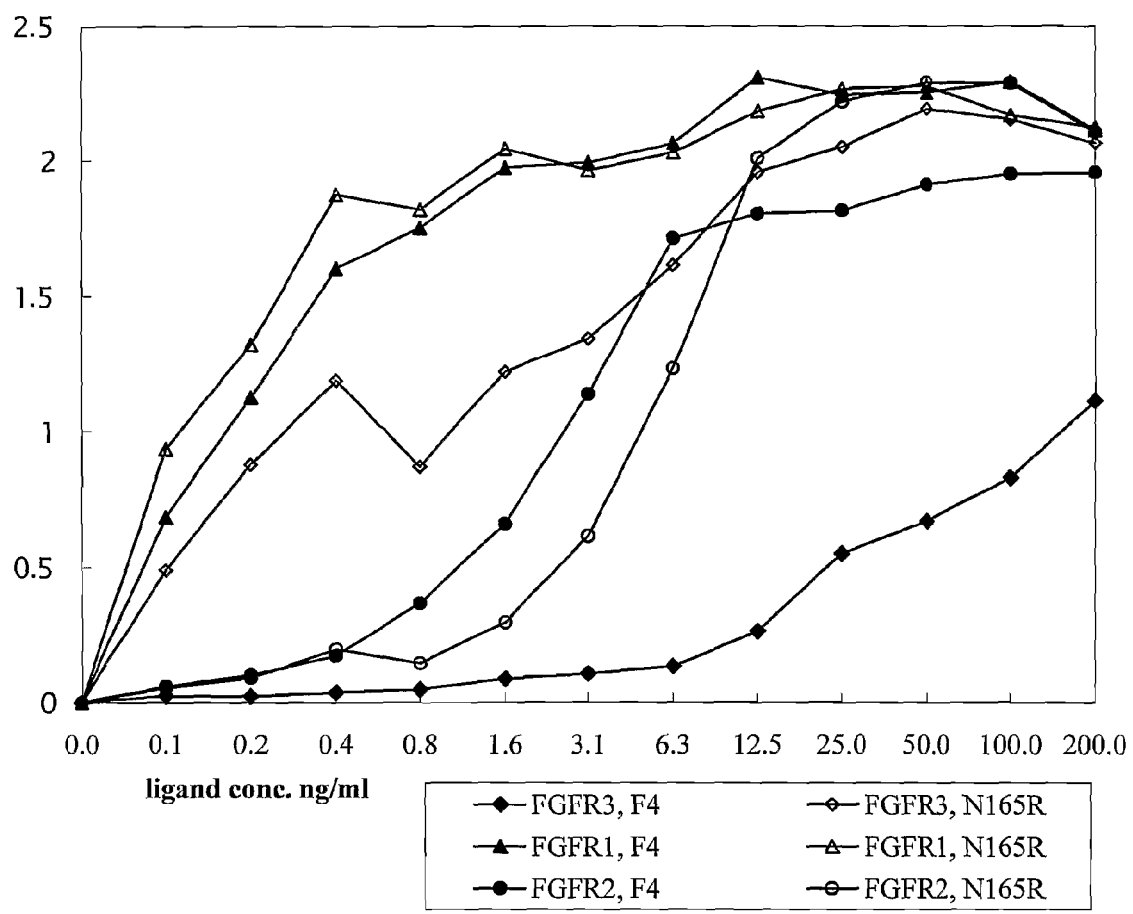
FIG. 4 shows the mitogenic activity induced by the FGF-4 variant, FGF4-L55M-N165R on FGFR-transfected FDCP cells.

FIG. 4 shows the induction of mitogenesis afforded by the L55M-FGF4-N165G variant on FGFR1, FGFR2 and FGFR3IIIc expressing FDCP cells. The wildtype FGF4 is a weak inducer of proliferation on FGFR3 cells while the L55M-FGF4-N165G variant has converted into a potent mitogen.

FIG. 5B shows the reduced level of proliferation induced by R64M-FGF9 both on FGFR3IIIc and FGFR1 cells as compared to parent FGF-9. The enhanced receptor specificity for FGFR3 permits the use of this variant to target to this specific receptor.

FIG. 6 shows the results of the R64M-FGF9 and FGF9-2 variants in a binding assay as described in Example 4. R64M-FGF9 and FGF9-2 appear to function as antagonists of FGF-9.

Example 4

Binding Assay of Truncated FGF Variants to Soluble FGF Receptor Dimer

Binding of FGF proteins to different FGF receptors are determined by measuring the degree of competition for binding to different types of FGFR proteins between a radioiodinated FGF protein and various unlabelled proteins, or by the direct binding of radioiodinated FGF's to various receptor proteins. Binding studies are confirmed by chemical cross-linking of the radioiodinated FGF to soluble receptors in the presence and absence of excess unlabelled FGF.

Sodium heparin from porcine intestinal mucosa (PM-heparin) was obtained from Hepar Industries (Franklin, Ohio). KGF is obtained from UBI (Lake Placid, N.Y.). $^{125}$I was purchased from Amersham (Buckinghamshire, England). FGFs were iodinated using chloramine T. Saline contains 0.05% trypsin, 0.01M sodium phosphate, and 0.02% EDTA (STV). Tissue culture dishes were from Falcon Labware Division, Becton Dickinson (USA), four-well tissue culture plates from Nunc (Rosklide, Denmark).

Soluble FGF receptor proteins were constructed by cloning of the extracellular region of murine FGF receptor 1 (FGFR-1; flg), FGF receptor 2 (FGFR-2; bek), or the KGF receptor (FGFR3(IIIb) or FGFR3IIIc; K-sam) receptors into the alkaline phosphatase-tag expression vector, which encodes for a secreted form of placental alkaline phosphatase (AP). The FGF receptor alkaline phosphatase (FRAP) plasmids were cotransfected into NIH 3T3 cells by electroporation with a selectable neomycin resistance gene. Colonies were selected in G418 (600 µg/ml) and screened for secreted AP enzyme activity in the conditioned medium. Clones which produced a high level of AP activity (2 to 4 A405 units/min/ml) were then used to produce conditioned medium for binding assays.

Components of the soluble receptor binding reaction mixture included FRAP-conditioned medium (0.24 OD units/min), 2 ng/ml $^{125}$I-FGFs and 200 ng/ml heparin. The FGF:heparin:FRAP terniary complex is immunoprecipitated with 20 µl of a 1:1 slurry of anti-AP monoclonal antibodies coupled to protein A Sepharose®. All components were mixed at room temperature. The total volume was adjusted to 200 µl by addition of DMEM containing 0.1% bovine serum albumin. Binding was allowed to proceed for 1 to 2 hours at 24° C., after which time bound receptor complex or the ligand was recovered by centrifugation at 4° C. (10 s at 2,000×g). The pelleted material was washed twice with 500 µl of an ice cold buffer containing HEPES (20 mM), NaCl (150 mM), glycerol (10%) and Triton®X-100 (1%). $^{125}$I-FGF binding was quantitated by counting of the samples in a gamma counter. Alternatively, AP enzyme activity of the FRAP protein is determined by transferring the FRAP receptor bound to Heparin-Sepharose® to a flat-bottom microtiter plate in a volume of 50 µl of PBS. The reaction is initiated by addition of substrate (50 µl of 2× solution of AP assay buffer containing 2M diethanolamine, 1 mM $MgCl_2$, 20 mM homoarginine and 12 mM p-nitrophenyl phosphate). The reaction is followed at room temperature at 405 nm in a kinetic microplate reader.

Receptor binding was determined by quantitating release of labeled FGF from receptors. Briefly, FGF bound to heparan sulfate low affinity sites is released from the cell surface by a 5 minute incubation with an ice cold solution containing 1.6M NaCl, 20 mM HEPES, pH 7.4, and the amount of radioactivity release determined in a gamma-counter. FGF bound to high affinity receptors was dissociated by a 2M NaCl (20 mM acetate buffer, pH 4.0) extraction, and the released labeled FGF is quantitated.

Chemical cross-linking experiments were carried out at room temperature in a volume of 20 µl in siliconized 0.5-ml microcentrifuge tubes. The reaction mixtures contain FGF receptor immobilized to anti-AP monoclonal antibodies coupled to protein A Sepharose® was added to give a final concentration of 0.15 mM, and the mixture incubated for an additional 30 minutes. The reaction was quenched by addition of 1 ml of 200 mM ethanolamine-HCl (pH 8.0) for 30 min. The reaction mixtures were diluted 1:1 with 2×SDS-polyacrylamide gel electrophoresis loading buffer and electrophoresed on an SDS-12% polyacrylamide gel. Cross-linked FGF to the FGF receptor were detected by autoradiography on Kodak XAR film.

Example 5

Effects of FGF Variants on Femoral Growth

Femoral bone cultures are performed by excising the hind limbs of wild type mice. The limbs are carefully cleaned from the surrounding tissue (skin and muscles) and the femora exposed. The femora are removed and further cleared from tissue remains and ligaments. The femora are measured for their initial length, using a binocular with an eyepiece micrometer ruler. The bones are grown in 1 ml of medium with FGF-9, FGF-9 variants, FGF-9 targeting fusion proteins or conjugates, FGF-2 or FGF-2 variants in a 24 well tissue culture dish. The growing medium is A-MEM supplemented with penicillin (100 units/ml), streptomycin (0.1 mg/ml) and Nystatin (12.5 units/ml). In addition, the medium contains BSA (0.2%), β-glycerophosphate (1 mM) and freshly prepared ascorbic acid (50 µg/ml). The bones are cultured for 15 days. Measurements of bone length and medium replacement are performed every three days.

At the end of the experiment, the growth rate of the bones are determined from the slope of a linear regression fit on the length measurements obtained from day 3 to 12. Units given can be converted to length, 40 units=1 mm.

Example 6

Effect of FGF-2 Variants in Bone Fracture Healing

Suitable animal models are used to create bilateral osteotomies to demonstrate the efficacy of the novel variants of the present invention. In a rabbit model a 6 mm osteotomy is created in New Zealand Rabbits in compliance with the Animal Care Committee of the Hebrew University. The ulna was chosen because it is only slightly weight-bearing and allows the creation of a bone defect without requiring a cast or other immobilization treatment. In addition, this gap constitutes a spontaneously healing defect that allows the evaluation of the tested agent. The primary indices of fracture healing are accelerated duration of healing and callus formation. The test compounds consist of FGF-2 variants in a polymeric scaffold which facilitates bone growth.

Surgical Procedure:

Animals are anesthetized according to standard protocol. Gap formation is performed in the mid Ulna bone. A standard volume of 0.2 ml of treatment formulation is put into the gap area in each limb and the fracture is closed. Animals are treated with analgesics for 3 days post operation. The duration of the experiment is 6 weeks.

Healing Time and Quality Assessment:

Healing time evaluation: X-ray grading provides fracture healing status assessment. Rabbits are x-rayed every other week for 5 weeks after surgery. Two orthopedic surgeons score X-rays in a blinded manner according to standard grading scale protocol.

Quality evaluation: at the end of the experiment rabbits are sacrificed and fracture area is sent for histological and mechanical strength evaluation. Histology is scored by a pathologist for evaluation of histological changes during the healing process using standard staining methods, using hematoxylin and eosin for cytoplasm and nucleus. Indigo-Cannin staining is also applied for detection of newly generated callus. Mechanical strength evaluation is performed using the "4 points bending" method.

The treatments groups are: Osteotomy without treatment, Osteotomy treated with polymeric scaffold alone, Osteotomy treated with scaffold containing FGF-2 and an osteotomy treated with scaffold containing FGF-2 variant, FGF2(3,5Q)-N111G.

X-Ray Scoring
0—No callus
1—Primary callus response at one end of bone
2—Primary callus response at both ends of bone
3—Partial external callus union
4—Complete external callus union
5—<30% gap closure
6—>30% gap closure
7—Complete gap closure
8—Partial callus remodeling
9—Complete callus remodeling
Gap Filling Calculation:

$$(A/A+B) \times 100 = \% \text{ gap filling}$$

Example 7

Efficacy of FGF Variants in Distraction Osteogenesis

Distraction osteogenesis is a useful method for bone elongation of extremities in short stature and for the treatment of extensive bone defects. Several procedures for bone lengthening have been developed for use in the clinic. The problems encountered in using this technique include an extended healing time and complications such as non-union or poor quality of the regenerated bone.

The maximal rate of elongation used in the current procedure of limb elongation, while maintaining proper bone healing and reconstitution, is 1 mm/day. Faster elongation rates have resulted in lack of fusion or in the formation of weak bone that breaks easily or cannot bear body weight. In this process, extreme conditions of elongation (1.5 mm/day) will be performed in order to observe a more significant effect of the added compounds on the background of natural healing.

The objectives of the experiment are to assess the quality of bone formation, time of bone formation and safety after elongation using a calcium phosphate (CaP) scaffold embedded with the FGF2 variant.

Treatment Arms:
Control: 5 lambs (5 limbs), no treatment
Treatment 2: 5 lambs (5 limbs): CaP alone
Treatment 3: 5 lambs (5 limbs): CaP with FGF-2 variant
Materials and Methods:
Lambs are assigned randomly into one of the five treatment arms.
Surgical lengthening of the right femur is performed in 25 lambs aged from 3 to 4 months.
Anesthesia and Pre-Mediation:
General anesthesia is given without endotracheal intubation. Intramuscular atropine is given as premedication (0.5 mg/kg), and thiopentone sodium-2.5% (10-15 mg/kg), Fentanyl® (0.0015 mg/kg) and Diazepam® (0.2 mg/kg) is administered intravenously.
Fixation:
A monolateral external fixator (Monotube-Triax®, Stryker Trauma, Geneva, Switzerland) with four pins, two proximal and two distal in each of its pin clamps, is positioned so that the pins are kept away from the growth plates and the surface of the joint. The osteotomy is performed using a pneumatic saw.

Lengthening:
Lengthening begins seven days after surgery for all treatment groups:
Lengthening continues until the limb has been lengthened by 4.5 cm. The total elongation period lasts 30 days at a rate of 1.5 mm/day starting the $8^{th}$ day after surgery.
Treatment:
Lambs are assigned randomly into one of the four treatment arms. All treatments take place during the consolidation period, at day 44.

Treatment 1—Control—To assess the effect during the consolidation period, animals remain without treatment until the end of the trial period.

Treatment 2—To assess the effect of CaP alone during the consolidation period, it will be administered once, one week after completion of elongation.

Treatment 3—To assess the effect of the variant protein during consolidation period, CaP with FGF-2 variant, FGF2-N111G or FGF2(3,5Q)-N111G is administered once, one week after completion of elongation
Follow Up:
Animals are in a restricted area during the extent of the whole experiment and are allowed to feed and walk ad libitum in own cage. Animals are weighed at fixed intervals and general well-being is monitored.

To study the bone formation in the host bone, four different fluorochromes are used as bone markers, administered IM, according to the following schedule: one week after surgery: calcein (green) (Sigma®); two weeks after surgery: alizarin (red) (Sigma®); three weeks after surgery: xylenol (orange) (Fluka®) and three days before sacrifice oxytetracycline will be given (Duphacycline®). The Spalteholz technique is performed after intra-arterial injection of Berlin blue studied through the femoral artery before sacrifice to analyze the vascularization of the lengthened callus in each group.
Completion:
The animals are sacrificed three months after initial surgery by IV injection of 5 meq of KCl, after anesthesia with sodium pentobarbital (1.5 mg/kg weight).
Assessment of Efficacy:
Success is determined in terms of healing time and bone quality obtained after elongation and treatment with FGF2 or FGF2 variant and if no major adverse effects are observed.
X-Ray
Progress of bone healing is followed by X-ray at weeks 1, 2 and 4 after beginning of elongation.
The parameters to be assessed from the X-ray are:
1. Degree of callus formation,
2. Gap closure
3. Remodeling achieved during treatment.
X ray scoring is performed by an orthopedic surgeon, according to an established bone healing grading system.
Histology
The callus is divided into two parts, one for embedding in paraffin, and the other undecalcified, for embedding in methylmethacrylate. For the histological study, the specimens will be fixed in Bouin for 24 hours and decalcified in a solution of PVP-EDTA, at 4° C. Once specimens have been decalcified, they are dehydrated using increasing concentration of alcohols (70%, 80%, 96% and 100%), and after 4 hours in xylene, they are embedded in paraffin at a temperature of 60° C. The specimens are sectioned to 4 µm, and stained with Masson's trichrome, hematoxylin and eosin (H&E), safranin O and von Kossa.

To analyze the mineralization by fluorochromes, the specimens are fixed in formol for one week, then dehydrated using alcohols of increasing proof. After one week in PMMAalcohol and three weeks in PMMA (Technovit 7200 VLC®), specimens will be sectioned with a diamond saw (Exakt®) and trimmed to a thickness of 14 μm. After measuring the sections with ultraviolet light the distance of the bone markers is measured and the bone index formation calculated (distance mm/days)

The proximal parts of both, lengthened and control, tibiae are extracted and cut in lateral and medial parts. The lateral portion is placed in 4% buffered formaldehyde. After decalcification of all the specimens in EDTA, are proceed to embed them in paraffin and cut them into 4 μm slices. Stains of H&E, Masson's trichrome, Safranin 0 and Alcian blue-PAS are applied.

Immunohistochemistry

Specific antibodies recognizing collagen I, collagen II, FGFa (now known as FGF-1), and S-100 are applied to the lengthened callus sections by an indirect two-step method. The 4 μm paraffin sections are dewaxed in xylene and taken through ethanol 100%. After trypsinization, following deparaffinization, endogenous peroxidase is blocked by placing the sections in hydrogen peroxidase solution for 30 min. They are then incubated in the following reagents with appropriate Tris-buffered-saline (CBS: 0.55 M, pH 7.36) washes: normal pig serum for 30 min, abovementioned primary antibodies for 1 hour, a secondary biotinylated antibody for 30 min, and avidin-biotin complex (Dako KO355) for 30 min. The reaction is visualized with chromogen substrate solution (diaminobenzidine, hydrogen peroxidase, TB) and sections are counterstained with Harris's hematoxylin, dehydrated, and mounted. As a negative control, TBS is used in the procedure instead of the primary antibodies. All stained sections are examined and photographed with use of a microscope (Nikon Optiphot-2®, Japan).

Morphometric Analysis

With an image analyzing system (Leica Q 500 MC®) the histomorphometric parameters are determined. With Masson's trichrome stain the following parameters are determined:

1. Trabecular width;
2. Trabecular area;
3. Trabecular erosion surface;
4. Index of trabecular erosion;
5. Number of osteoblasts;
6. Number of osteoclasts per field;
7. Number of osteoclast nuclei;
8. Index of bone reabsorption or number osteoclast nuclei/ osteoclasts.

With von Kossa's stain the following parameters are obtained:

1. Osteoid width;
2. Osteoid—trabecular index, and fluorescence will be used to measure;
3. Bone formation index.

Example 8

Targeting of FGF Variants

The FGF-9 variants having the ability to bind the FGFR3 yet having a reduced capacity to effect a biological response can be used as targeting vectors for the different bioactive agents. CNP is known to increase bone length (see Example 9). CNP derivatives include CNP(1-22), CNP(1-17) and derivatives thereof wherein stability or half life is increased. In particular, FGF9-2-W144G, a 127 amino acid variant which comprises both N- and C-termini truncations and an amino acid substitution at tryptophan 144 (W144), was shown to target efficiently to the growth plate of long bones.

One day old mice pups were injected IP with iodinated FGF9-2-W144G. Animals were sacrificed 2 and 8 hrs later and whole embryo sections were performed. In these pups, the labeled FGF was observed to localize to the growth plate of the hind limb, close to the site of injection. FIGS. 7A and B shows two exposures of the distribution of $I^{125}$ FGF9-2-W144G in the mouse growth plate following IP delivery. P, M, H and T define the proliferating, maturating, hypertrophic and trabecular regions, respectively, of the growth plate. FIG. 7B shows the outline of the cells. FIG. 7A shows strong staining in the hypertrophic zone and some signal in the proliferative and trabecular regions. No other specific sites were labeled by this FGF9 variant. This experiment shows delivery of an exogenously administered compound to the growth plate in vivo and provides a tool for targeted delivery of factors such as natriuretc peptides (NP) or NP analogs. The production of the fusion constructs is illustrated in Example 9. During fetal life and until the end of puberty, longitudinal bone growth takes place via endochondral ossification of the growth plate located at the epiphyses (ends) of long bones. The growth plate is divided into several zones of cartilage forming cells, or chondrocytes, with distinct patterns of gene expression. In the Reserve Zone, cells are small and relatively inactive. In the adjacent Proliferative Zone, chondrocytes proliferate, arrange themselves in columns and eventually undergo hypertrophy. In the Lower Hypertrophic Region towards the cartilage-bone junction, cells are big and highly active but exhibit no further cell division. The matrix surrounding the hypertrophic cells calcifies and the lowermost cells undergo programmed cell death. Cell death is accompanied by the removal of the cartilaginous matrix and its replacement by bone through the concerted action of recruited bone cells, namely osteoclasts and osteoblasts.

Example 9

FGF Variant Fusion Constructs

In addition to members of the FGF family, Natriuretic peptides (NP), and C-type natriuretic peptide (CNP) in particular, have been shown to regulate bone growth. It has been shown that CNP knockout mice which exhibit skeletal phenotypes histologically similar to those seen in achondroplasia mice (Chusho et al., PNAS 98, 4016, 2001). They also reveal the rescue of the CNP knock out skeletal defects by tissue-specific ectopic CNP expression in the growth plate. Moreover, ex vivo experiments (fetal bone organ culture) from wild type animals have shown that CNP, more than BNP and ANP, can induce bone elongation (Yasoda et al., 1998; Mericq et al., 2000). In a currently preferred embodiment of the present invention provided is a method to increase the size of a bone growth plate by treating the bone with a pharmaceutical composition comprising an FGF variant-NP fusion protein. In a currently more preferred embodiment the FGF variant is FGF9-2 and the NP is CNP or an analog thereof.

Two FGF9-2-CNP fusion constructs were prepared, each using four oligonucleotide primers and three PCR reactions. The first, FGF9-2-W144G-CNP(1-22), wherein FGF9-2 lies in a 5' orientation to CNP, was constructed as follows:

FGF9-2-for
(SEQ ID NO: 89)
5'-GGGAATTCCATATGCAGCTATACTGCAGGACTG

CNP-rev
(SEQ ID NO: 90)
5'-AGCTGGATCCTCAGCAACCCAGACCGGACATG

F9-2-CNP-for
(SEQ ID NO: 91)
5'-CACACATTTTTACCTAGAGGAGGGGGAGGTCTGTCCAAAGGTTGC

F9-2-CNP-rev
(SEQ ID NO: 92)
5'-GCAACCTTTGGACAGACCTCCCCCTCCTCTAGGTAAAAATGTGTG

The first PCR reaction (20 cycles) was performed using FGF9-2 for and CNP-rev on an FGF9-2 template. The second (20 cycles) was performed using F9-2-CNP-for and F9-2-CNP-rev on a mCNP (mouse) template. The third PCR reaction (20 cycles) was performed using the products of the two previous PCR reactions as template and amplifying using FGF9-2-for and F922-CNP-rev.

The second fusion construct, CNP-FGF9-2-W144G, comprises the CNP N-terminal to the FGF9-2. The following primers were used:

CNP-for
(SEQ ID NO: 93)
5'-ACGTGACCATATGGGTCTGTCCAAAGGTTG

CNP-F9-2-rev
(SEQ ID NO: 94)
5'CAGTCCTGCAGTATAGCTGCCCTCCCCCTCCCCCTCCCCCTCCGCAAC
CCAGACCGGACATG CNP-F9-2-for
(SEQ ID NO: 95)
5'-ATGTCCGGTCTGGGTTGCGGAGGGGGAGGGGGAGGGGGAGGGCAGCT
ATACTGCAGGACTG P191Stop
(SEQ ID NO: 96)
5'-GGCCCTAGGTCATCTAGGTAAAAATGTGTG The first PCR reaction (20 cycles) was performed using CNP-for and CNP-9-2-rev on a mCNP template. The second (20 cycles) was performed using CNP-F9-2-for and P191 Stop on a mCNP template. The third PCR reaction (20 cycles) was performed using the products of the two previous PCR reactions as template and amplifying using CNP-for and P191Stop primers.

The PCR products were cloned in an expression vector, p80 Bluescript, sequenced and analyzed for accuracy and used to transfect host cells. Fusion protein was produced by methods known in the art. Fusion proteins are analyzed for CNP activity using the Biotrak enzyme immunoassay (EIA, Amersham) that measures the amount of secondary messenger, cyclic GMP (cGMP), elicited after activation of the natriuretic peptide receptor by the peptide on C3H10T1/2 cells.

It will be appreciated by the skilled artisan that the fusion construct can comprise an FGF variant of the present invention fused to a bioactive agent including a peptide or peptide analog or hormone, including growth hormone (GH), IGF-1, TH or PTHrP that is therapeutically beneficial to target to the growth plate.

Example 10

Articular Chondrocyte Culture

Chondrocytes were isolated from pig or human biopsies and cultured in the presence of the variants of the present invention to identify the effect of the variants on proliferation and differentiation. The procedure employed for the isolation and propagation of articular chondrocytes is presented below.
Reagents:
  Dulbecco's MEM (DMEM) (Gibco BRL, cat. no. 41965)
  MEM Non-Essential Amino Acids (Gibco BRL, cat. no. 11140)
  Sodium Pyruvate (Gibco BRL, cat. no. 11360)
  Fetal Bovine Serum (FBS) (Gibco BRL, cat. no. 10270)
  Streptomycin, Penicillin, Nystatin Solution (Biological Indus. Ltd., cat. no. 03 0321)
  Trypsin-EDTA (Gibco BRL, cat. no. T8154) or Versene-Trypsin (Bio LAB Ltd., cat. no. 13.012)
  Collagenase Type 2 (Worthington Biochem. Corp. Cat. No. 4147). A stock solution of 1700 units/ml Collagenase in DMEM was prepared and filtered (0.2 g/m).
Preparation of FBS-DMEM Medium:
  FBS (50 ml), 5 ml of antibiotic solution, 5 ml Sodium Pyruvate, 5 ml MEM non-essential amino acids were added to a 500 ml bottle of DMEM. Where specified, FGF-2, FGF-9 or FGF variants were added to a final concentration of 10 ng/ml.
Isolation of Cells from Cartilage Biopsy:
  A piece of cartilage tissue was minced into 2 to 4 mm pieces with a sterile scalpel. The collagenase solution was diluted 1:4 in FBS-DMEM, added to the tissue sample and left to incubate on a rotator at 37° C., overnight (ON). The cells were centrifuged (1200 rpm 5-10 min). The medium was aspirated, the cells washed in 5 ml medium and recentrifuged. The cells were resuspended in culture medium and seeded in 25 $cm^2$ or 75 $cm^2$ flasks at a concentration of approximately $1 \times 10^6$ cells per flask. The cells were incubated in a 5% $CO_2$ incubator at 37° C. The cell medium was replaced every 2-3 days.
Procedure for Passaging Cells (Trypsinization):
  When the cell culture reached the desired confluency the medium was removed and the cells trypsinized according to standard procedure. The cells were split to 2-3 new flasks and 20 ml fresh pre-warmed medium was added. The expansion of cells and trypsinization was performed as necessary.

Furthermore, the cell population grown on the above matrices expresses several of the chondrocyte differentiation markers. One of several phenotypes expressed during chondrocyte differentiation is glycosaminoglycan (GAG) production. The production of GAGs is identified in histological staining using Alcian blue or toluidine blue and quantitated using the DMB (3,3'-dimethoxybenzidine dihydrochloride) dye method.

Example 11

Cell Proliferation/Differentiation Assay

Articular chondrocytes that have been isolated by enzymatic digestion and maintained in monolayer culture undergo dedifferentiation over time and shift to a fibroblast-like phenotype. This is reflected in part by their morphology and loss of expression of collagen II. The cells are able to undergo proliferation and differentiation into articular chondrocytes under certain growth conditions.

Proliferation of the cartilage cells in the presence of the different variants was quantitated by one of two methods, CyQUANT® (Molecular Probes) or XTT reagent (Biological Industries, Co.). Human or porcine articular chondrocytes ($10^4$-$10^5$ cells/100 ul) were grown in the presence of the variants of the invention (10 ng/ml) in microwell plates. The cells were grown for the several days in DMEM with and without FGF and variants, and the cells processed according to manufacturers instructions. The plates were read in an ELISA reader at A490 nm. Results for human articular chondrocytes are shown in FIGS. 9A-9E.

Articular chondrocytes were isolated from cartilage tissue fragments. Cells were grown using culture media supplemented with Fetal Calf Serum (FCS). Different concentrations of FGF-2 or FGF-9 or FGF variants FGF2-N111G, FGF2-N111R or FGF9-W144G were added to the medium and then to the cells. Medium with variant was exchanged every 2-3 days. Proliferation of cells was determined using CYQUANT™ Cell Proliferation Assay Kit (Molecular Probes).

Morphology of Cultured Cells

Human or porcine articular chondrocytes were grown in culture with or without wild type and variant FGFs for two weeks. The cells were observed under an inverted microscope and stained with fluorescent-conjugated phalloidin.

Figure 8:
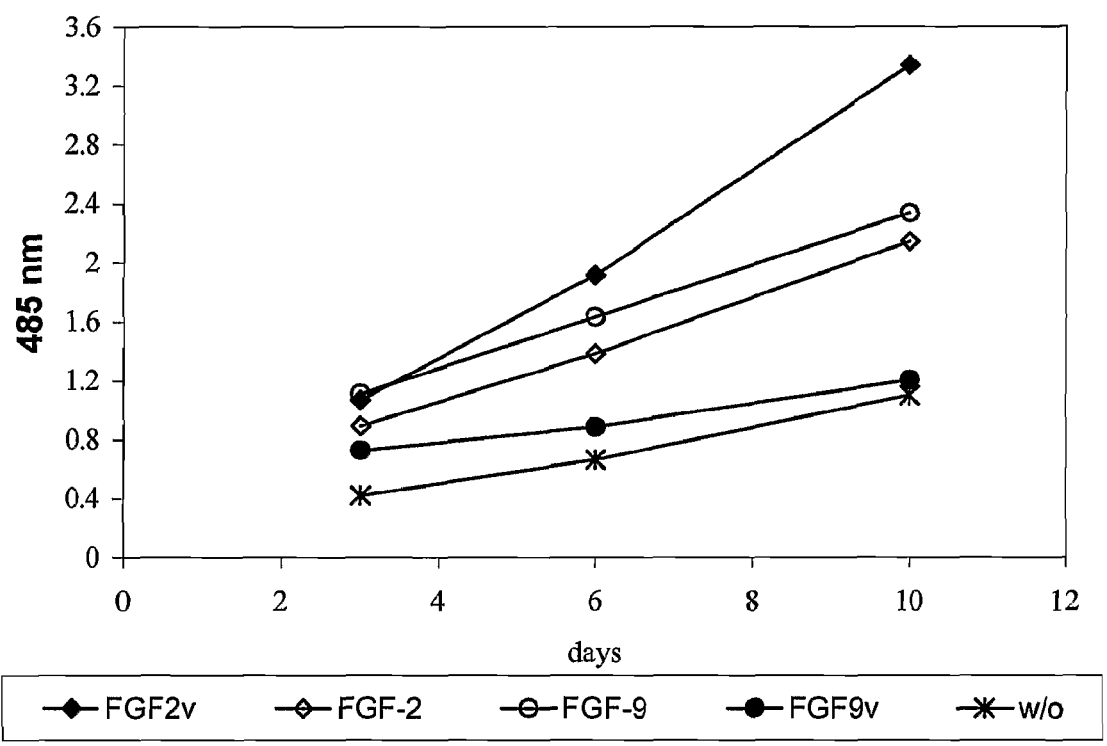
FIG. 8 depicts a proliferation curve of human articular chondrocytes grown in the presence of the variants of the present invention.
Figure 9A:
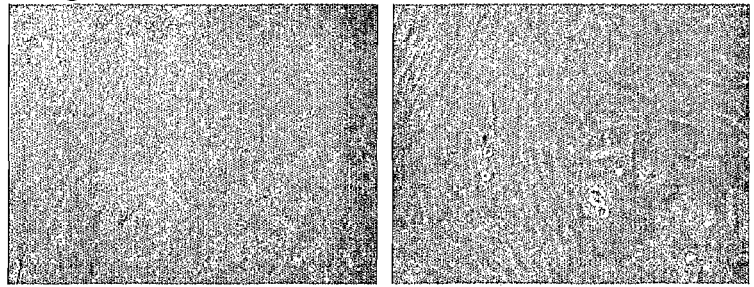
Figure 9A:
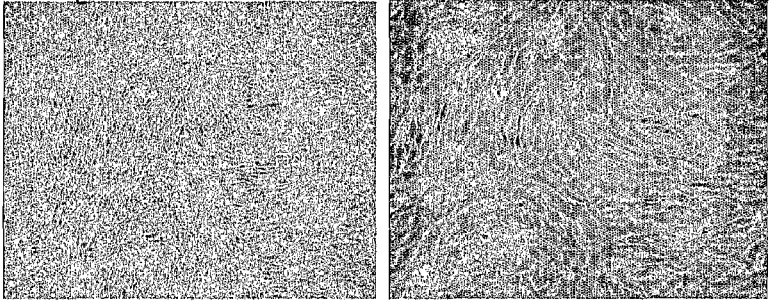
Figure 9C:
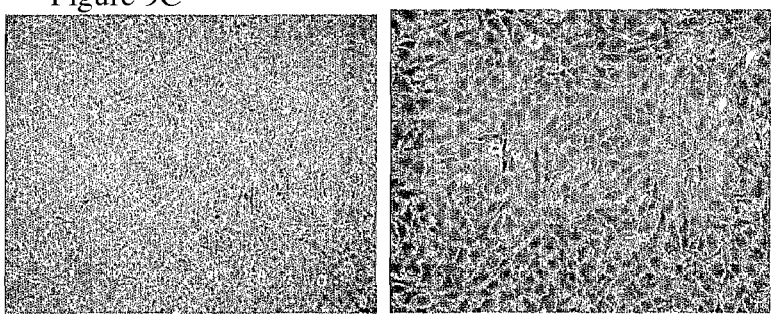
Figure 9D:
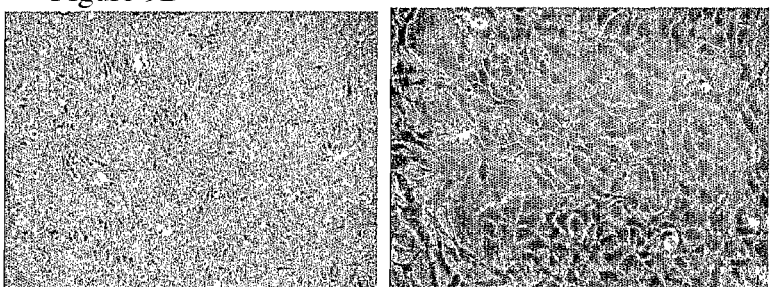
Figure 9E:
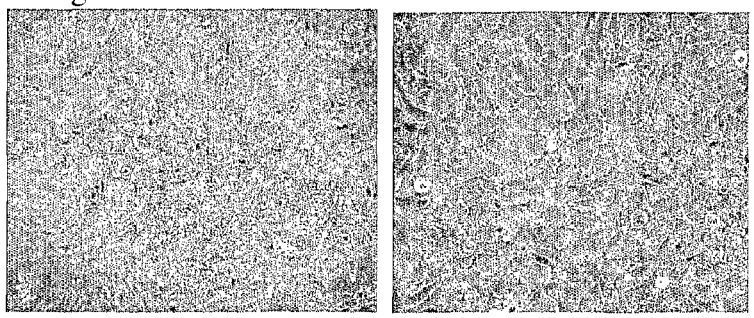

The data from the human articular chondrocytes are shown in FIGS. 8 and 9. FIG. 8 shows the proliferation curve of cells that were cultured in medium with and without added FGF ligand. The ligands FGF-2, FGF2-N111G (FGFV) and FGF9 have a proliferative effect on the articular chondrocytes, while FGF9-W144G (FGFv) does not enhance proliferation.

FIGS. 9A-9E shows human articular chondrocytes following 2 weeks in culture as seen under an inverted microscope. Cells grown without ligand (panel A) exhibit a fibroblastic morphology with undefined borders, while cells grown in the different ligands have variable polygonal shapes. Without wishing to be bound by theory these results suggest that the cells retain the chondrocytic phenotype are able to undergo differentiation once the cells have been induced to proliferate. Furthermore the cells' volume is affected and the cells grown in FGF-9-W144G (panel E) are the largest. The cells in panel B and C were grown in FGF-2 or FGF2(3,5Q)-N111R, respectively.

Figure 10A:
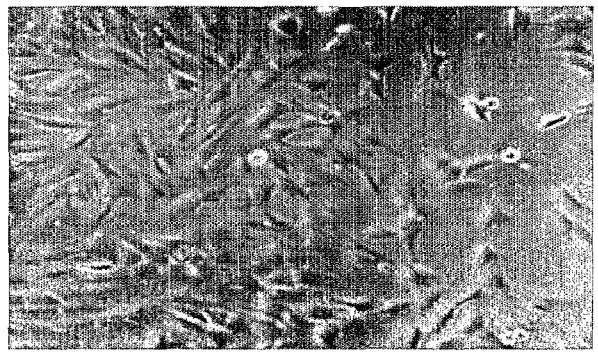
FIGS. 10A-10C show the phenotype of porcine articular chondrocytes grown in the presence of variants of the present invention.
Figure 10B:
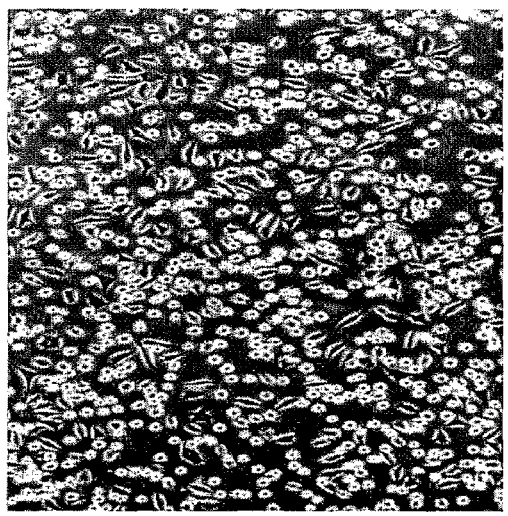
Figure 10C:
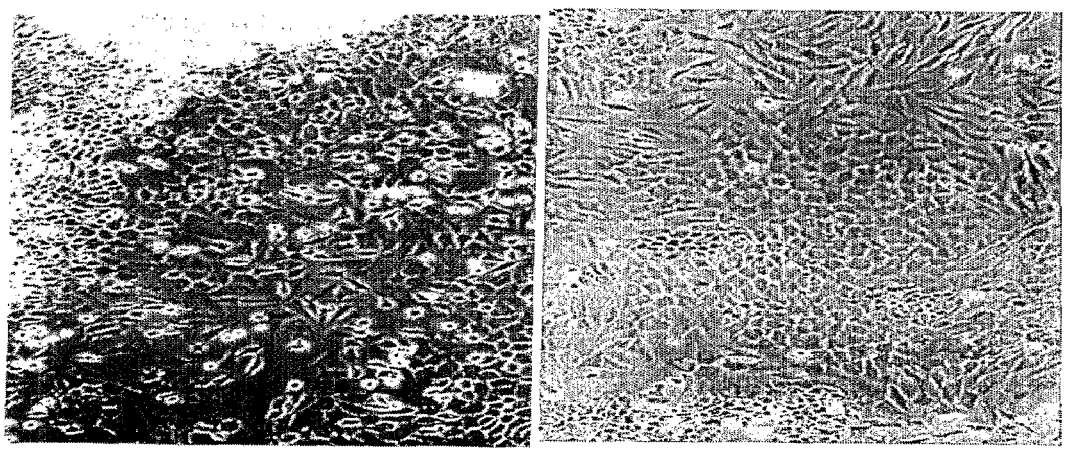
Figure 11A:
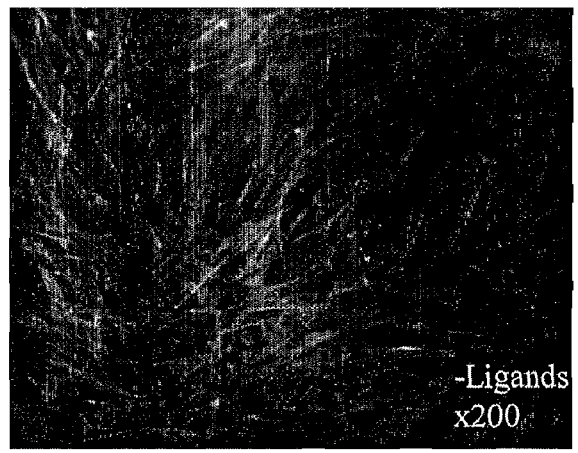
FIGS. 11A-11C show the phenotype of porcine articular chondrocytes grown in the presence of variants of the present invention, phalloidin staining
Figure 11B:
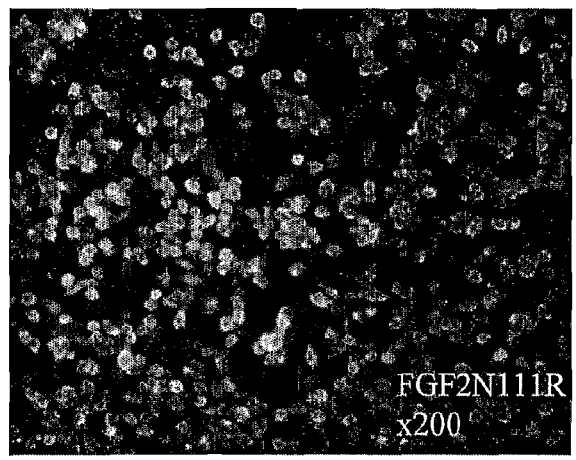
Figure 11C:
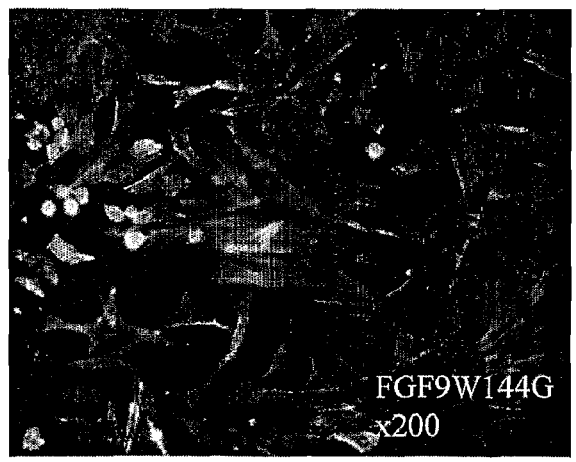

FIG. 10A shows the morphology of porcine articular chondrocytes grown without added ligand. The cells are fibroblast-like and have undefined borders. The cells grown with human FGF2-N111G variant (FIG. 11B) are rounded with highly defined borders, while the cells grown in human FGF9-W114 variant are cuboidal and resemble articular chondrocytes. The cells were stained with fluorescent labeled phalloidin to labels the actin cytoskeleton of the cells. The data are presented in FIGS. 11A-11C. The differences in the actin cytoskeleton between the treatments are very clear. The actin of the cells grown in medium without ligand (FIG. 11A) is elongated and typical of fibroblast-like cells. The actin of cells grown in the FGF2-N111R ligand is round and defined while the actin of cells grown in FGF9-W144G is polygonal.

It is thus possible to alter the cellular phenotype of certain types of cells by exposing them to FGF variants having at least one amino acid substitution in the beta8-beta9 loop.

Example 12

Chondrocyte Pellet Culture

Cell differentiation and morphogenesis was studied in pellet cultures and analyzed by using cell-type-specific markers. $2.5 \times 10^5$ porcine articular chondrocytes that had been expanded in culture in the with and without FGF variants were pelleted in 0.5 ml differentiation medium (DMEM-high glucose containing the following: 1 µM dexamethasone, 1 mM Sodium pyruvate, 50-100 ug/ml ascorbic acid, 0.35 mM proline, 10 ng/ml IGF-1, 10 ng/ml TGFβ, Insulin-Transferrin-Selenium solution (6.25 µg/ml each)) and incubated in differentiation medium in 15 ml polypropylene centrifuge tubes with caps loosened. Medium was exchanged every 2-3 days. The pellets were sectioned using standard methods known in the art and stained with toluidine blue to label the sulfated proteoglycans and immunohistochemically stained with anti-collagen II antibodies.

Figure 12A:
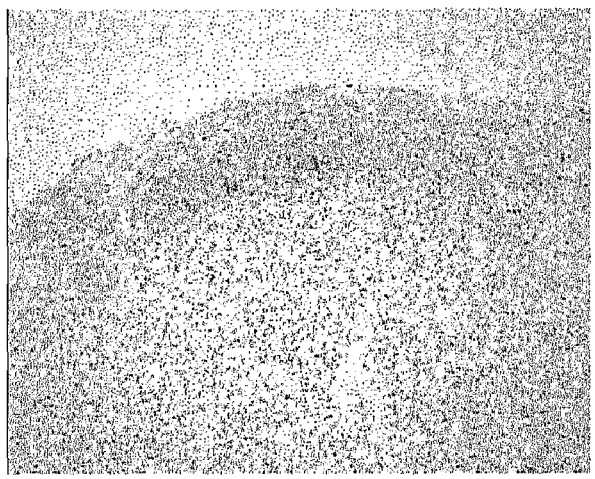
FIGS. 12A-12C show the expression of collagen type II protein in a porcine chondrocyte pellet culture.
Figure 12B:
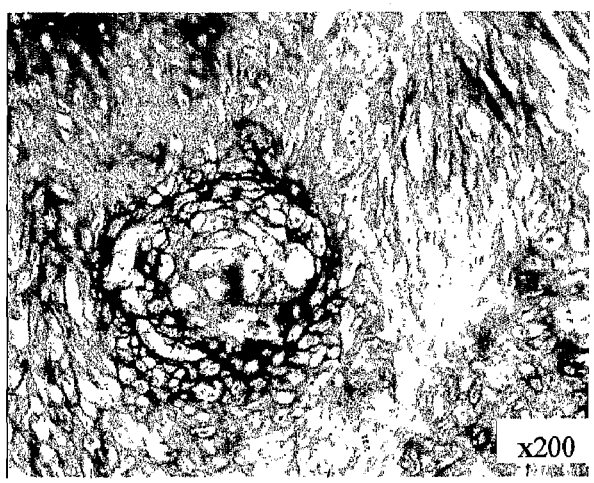
Figure 12C:
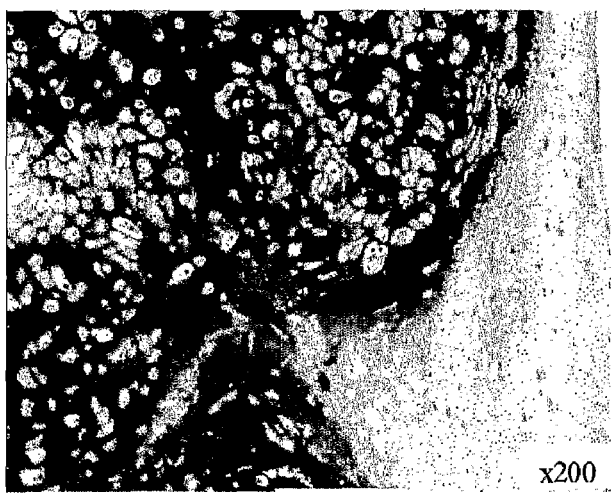

The pellet culture grown in medium with no ligands or with FGF2-N111G showed low collagen II expression. The cultures grown in medium with FGF9-W144G show the appearance of collagen II over time. FIG. 12A shows a small amount of collagen staining after a week, while FIGS. 12B and 12C show a high amount of collagen II protein expression after 2 and 6 weeks, respectively. FIGS. 13A and 13B show the high level of proteoglycan staining in the tissue resulting from the cells cultured in medium comprising the FGF9-W144G variant, while FIGS. 13D and 13C show no toluidine blue staining for cultures grown in medium alone or with FGF-2 variant, respectively.

This result shows that the FGF9-W144G variant is effective in differentiation of cultured articular chondrocyte cells.

The same experiment is performed on chondrocytes isolated from human and other mammalian sources.

Example 13

Goat Articular Cartilage Repair Model

A comparative study to evaluate the efficacy of the FGF variants in treating articular cartilage defects in a goat knee injury model is performed. A total of 6 adult female goats are used. All of the animals undergo a chondrocyte harvest procedure prior to implantation. The collected tissue will be used for preparation of autologous primary chondrocytes. Three weeks post operative, a 4.5 mm diameter and 1.5 mm deep hole are punched out and natural matrix matrices, with or without FGF variants, pre-seeded with different concentrations of allogeneic cells are implanted in the corresponding individual goat for a long term experiment (12 weeks). After 12 weeks, all animals are humanely euthanized. The joints are grossly evaluated for specific changes of the femoral condyle and the contacting surfaces. Histological analysis is performed to determine the structural and cellular response to the implant materials.

Materials and Methods:

Six adult female goats (11-12 months old) are used. In one particular experimental system the different tests include:

| Goat | Treatment Proximal | Treatment Middle | Treatment Distal |
|---|---|---|---|
| 1-3 | Matrix | Matrix + 0.4 × 10⁵ cells | Matrix + 2 × 10⁵ cells |
| 4-6 | Matrix + FGFv | Matrix + FGFv + 0.4 × 10⁵ cells | Matrix + FGFv + 2 × 10⁵ cells |

The variant tested is FGF2(3,5Q)-N111G.

Antibiotics: 2 ml of amoxycillin is injected IM immediately before the procedure and once a day for 4 days after the procedure.

Anesthesia: Pre-medication: 0.05 mg/kg xylazine followed by ketamine-diazepam (4 mg/kg and 2 mg/kg IV) is administered IM.

Surgery and Implantation:

The basic surgical procedure is identical for all subjects. All surgeries are performed under strict asepsis. Peri-operative antibiotics are dosed IM at 2.4 million units of Penicillin procaine (40,000 units/kg SID) at the beginning of the procedure. Anesthesia is induced with xylazine 0.05 mg/kg IM followed by ketamine-diazepam (4 mg/kg and 2 mg/kg IV). The subject is intubated in ventral position and then positioned to left recumbency. Anesthesia is maintained with a gaseous mixture of Isoflurane and oxygen. Analgesia, carprofen 2-4 mg/kg SQ, SID.

Harvest Procedure:

The surgical approach consists of a curved, lateral skin incision made from the distal one-third of the left femur to the level of the tibial plateau and across to the medial side of the tibial spine. Using this method, the skin is bluntly dissected and retracted to allow a lateral parapatellar approach into the stifle joint. An incision is made parallel to the lateral border of the patella and patellar ligament. This extends from the lateral side of the fascia lata along the cranial border of the biceps femoris and into the lateral fascia of the stifle joint. The biceps femoris and attached lateral fascia are retracted allowing an incision into the joint capsule. The joint is extended and the patella luxated medially exposing the stifle joint.

The harvest site is the same as the location of the planned trochlear defect which is created in the right femoral condyle. The defects is approximately 5 mm in diameter and approximately 2.5 mm in depth, and will pass into the subchondral bone. The defects are made on either the lateral or medial wall of the distal trochlear sulcus dependent on individual anatomy. The harvested cartilage layer is approximately 5 mm in diameter and approximately 0.5 mm in depth. The harvested cells are transferred to cell culture medium immediately after harvest for expansion and matrix seeding. The incision is closed in layers using appropriate suture and patterns.

Implantation Procedure:

The trochlear defect is created in the right femoral condyle. The defects are approximately 5 mm in diameter and approximately 2.5 mm in depth, and pass into the subchondral bone. The defects are made on either the lateral or medial wall of the distal trochlear sulcus dependent on individual anatomy. Each defect is filled with the appropriate test article.

The surgical approach consists of a curved, lateral skin incision made from the distal one-third of the left femur to the level of the tibial plateau and across to the medial side of the tibial spine. Using this method, the skin is bluntly dissected and retracted to allow a lateral parapatellar approach into the stifle joint. An incision is made parallel to the lateral border of the patella and patellar ligament. This extends from the lateral side of the fascia lata along the cranial border of the biceps femoris and into the lateral fascia of the stifle joint. The biceps femoris and attached lateral fascia are retracted allowing exposure to the joint capsule. The joint is extended and the patella luxated medially exposing the stifle joint.

With the knee joint fully flexed, the appropriate location for the points of drilling the defect on the trochlear sulcus are identified and marked with a surgical marker. A specially designed cartilage cutter is used to slice through the cartilage outer layer and prevent tearing of the cartilage. The approximate 5 mm diameter core cutter is used under power to create a fixed depth of approximately 2.5 mm, maintaining a plane perpendicular to the tangent of the sulcus. The core of subchondral bone and cartilage is carefully removed. The cutter is carefully removed and any loose cartilage edging is carefully dissected with a scalpel blade. If needed, a handheld powered drill with a specially designed drill bit is used to chamfer the edge of the created defect. This undercutting may assist in providing a mechanical lock with the matrix.

The cartilage defects are copiously flushed with sterile saline prior to insertion of the test article. The appropriate test material is then placed into the defect such that it is in line with the surrounding cartilage and covered with biological glue to maintain in place. A final saline flush of the joint is carefully done. The patella is then reduced and the joint moved through a complete range-of-motion to ensure that there is no impingement due to the implants. This is followed by routine closure of the joint in three or four layers using appropriate suture material.

Post operatively, a modified Thomas splint is applied to the leg. This remains in place for 2 weeks to limit flexing of the operated knee. Post operative checks are made for any animal displaying signs of post operative discomfort. Post operative analgesics are given for 5 days if the animals display any signs of distress of discomfort. All treatments are recorded in the appropriate study documentation.

Necropsy

Animals are humanely sacrificed at 12 weeks postoperatively. Bodyweights are recorded immediately prior to sacrifice. Deep anesthesia is induced with a mixture of ketamine-xylazine and the subject exsanguinated according to the guidelines set forth by the AVMA Panel on Euthanasia (JAVMA, March 2000).

Gross evaluation and sample collection as described in Table 4 are performed. Lymph nodes in close proximity to the joint is examined. The articulating surfaces opposing the defect sites are examined for any abnormal joint surface. Additionally, gross evaluations of the knee joints is made to determine the cartilage repair based on previous scoring criteria listed in Table 4. Femora, patellae, synovium, and popliteal lymph nodes are harvested and placed into appropriately labeled containers. Immediately following tissue harvest, gross morphological examination of the cartilage surface is done as described above and photographic records made of each specimen.

TABLE 4

Gross Evaluation and Sample Collection

| Sample | Gross Evaluation | Sample collection | Photograph and Score |
|---|---|---|---|
| Heart | | | |
| Lungs | | | |
| Kidneys | | | |
| Spleen | | | |
| Popliteal lymph nodes | X | x | |
| Knee joint (includes articulating defect site) | X | x | x |

Gross Morphological Observations

After collection of the knee joints, the joints are opened, photographed and the surface of the defect site scored as indicated in Table 5. The synovial membrane is examined for any inflammation. Joint fluid is collected and analyzed.

TABLE 5

Scoring Criteria for Gross Morphological Evaluations

| Characteristic | Grading | Score |
|---|---|---|
| Edge Integration | Full | 2 |
| (new tissue relative to native cartilage) | Partial | 1 |
| | None | 0 |
| Smoothness of the cartilage surface | Smooth | 2 |
| | Intermediate | 1 |
| | Rough | 0 |
| Cartilage surface, degree of filling | Flush | 2 |
| | Slight depression | 1 |
| | Depressed/overgrown | 0 |
| Color of cartilage, opacity or | Transparent | 2 |
| translucency of the neocartilage | Translucent | 1 |
| | Opaque | 0 |

Histology and Histological Evaluation

Immediately after dissection and following gross joint surface observations, the joints is placed in 10% phosphate buffered formalin (at least ten-fold volume) for at least 48 hours and sent for histological processing. After fixation in 10% phosphate buffered formalin, the specimens is grossly trimmed to remove extra tissue. The tissue blocks are cut approximately ⅓ of the distance in from the exterior implant/tissue interface in order to examine them grossly. Contact radiographs is taken prior to the commencement of decalcification.

The tissues are decalcified in 10% EDTA until radiographs of the decalcified sections assures complete decalcification. Once complete decalcification is determined, the specimens is dehydrated through an ethanol series and paraffin embedded. The specimens is sectioned to 5-10 μm. One section is stained with H&E and another sequential section with Safranin O counter-stained with Fast Green. For histologic analysis of the sections, the scoring scale according to Frenkel is used.

Histological evaluation is performed to measure the following parameters: Characteristics of the neo-formed tissue, regularity of the joint surface of the regenerated tissue, structural integrity and thickness of the regenerated tissue, endochondral ossification and state of the cells in the remaining cartilage.

Example 14

Pharmacokinetics

Methods for detecting administered compounds in the blood or tissue of treated mammals are known in the art. The pharmacokinetic properties of the administered compounds are determined using such methods. In animal models, radiolabelled oligonucleotides or peptides can be administered and their distribution within body fluids and tissues assessed by extraction of the oligonucleotides or peptides followed by autoradiography (Agrawal et al PNAS 88:7595, 1991). Other methods include labeling of a peptide with a reporter moiety, including fluorescent or enzyme labels, administration to an animal, extraction of the peptide from body fluids and organs followed by HPLC analysis. Alternatively, immunohistochemical methods are used for detection of the administered peptide in tissue. The present invention contemplates reporter labeled FGF polypeptides and chimeras, fusion protein, hybrids and conjugates using the same.

Example 15

Effect of Variants on PC12 Cells

To investigate whether neuronal PC12 cells respond differently to the FGFs and FGF variants, cells were exposed to FGF-2, FGF2-N111R, FGF-9 and FGF9-W144G.

The PC12 cell line was originally cloned from a transplantable rat adrenal medullary pheochromocytoma. The cells were grown in DMEM with high glucose supplemented with 10% horse serum, 5% fetal calf serum, 130-units/ml penicillin and 0.1 mg/ml streptomycin and 0.25-40 ng/ml FGF or variant in a humidified incubator at 37° C. To harvest the cell, the cell layer was washed with PBS-EDTA. The cells were collected and centrifuged for 5 min, 2000 rpm. The cells were resuspended in 5 ml DMEM and plated.

After 3 days in culture, both FGF-2 and FGF-9 induced neuronal differentiation at a similar level, as determined by the observation of neurite extensions. Close observation of the cultures demonstrated that the length of the neurite outgrowth induced by FGF-2 was typically longer than that induced by FGF-9. Importantly, the variants induced an inverse effect when compared to their wild type counterpart. While FGF2-N111R was more potent, as determined by the number and length of the neurite extensions, than FGF-2, FGF9-W144G had the weakest activity of all tested ligands exerting minimal differentiation even at the highest concentration employed (40 ng/ml).

The introduction of a mutation in the β8-β9 loop of the FGF-2 and FGF-9 ligands resulted in polypeptides having a selective effect on the cells in culture.

While the present invention has been particularly described, persons skilled in the art will appreciate that many variations and modifications can be made. Therefore, the invention is not to be construed as restricted to the particularly described embodiments, rather the scope, spirit and concept of the invention will be more readily understood by reference to the claims which follow.

What is claimed is:

1. A polynucleotide encoding a variant of fibroblast growth factor 2 (FGF-2) that has at least one amino acid substitution in the beta 8-beta 9 loop, and at least one of the following attributes compared to the corresponding wild type FGF-2: enhanced specificity for one receptor subtype; increased biological activity mediated by at least one receptor subtype with equivalent or reduced activity mediated through another receptor subtype; enhanced affinity to at least one receptor subtype; or increased cell proliferation mediated through one receptor subtype, wherein the polynucleotide comprises the nucleic acid sequence of SEQ ID NO: 18, wherein the codon encoding asparagine at positions 331-333 is replaced by a codon encoding an amino acid residue selected from the group consisting of: glycine, arginine, valine, glutamic acid, and serine.

2. The polynucleotide of claim 1, comprising the nucleic acid sequence of SEQ ID NO: 19 or 20 wherein the codon encoding asparagine at positions 331-333 is replaced by a codon encoding glycine or arginine.

3. The polynucleotide of claim 1, comprising the nucleic acid sequence of SEQ ID NO: 21, wherein nucleotide positions 9 and 15 are either adenine or guanine and the codon encoding asparagine at positions 331-333 is replaced by a codon encoding an amino acid residue selected from the group consisting of: glycine, arginine, valine, glutamic acid, and serine.

4. The polynucleotide of claim 3, comprising the nucleic acid sequence of SEQ ID NO: 22, wherein nucleotide positions 9 and 15 are either adenine or guanine and the N at position 333 is selected from the group consisting of adenine, cytosine, guanine and thymine.

5. The polynucleotide of claim 1, wherein the FGF-2 variant has activity at least 2-fold the activity of the wild type FGF-2 in terms of proliferation induced by the variant in fibroblast growth factor receptor (FGFR) bearing cells.

6. The polynucleotide of claim 5, wherein the FGFR is fibroblast growth factor receptor 1.

* * * * *

UNITED STATES PATENT AND TRADEMARK OFFICE
CERTIFICATE OF CORRECTION

PATENT NO.          : 8,119,783 B2
APPLICATION NO.     : 12/416435
DATED               : February 21, 2012
INVENTOR(S)         : Bogin et al.

It is certified that error appears in the above-identified patent and that said Letters Patent is hereby corrected as shown below:

Title Page:
Item (56) References Cited, OTHER PUBLICATIONS
   Sfiao, Zhan-Qiang et al. reference: change "Sfiao" to -- Shao --.
   Bailly K. et al. reference: change "333-343" to -- 333-344 --.
   Barry A. Springer et al. reference: after "Receptor" delete ".;".
   Ezzat, S. et al. reference: change "69-77" to -- 69-78 --.
   Givol and Yayon reference: change "3369" to -- 3362-3369 --.
   Necht et al. reference: change "Necht" to -- Hecht --; and after "Crystallogr." change "53 378" to
     -- 57: 378-384 --.
   Nishimura, T. et al. reference: change "Liver'"'" to -- Liver" --.
   Ornitz et al. reference: change "2 11, 15292" to -- 271: 15292-15297 --.
   J. Zhang et al. reference: change "1611" to -- 1 beta --.

Column 40:
Line 28, after "expressing" delete "either".

Signed and Sealed this
Tenth Day of April, 2012

David J. Kappos
*Director of the United States Patent and Trademark Office*